United States Patent
Clasby et al.

(10) Patent No.: US 7,741,318 B2
(45) Date of Patent: Jun. 22, 2010

(54) PYRAZOLO [1,5-A]PYRIMIDINE ADENOSINE $A_{2a}$ RECEPTOR ANTAGONISTS

(75) Inventors: Martin C. Clasby, Plainsboro, NJ (US); Samuel Chackalamannil, Califon, NJ (US); Bernard R. Neustadt, West Orange, NJ (US); Xiaobang Gao, Keasbey, NJ (US)

(73) Assignee: Schering Corporation, Kenilworth, NJ (US)

( * ) Notice: Subject to any disclaimer, the term of this patent is extended or adjusted under 35 U.S.C. 154(b) by 158 days.

(21) Appl. No.: 11/311,195

(22) Filed: Dec. 19, 2005

(65) Prior Publication Data

US 2006/0135526 A1  Jun. 22, 2006

Related U.S. Application Data

(60) Provisional application No. 60/638,028, filed on Dec. 21, 2004.

(51) Int. Cl.
| | |
|---|---|
| C07D 243/08 | (2006.01) |
| C07D 295/02 | (2006.01) |
| C07D 295/16 | (2006.01) |
| C07D 487/04 | (2006.01) |
| A61K 31/519 | (2006.01) |
| A61K 31/5377 | (2006.01) |
| A61K 31/497 | (2006.01) |
| A61K 31/5513 | (2006.01) |
| A61P 25/16 | (2006.01) |

(52) U.S. Cl. .............. 514/218; 540/575; 544/218; 544/228; 514/259.31; 514/233.2; 514/252.16

(58) Field of Classification Search .............. None
See application file for complete search history.

(56) References Cited

U.S. PATENT DOCUMENTS 5,602,136 A * 2/1997 Ruhter et al. ............ 514/257
2007/0179161 A1* 8/2007 Parratt et al. ........... 514/259.3

FOREIGN PATENT DOCUMENTS

| EP | 0 976 753 | 2/2000 |
|---|---|---|
| WO | WO 01/17999 | 3/2001 |
| WO | WO 01/23388 | 4/2001 |
| WO | WO 2004/026229 | 4/2004 |
| WO | WO 2004/092171 | 10/2004 |

OTHER PUBLICATIONS

Kulisevsky (Clinical Neuropharmacology). Kulisevsky (Clinical Neuropharmacology, 2002, 25(1), abstract).*
Morelli (Experimental Neurology, 2003, 184, pp. 20-23).*
Tuite (Expert. Opin. Investig. Drugs, 2003, 12(8), pp. 1335-1352).*
Bibbiani et al. (Experimental Neurology, 2003, 184, pp. 285-294).*
Konitsiotis (Expert. Opin. Investig. Drugs, 2005, 14(4), 377-392).*
PCT International Search Report mail date Sep. 1, 2006 for corresponding PCT Application No. PCT/US2005/045658.

* cited by examiner

Primary Examiner—Susanna Moore
(74) Attorney, Agent, or Firm—Krishna G. Banerjee; Anita W. Magatti

(57) ABSTRACT

Compounds having the structural formula I

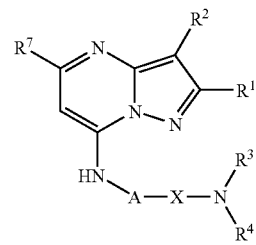

are disclosed, wherein
A is alkylene, or optionally substituted arylene, cycloalkylene or heteroaryldiyl;
X is —C(O)— or —S(O)$_2$—;
$R^1$ is alkyl or cycloalkyl;
$R^2$ is hydrogen, halo or —CN;
$R^3$ is hydrogen or alkyl;
$R^4$ is hydrogen, alkyl, alkoxy, hydroxyalkyl, aminoalkyl-, cycloalkyl, heterocycloalkyl, heterocycloalkyl substituted by alkyl, optionally substituted arylalkyl or optionally substituted heteroarylalkyl;
or $R^3$ and $R^4$, form an optionally substituted 5-7 membered ring, said ring optionally comprising an additional heteroatom ring member;
$R^7$ is alkyl, optionally substituted phenyl, optionally substituted heteroaryl, cycloalkyl, halo, morpholinyl, optionally substituted piperazinyl, or optionally substituted azacycloalkyl.

Also disclosed is the use of the compounds in the treatment of Parkinson's disease, alone or in combination with other agents for treating Parkinson's disease, pharmaceutical compositions comprising them and kits comprising the components of the combinations.

20 Claims, No Drawings

PYRAZOLO [1,5-A]PYRIMIDINE ADENOSINE $A_{2a}$ RECEPTOR ANTAGONISTS

CROSS REFERENCE TO RELATED APPLICATION

This application claims the benefit of U.S. Provisional Application No. 60/638,028, filed Dec. 21, 2004.

BACKGROUND

The present invention relates to substituted pyrazolo[1,5-a]pyrimidine adenosine $A_{2a}$ receptor antagonists, the use of said compounds in the treatment of central nervous system diseases, in particular Parkinson's disease, and to pharmaceutical compositions comprising said compounds.

Adenosine is known to be an endogenous modulator of a number of physiological functions. At the cardiovascular system level, adenosine is a strong vasodilator and a cardiac depressor. On the central nervous system, adenosine induces sedative, anxiolytic and antiepileptic effects. On the respiratory system, adenosine induces bronchoconstriction. At the kidney level, it exerts a biphasic action, inducing vasoconstriction at low concentrations and vasodilation at high doses. Adenosine acts as a lipolysis inhibitor on fat cells and as an antiaggregant on platelets.

Adenosine action is mediated by the interaction with different membrane specific receptors which belong to the family of receptors coupled with G proteins. Biochemical and pharmacological studies, together with advances in molecular biology, have allowed the identification of at least four subtypes of adenosine receptors: $A_1$, $A_{2a}$, $A_{2b}$ and $A_3$. $A_1$ and $A_3$ are high-affinity, inhibiting the activity of the enzyme adenylate cyclase, and $A_{2a}$ and $A_{2b}$ are low-affinity, stimulating the activity of the same enzyme. Analogs of adenosine able to interact as antagonists with the $A_1$, $A_{2a}$, $A_{2b}$ and $A_3$ receptors have also been identified.

Selective antagonists for the $A_{2a}$ receptor are of pharmacological interest because of their reduced level of side affects. In the central nervous system, $A_{2a}$ antagonists can have antidepressant properties and stimulate cognitive functions. Moreover, data has shown that $A_{2a}$ receptors are present in high density in the basal ganglia, known to be important in the control of movement. Hence, $A_{2a}$ antagonists can improve motor impairment due to neurodegenerative diseases such as Parkinson's disease, senile dementia as in Alzheimer's disease, and psychoses of organic origin.

Some xanthine-related compounds have been found to be $A_1$ receptor selective antagonists, and xanthine and non-xanthine compounds have been found to have high $A_{2a}$ affinity with varying degrees of $A_{2a}$ vs. $A_1$ selectivity. Certain imidazolo- and pyrazolo-substituted triazolo-pyrimidine adenosine $A_{2a}$ receptor antagonists have been disclosed previously, for example in WO 95/01356; WO 97/05138; and WO 98/52568. Certain pyrazolo-substituted triazolo-pyrimidine adenosine $A_{2a}$ receptor antagonists are disclosed in U.S. Ser. No. 09/207,143, filed May 24, 2001. Certain imidazolo-substituted triazolo-pyrimidine adenosine $A_{2a}$ receptor antagonists are disclosed in U.S. Provisional Application No. 60/329,567, filed Oct. 15, 2001. U.S. Pat. No. 5,565,460 discloses certain triazolo-triazines as antidepressants; EP 0976753 and WO 99/43678 disclose certain triazolo-pyrimidines as adenosine $A_{2a}$ receptor antagonists; and WO 01/17999 discloses certain triazolo pyridines as adenosine $A_{2a}$ receptor antagonists.

SUMMARY OF THE INVENTION

The present invention relates to a compound represented by the structural formula I

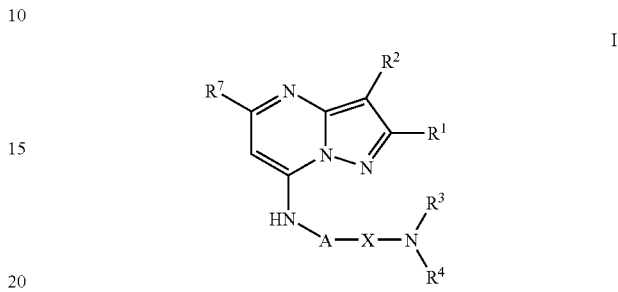

or a pharmaceutically acceptable salt thereof, wherein:

A is alkylene, $R^{16}$-arylene, $R^{16}$-cycloalkylene or $R^{16}$-heteroaryidiyl;

X is —C(O)— or —S(O)$_2$—;

$R^1$ is alkyl or cycloalkyl;

$R^2$ is hydrogen, halo or —CN;

$R^3$ is hydrogen or alkyl;

$R^4$ is hydrogen, alkyl, alkoxy, hydroxyalkyl, -alkyl-NR$^{14}$R$^{15}$, cycloalkyl, heterocycloalkyl, heterocycloalkyl substituted by alkyl, $R^8$-arylalkyl or $R^8$-heteroarylalkyl;

or $R^3$ and $R^4$, together with the nitrogen to which they are attached, form a 5-7 membered ring, said ring optionally comprising an additional heteroatom ring member selected from the group consisting of —O—, —S— and —N(R$^{17}$)—, said ring being optionally substituted by alkyl, hydroxyalkyl, $R^8$-arylalkyl, $R^8$-heteroarylalkyl, —N(R$^9$)—C(O)alkyl, —CO$_2$-alkyl, —C(O)NR$^{10}$R$^{11}$ or heterocycloalkyl;

or $R^3$ and $R^4$, together with the nitrogen to which they are attached, form the group

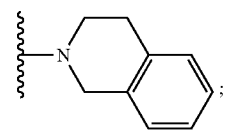

$R^7$ is alkyl, $R^{12}$-phenyl, $R^{12}$-heteroaryl, cycloalkyl, halo, morpholinyl,

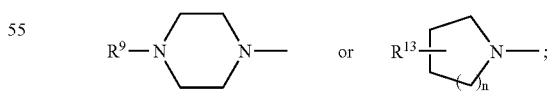

n is 1 or 2;

$R^8$ is 1-3 substituents independently selected from the group consisting of hydrogen, alkyl, halo, alkoxy, —CO$_2$H, —CO$_2$-alkyl, —CF$_3$, —CN, —CO$_2$NR$^{14}$R$^{15}$, —SO$_2$-alkyl, —SO$_2$NR$^{14}$R$^{15}$ and —NR$^{14}$R$^{15}$;

$R^9$ is hydrogen or alkyl;

$R^{10}$ and $R^{11}$ are independently selected from the group consisting of alkyl and cycloalkyl; or $R^{10}$ and $R^{11}$ form a $C_4$-$C_5$ alkylene chain and together with the nitrogen to which they are attached, form a 5- or 6-membered ring;

$R^{12}$ is 1 to 3 substituents independently selected from the group consisting of hydrogen, alkyl, halo, alkoxy, —$CO_2H$, —$CO_2$-alkyl, —$CF_3$, —CN, —$CO_2NR^{14}R^{15}$, —$SO_2$-alkyl, —$SO_2NR^{14}R^{15}$ and —$NR^{14}R^{15}$;

$R^{13}$ is H, OH, hydroxyalkyl or alkyl;

$R^{14}$ and $R^{15}$ are independently selected form the group consisting of hydrogen, alkyl and cycloalkyl;

$R^{16}$ is 1 to 3 substituents independently selected from the group consisting of hydrogen, alkyl, halo, OH and alkoxy; and $R^{17}$ is hydrogen, alkyl, cycloalkyl or $R^8$-arylalkyl.

Another aspect of the invention is a pharmaceutical composition comprising a therapeutically effective amount of at least one compound of formula I in a pharmaceutically acceptable carrier.

Yet another aspect of the invention is a method of treating central nervous system diseases such as depression, cognitive diseases and neurodegenerative diseases such as Parkinson's disease, senile dementia or psychoses, and stroke, comprising administering at least one compound of formula I to a mammal in need of such treatment.

The invention also relates to the treatment of attention related disorders such as attention deficit disorder (ADD) and attention deficit hyperactivity disorder (ADHD). The invention also relates to the treatment or prevention of Extra-Pyramidal Syndrome (e.g., dystonia, akathisia, pseudoparkinsonism and tardive dyskinesia), the treatment of primary (idiopathic) dystonia, and the treatment or prevention of dystonia in patients who exhibit dystonia as a result of treatment with a tricyclic antidepressant, lithium or an anticonvulsant, or who have used cocaine, comprising administering at least one compound of formula I to a mammal in need of such treatment. The invention further relates to treatment of abnormal movement disorders such as restless leg syndrome (RLS) or periodic limb movement in sleep (PLMS), comprising administering to a patient in need thereof a therapeutically effective amount of at least one compound of formula I.

In particular, the invention is drawn to the method of treating Parkinson's disease comprising administering at least one compound of formula I to a mammal in need of such treatment.

Still another aspect of the invention is a method of treating Parkinson's disease with a combination of at least one compound of formula I and one or more agents useful in the treatment of Parkinson's disease, for example dopamine; a dopaminergic agonist; an inhibitor of monoamine oxidase, type B (MAO-B); a DOPA decarboxylase inhibitor (DCI); or a catechol-O-methyltransferase (COMT) inhibitor. Also claimed is a pharmaceutical composition comprising at least one compound of formula I and one or more agents known to be useful in the treatment of Parkinson's in a pharmaceutically acceptable carrier.

The invention also comprises a method of treating EPS, dystonia, RLS or PLMS comprising administering a combination of at least one compound of formula I with another agent useful in treating RLS or PLMS, such as levodopa/carbidopa, levodopa/benserazide, a dopamine agonist, a benzodiazepine, an opioid, an anticonvulsant or iron, to a patient in need thereof.

In the method comprising the administration of the combination of the invention, one or more compounds of formula I and one or more other anti-Parkinson'agents can be administered simultaneously or sequentially in separate dosage forms. Similarly, one or more compounds of formula I and one or more other agents useful in treating EPS, dystonia, RLS or PLMS can be administered simultaneously or sequentially in separate dosage forms. Therefore, also claimed is a kit comprising in separate containers in a single package pharmaceutical compositions for use in combination to treat Parkinson's disease wherein one container comprises a pharmaceutical composition comprising an effective amount of a compound of formula I in a pharmaceutically acceptable carrier, and wherein, in separate containers, one or more pharmaceutical compositions each comprise an effective amount of an agent useful in the treatment of Parkinson's disease, EPS, dystonia, RLS or PLMS in a pharmaceutically acceptable carrier.

DETAILED DESCRIPTION

Referring to compounds of formula I above, preferred compounds of formula I are those wherein $R^1$ is methyl or cyclopropyl.

A is preferably $R^{16}$-arylene, more preferably phenylene.

$R^7$ is preferably $R^{12}$-phenyl, pyridyl or

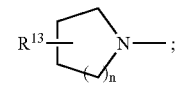

more preferably $R^{12}$ is hydrogen. When $R^7$ is $R^{13}$-azacycloalkyl, preferably n is 1 and $R^{13}$ is hydroxyalkyl, with

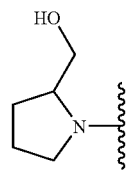

being more preferred. When X is —$S(O)_2$— and $R^7$ is pyridyl, it is preferably 2-pyridyl; when X is —C(O)— and $R^7$ is pyridyl, it can be 2-, 3- or 4-pyridyl.

When X is —$S(O)_2$—, $R^2$ is preferably CN, Cl or Br when $R^1$ is methyl, and $R^2$ is preferably hydrogen when $R^1$ is cyclopropyl.

When X is —$S(O)_2$—, then —$NR^3R^4$ is preferably selected from the group consisting of:

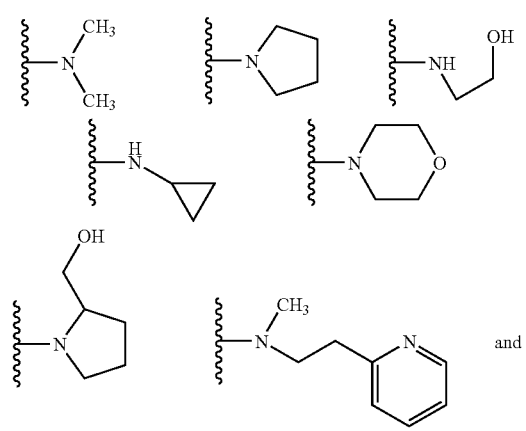

and

When X is —C(O)—, —NR³R⁴ is preferably selected from the group consisting of:

More preferred are compounds of formula I wherein X is —S(O)₂—, A is phenylene, R¹ is methyl, R² is Br, R⁷ is phenyl or

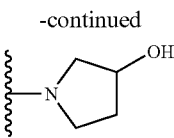

and —NR³R⁴ is

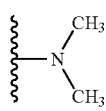 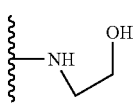

Also more preferred are compounds of formula I wherein X is —C(O)—, A is phenylene, R¹ is cyclopropyl or methyl, R² is hydrogen, R⁷ is phenyl or and —NR³R⁴ is when R¹ is cyclopropyl, or —NR³R⁴ is when R¹ is methyl.

As used herein, the term "alkyl" means an aliphatic hydrocarbon group which may be straight or branched and comprising about 1 to about 6 carbon atoms in the chain. Branched means that one or more lower alkyl groups such as methyl, ethyl or propyl, are attached to a linear alkyl chain. Non-limiting examples of suitable alkyl groups include methyl, ethyl, n-propyl, isopropyl, n-butyl, t-butyl and n-pentyl.

Alkylene means a divalent alkyl chain, e.g., —CH₂CH₂— is ethylene.

Alkoxy means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

Halo means fluoro, chloro, bromo or iodo.

Aryl means a single aromatic carbocyclic ring or a bicyclic fused carbocyclic ring of 6 to 10 carbon atoms, for example phenyl or naphthyl.

Heteroaryl means a single ring heteroaromatic group of 5 to 6 atoms comprised of 2 to 5 carbon atoms and 1 to 3 heteroatoms independently selected from the group consisting of N, O and S, or a bicyclic heteroaromatic group of 5 to 10 atoms comprised of 1 to 9 carbon atoms and 1 to 3 heteroatoms independently selected from the group consisting of N, O and S, provided that the rings do not include adjacent oxygen and/or sulfur atoms. Examples of single-ring heteroaryl groups are pyridyl, oxazolyl, isoxazolyl, oxadiazolyl, furanyl, pyrrolyl, thienyl, imidazolyl, pyrazolyl, thiazolyl, isothiazolyl, thiadiazolyl, pyrazinyl, pyrimidyl, pyridazinyl and triazolyl. Examples of bicyclic heteroaryl groups are naphthyridyl (e.g., 1,5 or 1,7), imidazopyridyl, pyridopyrimidinyl and 7-azaindolyl. Also included in the definition of heteroaryl are benzofused heteroaryl groups comprising a heteroaryl ring as defined above fused at adjacent carbon atoms to a phenyl ring. Examples of benzofused heteroaryl groups are indolyl, quinolyl, isoquinolyl, phthalazinyl, benzothienyl (i.e., thionaphthenyl), benzimidazolyl, benzofuranyl, benzoxazolyl and benzofurazanyl. All positional isomers are contemplated, e.g., 2-pyridyl, 3-pyridyl and 4-pyridyl. N-oxides of the ring nitrogens for all heteroaryl groups are also included. $R^8$- and $R^{12}$-substituted heteroaryl refers to such groups wherein substitutable ring carbon atoms have a substituent as defined above.

Heteroaryldiyl means a heteroaryl ring bonded to two different groups. For example, in the context of this invention, when A is heteroaryldiyl, one ring member is attached to —NH— and another ring member is attached to X. As an example, a pyridinediyl ring is shown:

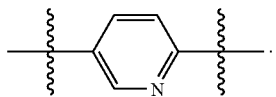

Arylene means a divalent aryl ring, that is, an aryl ring bonded to two different groups, e.g., phenylene.

Cycloalkyl means a non-aromatic mono- or multicyclic ring system comprising about 3 to about 10 carbon atoms. Preferred cycloalkyl rings contain about 3 to about 7 ring atoms. Non-limiting examples of suitable monocyclic cycloalkyls include cyclopropyl, cyclopentyl, cyclohexyl and the like. Non-limiting examples of suitable multicyclic cycloalkyls include 1-decalin, norbornyl, adamantyl and the like.

Cycloalkylene means a divalent cycloalkyl ring, that is, a cycloalkyl ring bonded to two different groups, e.g., 1,4-cyclohexylene,

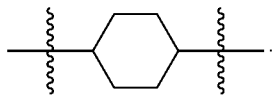

Heterocycloalkyl means a 3 to 6-membered saturated ring comprised of 2 to 5 carbon atoms and 1 or 2 heteroatoms selected from the group consisting of N, S and O, provided that two heteroatoms are not adjacent to each other. Typical heterocycloalkyl rings are piperidinyl, piperazinyl, morpholinyl, azetidinyl, pyrrolidinyl, tetrahydrothienyl, tetrahydrofuranyl, tetrahydropyranyl and thiomorpholinyl.

Azacycloalkyl refers to the 5-6 membered ring shown in the definition of $R^7$ by the structure

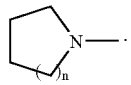

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quaternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

One or more compounds of the invention may also exist as, or optionally converted to, a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

Compounds of Formula I, and salts, solvates, esters and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

Polymorphic forms of the compounds of Formula I, and of the salts, solvates, esters and prodrugs of the compounds of Formula I, are intended to be included in the present invention.

"Patient" includes both human and animals.

"Mammal" means humans and other mammalian animals.

The term "purified", "in purified form" or "in isolated and purified form" for a compound refers to the physical state of said compound after being isolated from a synthetic process or natural source or combination thereof. Thus, the term "purified", "in purified form" or "in isolated and purified form" for a compound refers to the physical state of said compound after being obtained from a purification process or processes described herein or well known to the skilled artisan, in sufficient purity to be characterizable by standard analytical techniques described herein or well known to the skilled artisan.

Lines drawn into the ring systems, such as, for example:

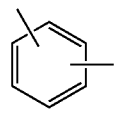

indicate that the indicated line (bond) may be attached to any of the substitutable ring carbon atoms.

As well known in the art, a bond drawn from a particular atom wherein no moiety is depicted at the terminal end of the bond indicates a methyl group bound through that bond to the atom, unless stated otherwise. For example:

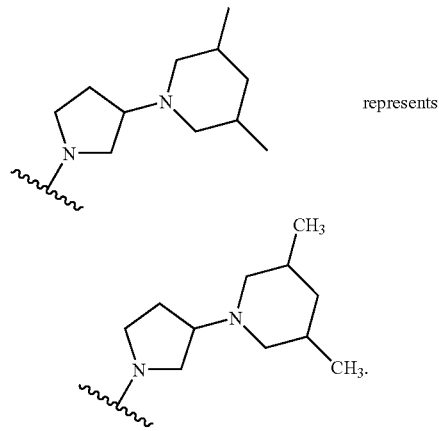

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, N.Y.

When any variable (e.g., aryl, heterocycle, $R^{14}$, etc.) occurs more than one time in any constituent or in Formula I, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of Formula I or a salt and/or solvate thereof. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

Compounds of formula I are prepared by general methods known in the art. Preferably, the compounds of formula I are prepared by the methods shown in the following reaction schemes. In the Schemes and examples that follow, the following abbreviations are used:

Ac acetyl
Boc tert-butoxycarbonyl
Bu butyl
$CDCl_3$ d-chloroform
DCE dichloroethane
DMF NN-dimethylformamide
DMAP 4-NN-dimethylaminopyridine
DMSO $d_6$-dimethylsulfoxide
DIPEA diisopropylethylamine
Dioxane 1,4-dioxane
Et ethyl
Ether diethyl ether
HATU N-[(dimethylamino)-1H-1,2,3-triazolo[4,5-b]pyridin-1-ylmethylene]-N-methylmethanaminium Hexafluorophosphate N-oxide
LCMS liquid chromatography mass spectrometry
Me methyl
NBS N-bromosuccinimide
NCS N-chlorosuccinimide
NMR nuclear magnetic resonance spectroscopy
$Pd(dppf)Cl_2CH_2Cl_2$ dichloro[1,1'-bis(diphenylphosphino)ferrocene]-palladium (II) dichloromethane adduct
PS-EDC polystyrene 1-(3-dimethylaminopropyl)-3-ethylcarbodiimide)
rt Room temperature (about 25° C.)
TEA triethylamine
TFA trifluoroacetic acid
TLC thin layer chromatography
THF tetrahydrofuran Where NMR data are presented, $^1H$ spectra were obtained on either a Varian Gemini-400BB, or Mercury-400BB and are reported as ppm (parts per million) downfield from $Me_4Si$ with number of protons, multiplicities (s=singlet, d=doublet, t=triplet, m=multiplet, br.=broad), and coupling constants in hertz. Where LCMS data are presented, analyses were performed using an Applied Biosystems API-100 mass spectrometer and Shimadzu SCL-10A LC column: Altech platinum C18, 3 micron, 33 mm×7 mm ID: gradient flow: 0 min-10% MeCN, 5 min-95% MeCN, 7 min-95% MeCN, 7.5 min-10% MeCN, 9 min-stop. The observed parent ion is given.

In general the compounds described in this invention can be prepared from chlorides of type 1 or dichlorides of type 2 (Scheme 1). Condensation of aminopyrazoles of type 3 with keto esters of type 4 gives pyrimidones of type 5 which can be converted to chlorides of type 1 by treatment with $POCl_3$. Dichlorides of type 2 are prepared in a similar manner from aminopyrazoles of type 3 and diethyl malonate 6. In Scheme 1, $R^{7a}$ is $R^7$ is alkyl, $R^{12}$-phenyl, $R^{12}$-heteroaryl or cycloalkyl.

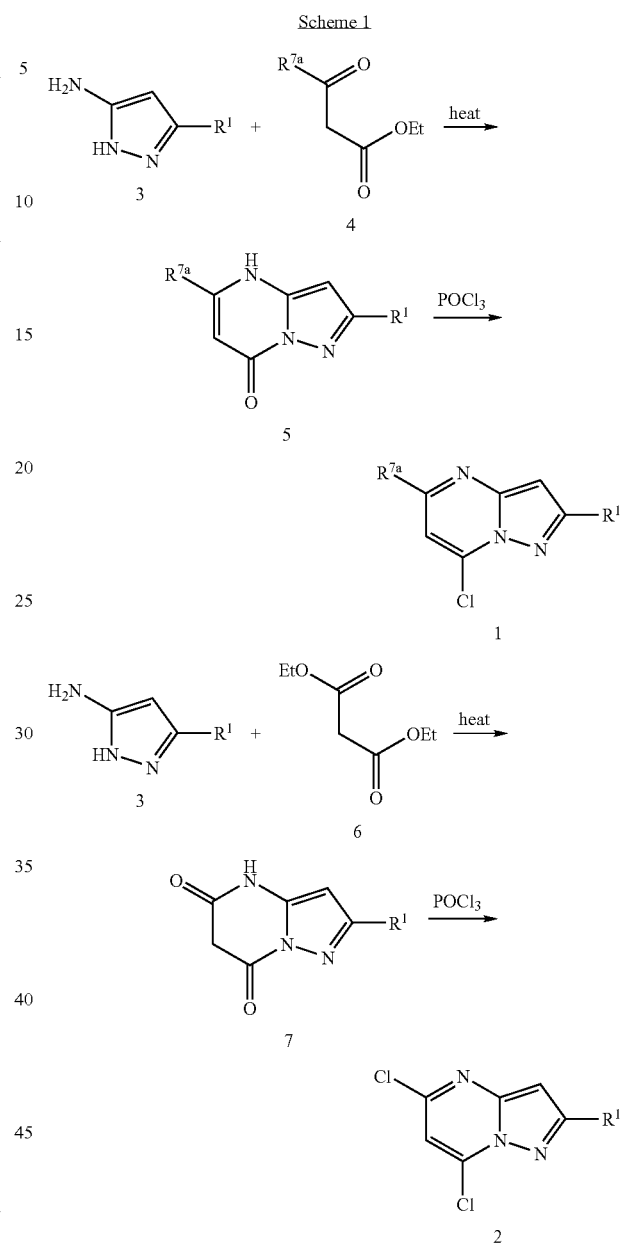

Incorporation of the 7-amino function can be achieved directly from the chlorides of type 1 and 2 by treatment with amines to give compounds of type 8 and type 9 (Scheme 2).

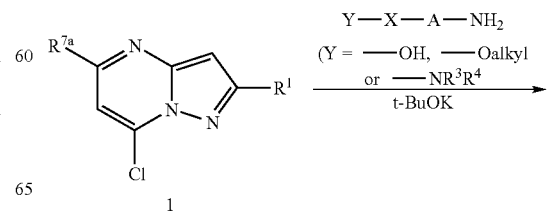

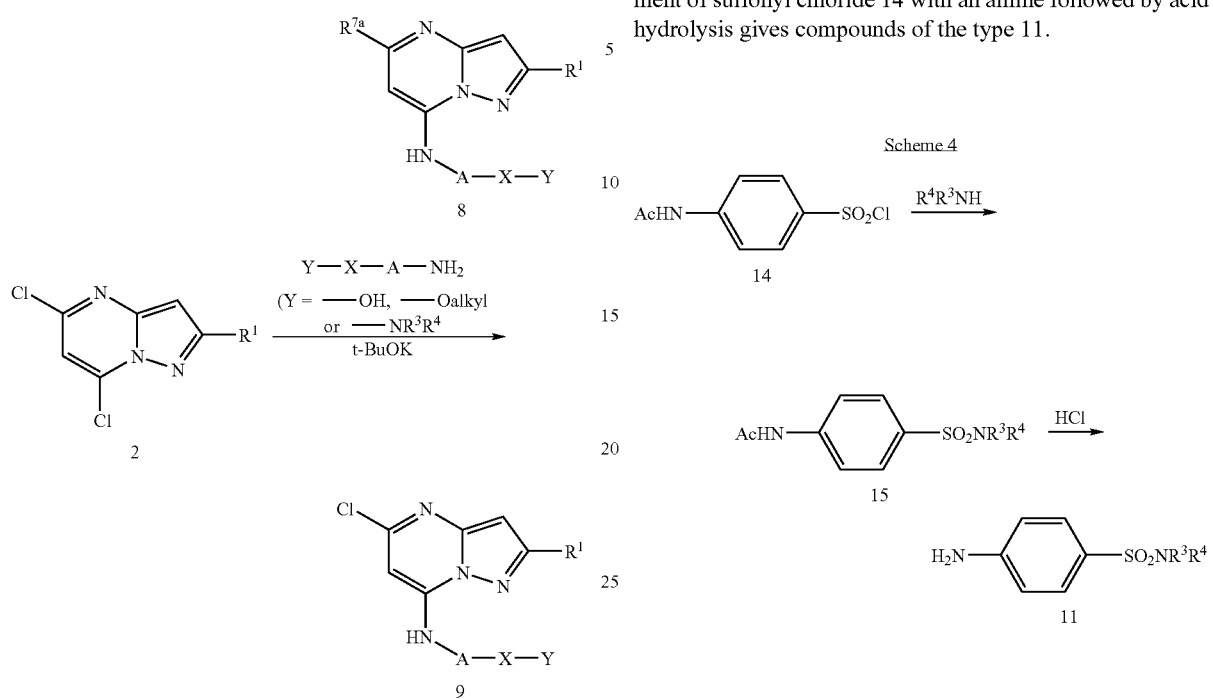

Compounds of the type 11 are either commercially available or synthesized in the manner shown in Scheme 4. Treatment of sulfonyl chloride 14 with an amine followed by acid hydrolysis gives compounds of the type 11.

Compounds of type 10 are prepared either by direct displacement with an aniline of type 11 or via the sulfonic acid of type 12 (Scheme 3).

Chlorides of type 17 can be protected as a carbamate 18, and converted to compounds of type 19 via a palladium catalyzed cross-coupling reaction; deprotection gives compounds of type 10a, wherein $R^{7a}$ is $R^{12}$-phenyl (Scheme 5).

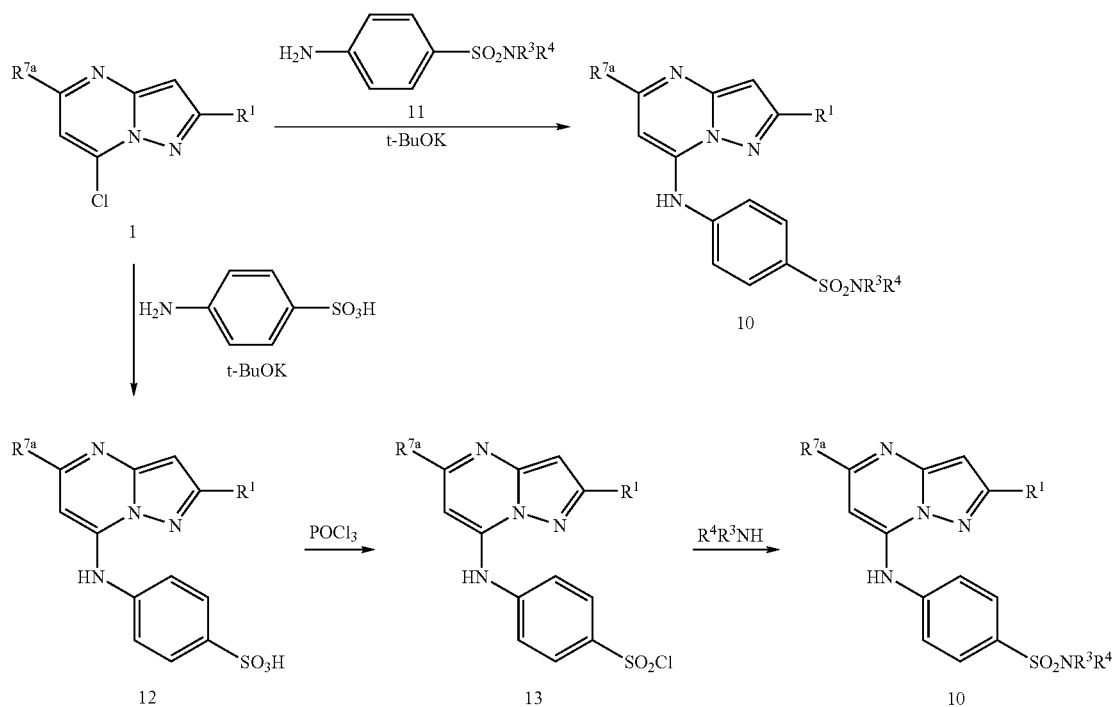

Scheme 5
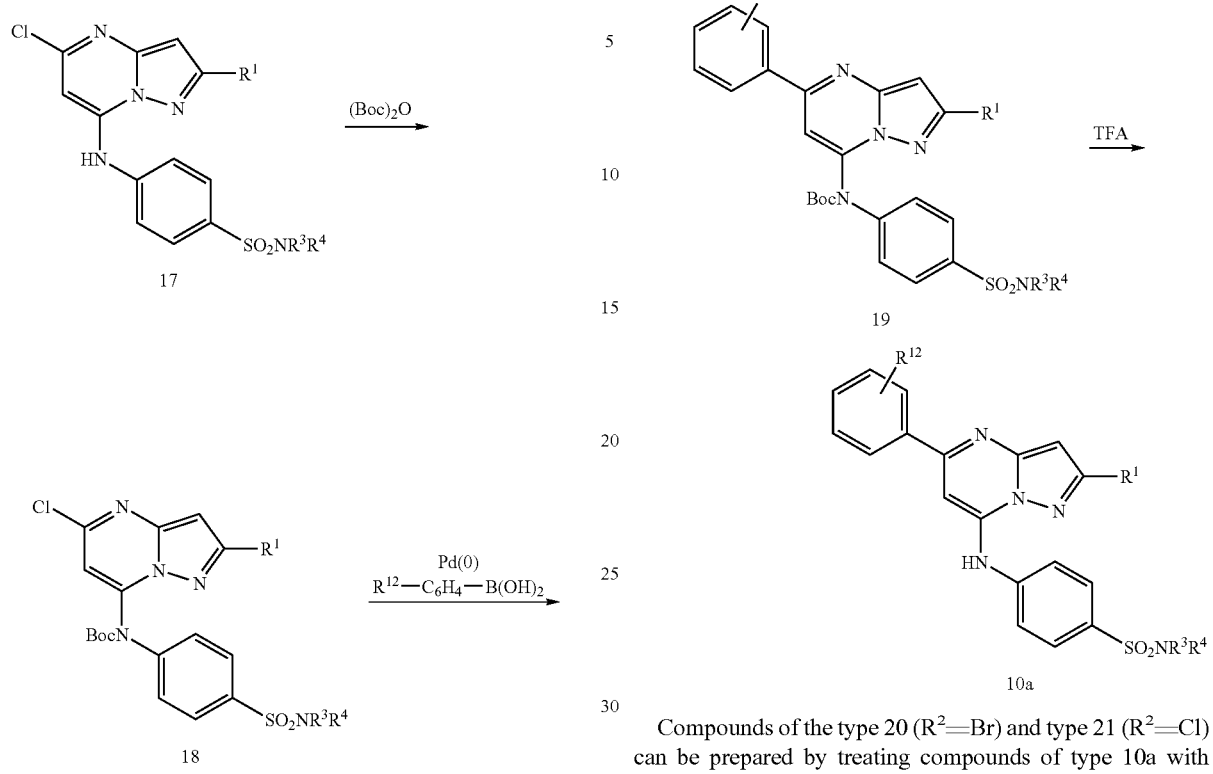
Compounds of the type 20 ($R^2$=Br) and type 21 ($R^2$=Cl) can be prepared by treating compounds of type 10a with electrophilic halogenating reagents such as NBS or NCS (Scheme 6).
Scheme 6
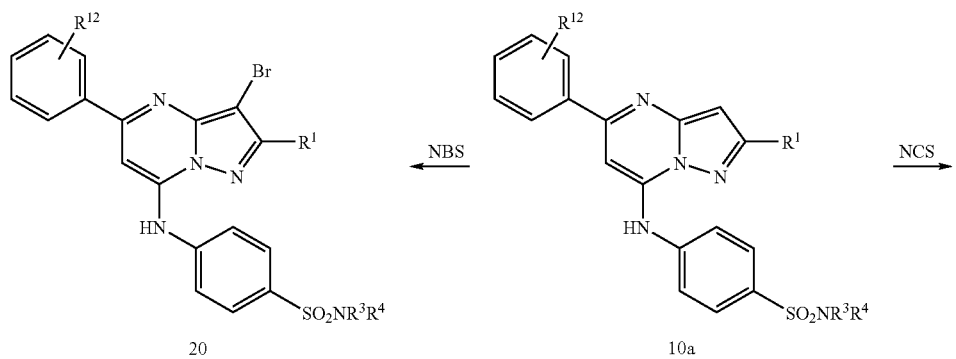
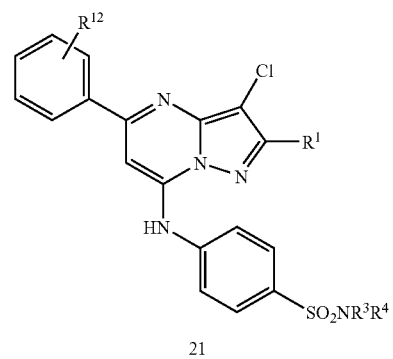

Compounds of type 22 and 23 are prepared as shown in Scheme 7. Compounds of type 17 can be halogenated in the same manner described in previous examples to give compounds of type 24. Compounds of types 17 and 24 can be treated with an amine to give compounds of type 23 and 22. In Scheme 7, $R^{7b}$ is optionally substituted piperazinyl or optionally substituted azacycloalkyl.

Compounds of type 25 ($R^2$=CN) are synthesized in the manner shown in Scheme 8. Malononitrile of type 26 can be condensed with hydrazine to give a pyrazole of type 27 which can be condensed with a keto ester type 4 to give pyrimidones of type 28. The pyrimidones are treated with $POCl_3$ to give chlorides of type 29. The 7-N amino functionality can be installed by reacting chlorides of type 29 with anilines of type 11.

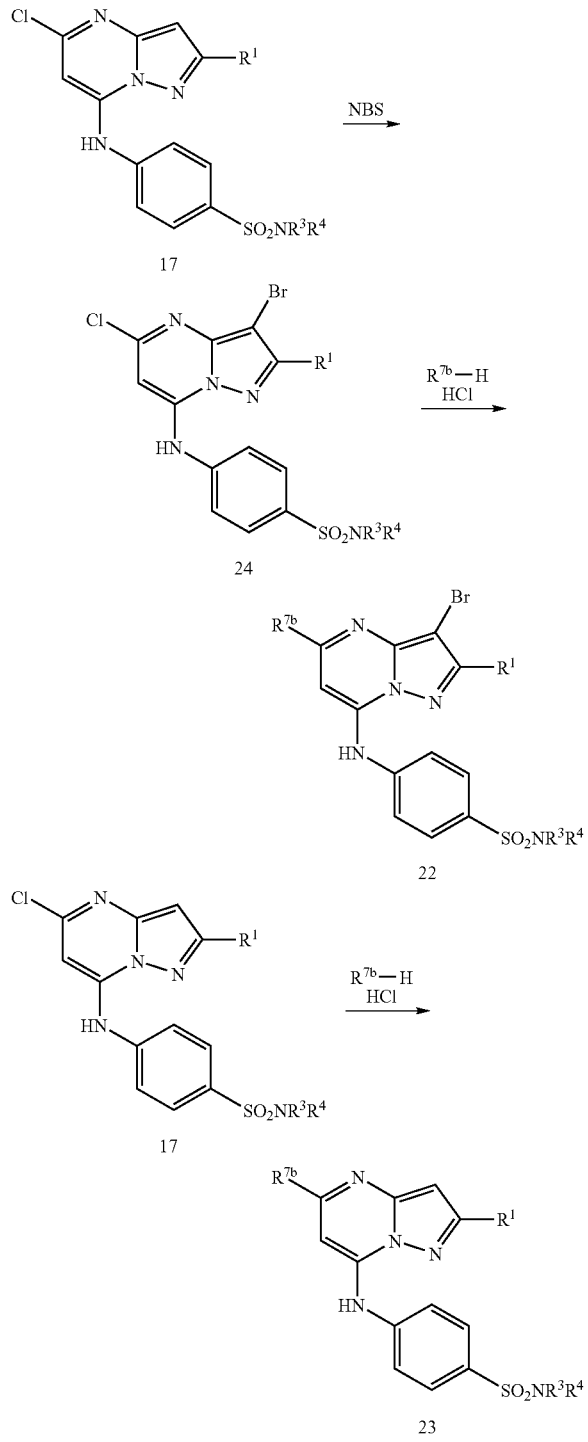

Compounds of type 31 can be prepared by treatment of acid of type 33 (which is available in 1 or 2 steps from chloride 1) with an amine under standard amide coupling conditions (Scheme 9).

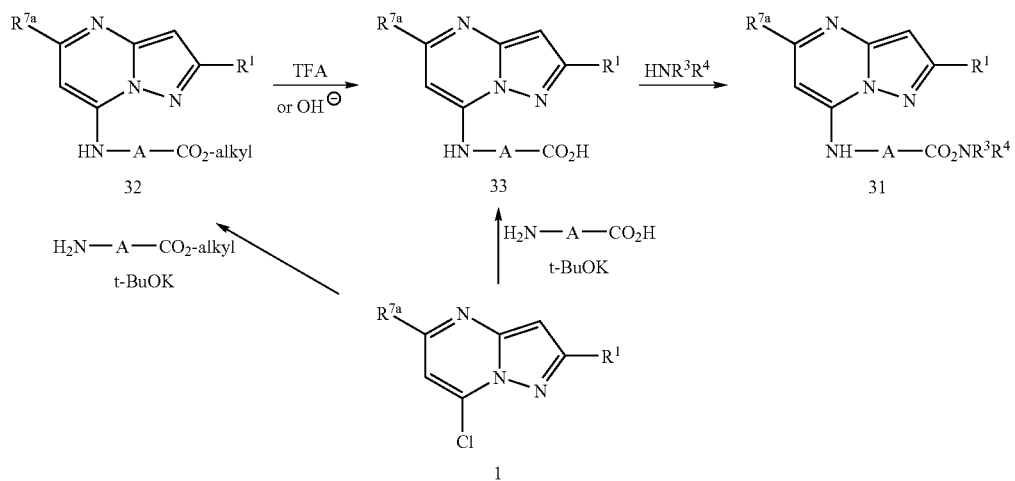

Compounds of the type 34 can be prepared by treating compounds of type 31a, wherein $R^{7a}$ is $R^{12}$-phenyl, with an electrophilic halogenating reagent such as NBS (Scheme 10).

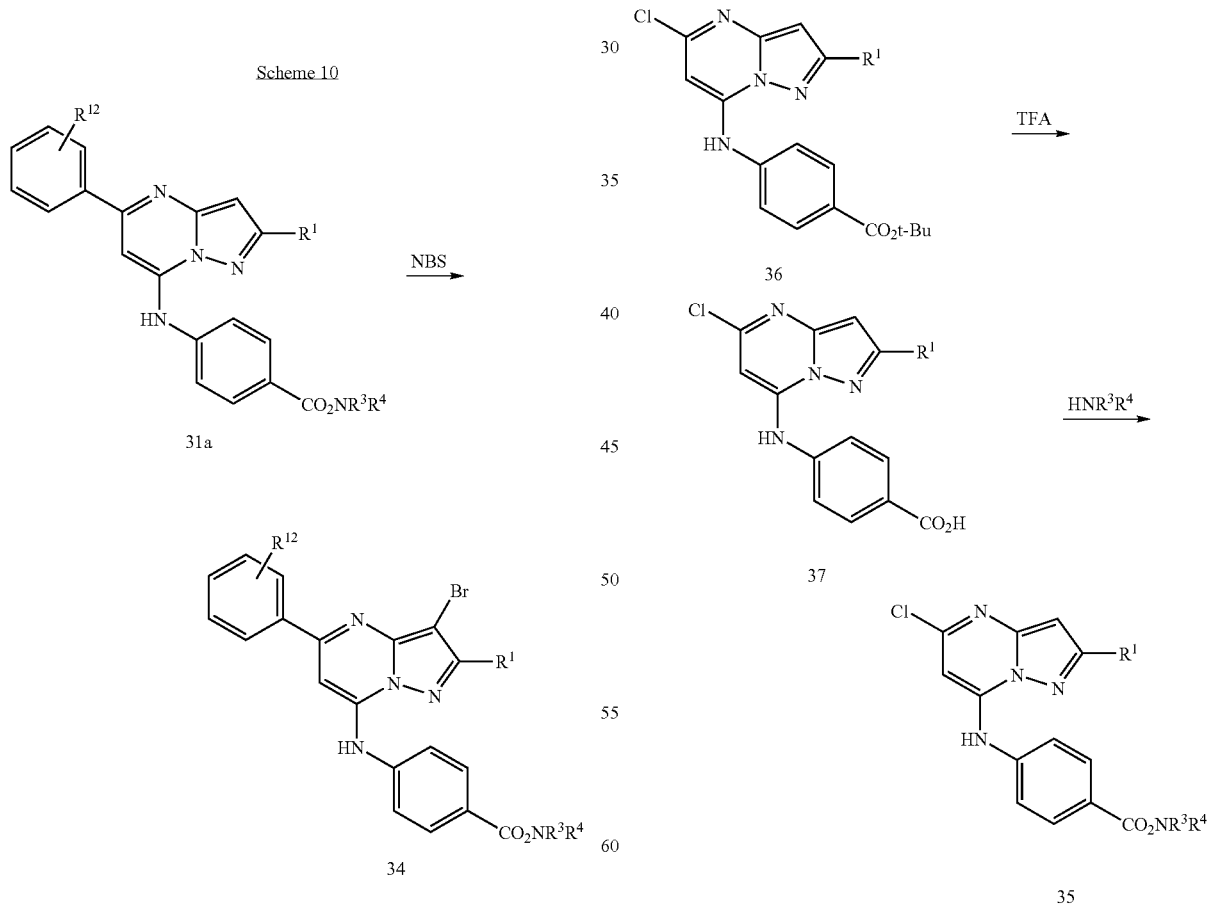

Compounds of type 35 can be prepared by treating the compounds of type 36 with TFA to give compounds of type 37 and then using standard amide formation to give compounds of type 35 (Scheme 11).

Compounds of type 38 can be synthesized by treatment of chloride type 35 with an amine $R^{7b}$—H in the presence of HCl (Scheme 12).

Scheme 12

[Structure 35: 2-chloro-pyrazolo[1,5-a]pyrimidine with R¹ and NH-phenyl-CO₂NR³R⁴ substituents]

R⁷ᵇ—H, HCl →

[Structure 38: pyrazolo[1,5-a]pyrimidine with R⁷ᵇ, R¹ and NH-phenyl-CO₂NR³R⁴ substituents]

The invention disclosed herein is exemplified by the following examples which should not be construed to limit the scope of the disclosure. Alternative mechanistic pathways and analogous structures will be apparent to those skilled in the art.

Preparation 1A

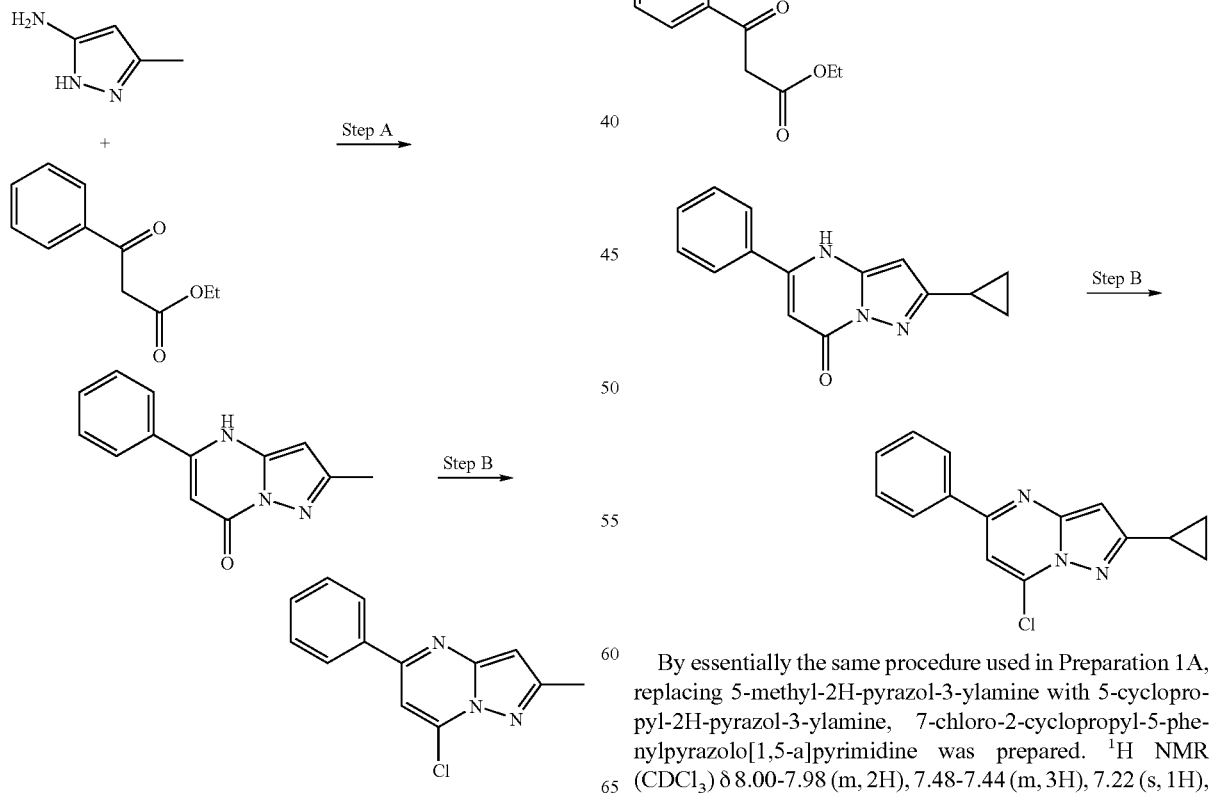

(prepared in a procedure analogous to that outlined in WO 2004/026229 A2)

Step A:

5-Methyl-2H-pyrazol-3-ylamine (1 g, 0.0103 mol) was suspended in AcOH (7 ml), 3-oxo-3-phenylpropionic acid ethyl ester (1.95 ml, 1.1 eq) was added and the mixture heated at reflux for 3 h. The mixture was cooled to rt and concentrated under reduced pressure. The residue was stirred with EtOAc and the solid collected by filtration to give 1.83 g of 2-methyl-5-phenyl-4H-pyrazolo[1,5-a]pyrimidin-7-one.

Step B:

The product of step A (1.83 g) was dissolved in POCl₃ (8.6 ml), pyridine (0.43 ml) was added and the mixture stirred for 3 days at rt. The resulting dark solution was diluted with Et₂O and filtered. The filtrate was cooled to 0° C. and quenched with water; once the quench was complete, additional water was added and the organic layer removed. The aqueous layer was further extracted with Et₂O, the combined organic layers were washed with NaHCO₃ (sat), dried (Na₂SO₄), and concentrated under reduced pressure to give 1.92 g of 7-chloro-2-methyl-5-phenylpyrazolo[1,5-a]pyrimidine which was used without further purification. LCMS: MH⁺=244.1.

Preparation 1B

By essentially the same procedure used in Preparation 1A, replacing 5-methyl-2H-pyrazol-3-ylamine with 5-cyclopropyl-2H-pyrazol-3-ylamine, 7-chloro-2-cyclopropyl-5-phenylpyrazolo[1,5-a]pyrimidine was prepared. ¹H NMR (CDCl₃) δ 8.00-7.98 (m, 2H), 7.48-7.44 (m, 3H), 7.22 (s, 1H), 6.35 (s, 1H), 2.17 (m, 1H), 1.10-1.05 (m, 2H), 0.93-0.89 (m, 2H).

Preparations 1C-1G

By essentially the same procedure as in Preparation 1A, substituting the compounds in column 1 as the keto-ester, the compounds in column 2 were prepared:

| Prep. | Column 1 | Column 2 | Data |
|---|---|---|---|
| 1C | 2-methoxyphenyl keto-ester (ethyl ester) | 5-(2-methoxyphenyl)-7-chloro-2-methylpyrazolo[1,5-a]pyrimidine | $^1$H NMR (DMSO) δ 7.75 (m, 1H), 7.61 (s, 1H), 7.45 (m, 1H), 7.15 (d, J=8 Hz, 1H), 7.04 (t, J=7.2 Hz, 1H), 6.65 (s, 1H), 3.83 (s, 3H), 2.42 (s, 3H) |
| 1D | 2-methylphenyl keto-ester (ethyl ester) | 5-(2-methylphenyl)-7-chloro-2-methylpyrazolo[1,5-a]pyrimidine | $^1$H NMR (CDCl$_3$) δ 7.46 (m, 1H), 7.39-7.25 (m, 3H), 7.03 (s, 1H), 6.6 (s, 1H), 2.6 (s, 3H), 2.43 (s, 3H). |
| 1E | 2-chlorophenyl keto-ester (methyl ester) | 5-(2-chlorophenyl)-7-chloro-2-methylpyrazolo[1,5-a]pyrimidine | $^1$H NMR (CDCl$_3$) δ 7.66 (m, 1H), 7.51 (m, 1H), 7.41 (m, 2H), 7.28 (s, 1H), 6.65 (s, 1H), 2.60 (s, 3H), |
| 1F | 4-(methoxycarbonyl)phenyl keto-ester (methyl ester) | 5-(4-(methoxycarbonyl)phenyl)-7-chloro-2-methylpyrazolo[1,5-a]pyrimidine | $^1$H NMR (CDCl$_3$) δ 8.19-8.14 (m, 4H), 7.38 (s, 1H), 6.65 (s, 1H), 3.96 (s, 3H), 2.30 (s, 3H) |
| 1G | cyclohexyl keto-ester (ethyl ester) | 5-cyclohexyl-7-chloro-2-methylpyrazolo[1,5-a]pyrimidine | $^1$H NMR (CDCl$_3$) δ 6.77 (s, 1H), 6.46 (s, 1H), 2.73 (m, 1H), 2.54 (s, 3H), 1.97 (m, 2H), 1.87 (m, 2H), 1.76 (m, 1H), 1.53 (m, 2H), 1.40 (m, 2H), 1.43-1.25 (m, 1H) |

Preparation 1H

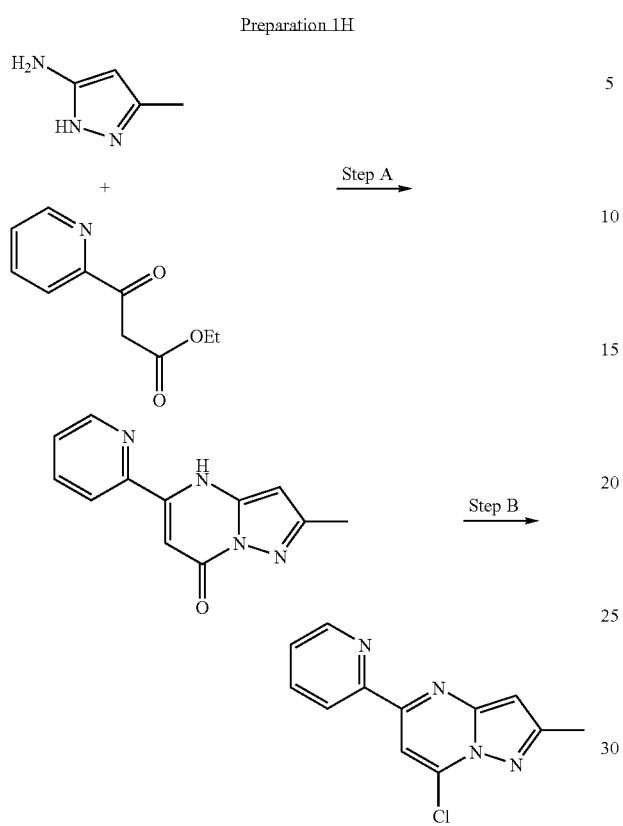

Step A:

(prepared according to an analogous procedure described in *Polish J. Chem.*, 56 (1982) p 963)

3-Oxo-3-(pyridin-2-yl)propionic acid ethyl ester (2 g, 0.01035 mol) and 5-methyl-2H-pyrazol-3-ylamine (1 g, 1 eq) were heated together at 140° C. for 2 h; after cooling to rt, the solid residue was stirred with EtOAc and the solid collected by filtration to give 1.84 g of 2-methyl-5-pyridin-2-yl-4H-pyrazolo[1,5-a]pyrimidin-7-one.

Step B:

The product of step A (1.84 g) was dissolved in POCl$_3$ (24 ml) and cooled to 0° C. N,N-dimethylaniline (3.1 ml, 3 eq) was added and the mixture heated at 60° C. for 16 h. The mixture was cooled to rt and the volatiles removed. The resulting residue was dissolved in CH$_2$Cl$_2$, poured onto ice, and taken to pH 8 with NaHCO$_3$ (s). The CH$_2$Cl$_2$ layer was removed, washed with water, and dried (MgSO$_4$). The mixture was concentrated under reduced pressure and the residue chromatographed (SiO$_2$, hexane-EtOAc/hexane 1:1) to give 1.2 g of the title compound. $^1$H NMR (CDCl$_3$) δ 8.71 (m, 1H), 8.49 (d, J=8.4 Hz, 1H), 8.14 (s, 1H), 7.87 (t, J=9.6 Hz, 1H), 7.41 (m, 1H), 6.64 (s, 1H), 2.60 (s, 3H).

Preparations 1I-1L

By essentially the same procedure set forth in Preparation 1H, substituting the compounds in columns 1 and 2, the compounds in column 3 were synthesized.

| Prep. | Column 1 | Column 2 | Column 3 | Data |
|---|---|---|---|---|
| 1I | | | | $^1$H NMR (CDCl$_3$) δ 8.80 (d, J= 5.2 Hz, 2H), 7.97 (d, J= 5.2 Hz, 2H), 7.37 (s, 1H), 6.69 (s, 1H), 2.61 (s, 3H). |
| 1J | | | | $^1$H NMR (CDCl$_3$) δ 8.79 (m, 2H), 7.94 (m, 2H), 7.34 (s, 1H), 6.49 (s, 1H), 2.23 (m, 1H), 1.14 (m, 2H), 0.97 (m, 2H). |
| 1K | | | | $^1$H NMR (CDCl$_3$) δ 9.19 (s, 1H), 8.67 (m, 1H), 8.33 (m, 1H), 7.40 (m, 1H), 7.20 (s, 1H), 6.38 (s, 1H), 2.17 (m, 1H), 1.09 (m, 2H), 0.91 (m, 2H). |

-continued

| Prep. | Column 1 | Column 2 | Column 3 | Data |
|---|---|---|---|---|
| 1L | 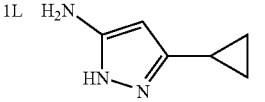 | 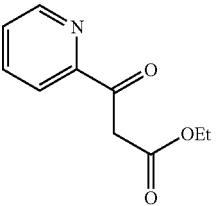 | 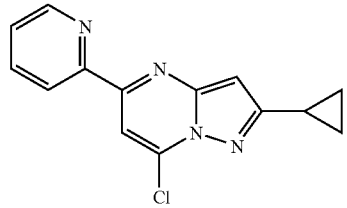 | LCMS: MH+ = 271.1. |

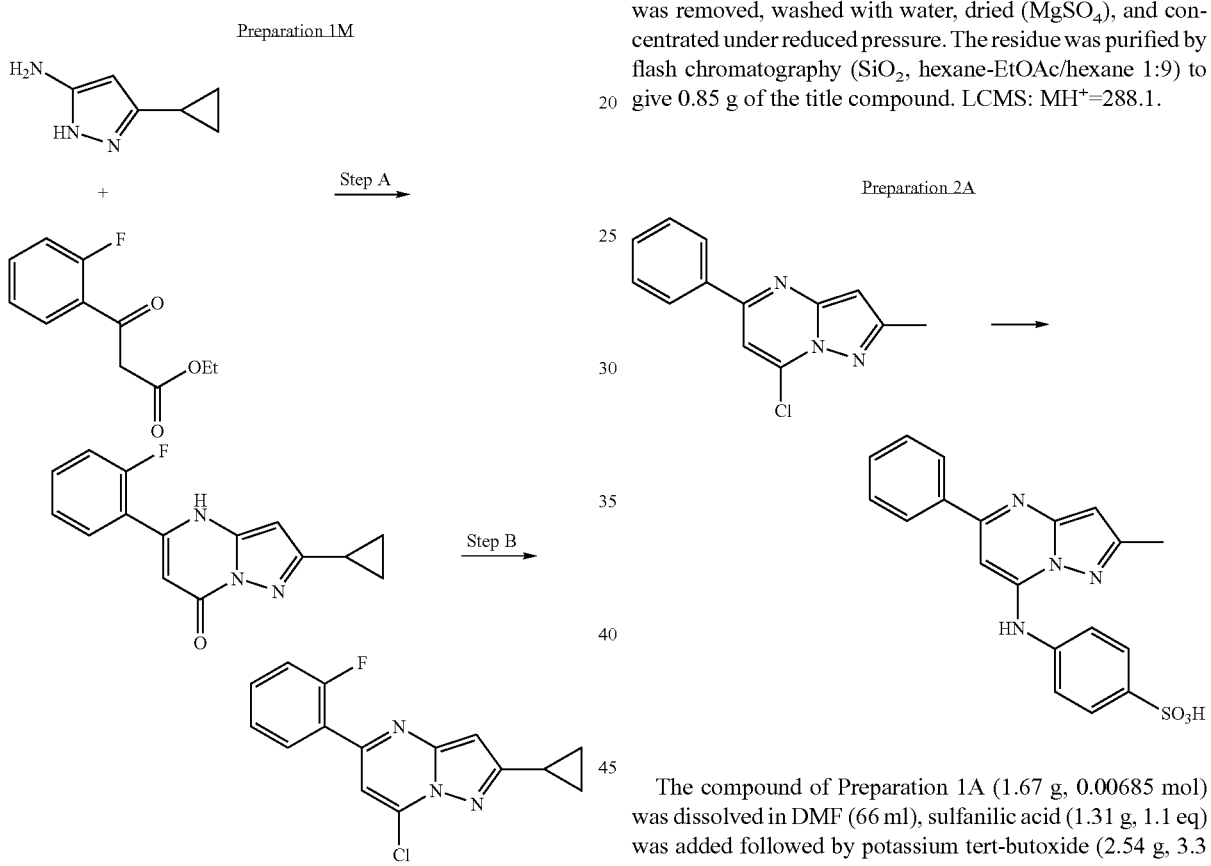

Preparation 1M

Step A:

5-Cyclopropyl-2H-pyrazol-3-ylamine (2.9 g, 0.0235 mol) was suspended in AcOH (18 ml), 3-(2-fluorophenyl)-3-oxo-propionic acid ethyl ester (4.67 ml, 1.1 eq) was added and the mixture heated at reflux for 3 h. The mixture was cooled to rt and concentrated under reduced pressure. The residue was stirred with EtOAc and the solid collected by filtration to give 2 g of 2-cyclopropyl-5-(2-fluorophenyl)-4H-pyrazolo[1,5-a]pyrimidin-7-one.

Step B:

The compound from step A (1 g, 0.00371 mol) was dissolved in POCl₃ (12 ml) and cooled to 0° C. N,N-dimethylaniline (1.4 ml, 3 eq) was added and the mixture heated at 80° C. for 16 h. The mixture was cooled to rt and the volatiles removed. The resulting residue was dissolved in CH₂Cl₂, poured onto ice, and taken to pH 8 with NaHCO₃ (s). The CH₂Cl₂ layer was removed, washed with water, dried (MgSO₄), and concentrated under reduced pressure. The residue was purified by flash chromatography (SiO₂, hexane-EtOAc/hexane 1:9) to give 0.85 g of the title compound. LCMS: MH+=288.1.

Preparation 2A

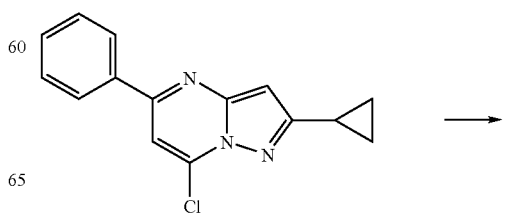

The compound of Preparation 1A (1.67 g, 0.00685 mol) was dissolved in DMF (66 ml), sulfanilic acid (1.31 g, 1.1 eq) was added followed by potassium tert-butoxide (2.54 g, 3.3 eq). After stirring for 16 h, the mixture was added to water (500 ml) and acidified to pH 3. The resultant precipitate was collected by filtration and dried overnight to give 2.17 g of the title compound. ¹H NMR (DMSO) δ 7.9 (m, 2H), 7.72 (d, J=8.8 Hz, 2H), 7.59-7.54 (m, 3H), 7.49 (d, J=8.8 Hz, 2H), 6.58 (s, 1H), 6.51 (s, 1H), 2.53 (s, 3H).

Preparation 2B

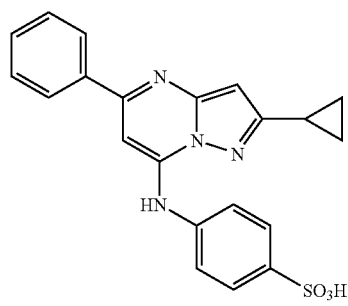

The compound of Preparation 1B (1.0 g, 0.0371 mol) was dissolved in DMF (30 ml), sulfanilic acid (1.4 g, 2.2 eq) was added followed by potassium tert-butoxide (2.74 g, 6.6 eq). After stirring for 16 h, the mixture was added to water and acidified to pH 3. The resultant precipitate was collected by filtration and dried overnight to give 1.25 g of the title compound. $^1$H NMR (DMSO) δ 7.87 (d, J=8.0 Hz, 2H), 7.82 (d, J=8.0 Hz, 2H), 7.59-7.54 (m, 3H), 7.49 (d, J=8.4 Hz, 2H), 6.54 (s, 1H), 6.36 (s, 1H), 2.21 (m, 1H), 1.11 (m, 2H), 0.99 (m, 2H).

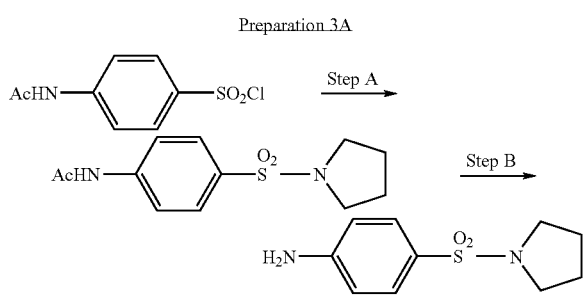

Preparation 3A (prepared according to an analogous procedure described in U.S. Pat. No. 5,755,873)

Step A:

Pyrrolidine (16 ml, 0.1925 mol) was dissolved in acetone (40 ml) and cooled to 0° C.; 4-acetylaminobenzenesulfonyl chloride (15 g, 0.065 mol) was added over 10 min. Additional acetone (13 ml) was added and the mixture was heated at reflux for 2 h. After cooling to rt, the mixture was added to water (350 ml) and the resulting precipitate collected by filtration, the precipitate was washed with water until the washings were at pH 7. The solid was dried under vacuum to give 8.1 g of N-[4-(pyrrolidine-1-sulfonyl)phenyl]acetamide.

Step B:

The compound from step A (8.1 g) was suspended in water (37.5 ml) and treated with concentrated HCl (19 ml). The mixture was heated at reflux for 1 h. After cooling to rt, NH$_4$OH (23 ml) was added with stirring. The resulting precipitate was collected by filtration and washed with water until the washings were pH 7. The solid was dried to give 6.0 g of 4-(pyrrolidine-1-sulfonyl)phenylamine. $^1$H NMR (DMSO) δ 7.40 (d, J=8.8 Hz, 2H), 6.62 (d, J=8.8 Hz, 2H), 6.02 (s, 2H), 3.03 (m, 4H), 1.61 (m, 4H).

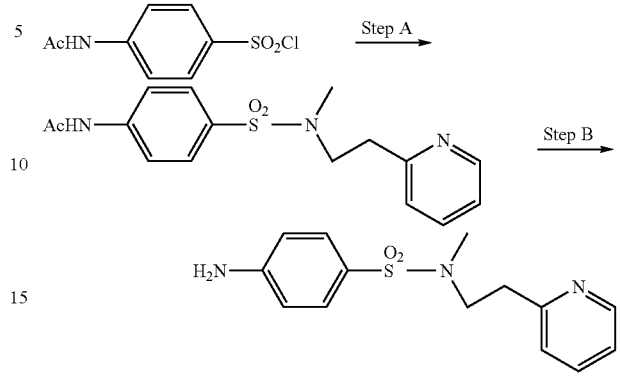

Preparation 3B (prepared according to an analogous procedure described in U.S. Pat. No. 5,755,873)

Step A:

Methyl-(2-pyridin-2-ylethyl)amine (8.9 ml, 0.0643 mol) was dissolved in acetone (13 ml) and cooled to 0° C., 4-acetylaminobenzenesulfonyl chloride (5 g, 0.0214 mol) was added over 10 min. Additional acetone (5 ml) was added and the mixture was heated at reflux for 2 h. After cooling to rt, the mixture was added to water and extracted with EtOAc. The extracts were dried (MgSO$_4$). The mixture was concentrated under reduced pressure and purified by flash chromatography (SiO$_2$, EtOAc-MeOH/EtOAc 1:19) to give 5.6 g of N-{4-[methyl-(2-pyridin-2-yl-ethyl)sulfamoyl]phenyl}acetamide.

Step B:

The compound from step A (5.6 g) was suspended in water (22.4 ml), treated with concentrated HCl (13.4 ml), and the mixture heated at reflux for 1 h. After cooling to rt, NH$_4$OH (13.7 ml) was added with stirring. The resulting mixture was extracted with CH$_2$Cl$_2$; the extracts were washed with water, dried (MgSO$_4$), and concentrated under reduced pressure to give 4.8 g of 4-amino-N-methyl-N-(2-pyridin-2-ylethyl)benzenesulfonamide. LCMS: MH$^+$=292.0.

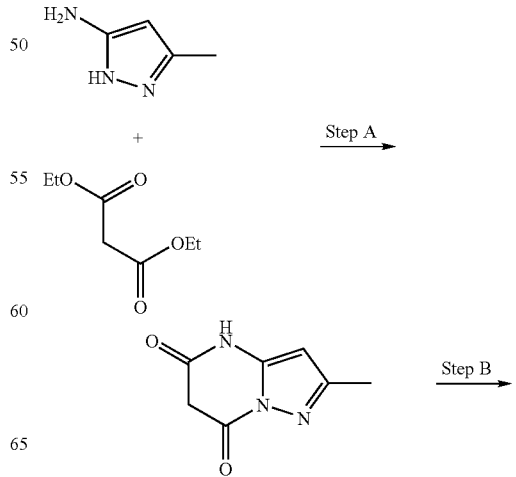

Preparation 4A

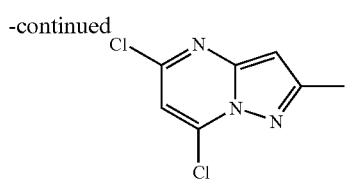

(prepared in an analogous procedure to that outlined in WO 2004/026229 A2)

Step A:

5-Methyl-2H-pyrazol-3-ylamine (2 g, 0.0206 mol) was dissolved in EtOH (60 ml) and NaOEt (11.58 ml of a 21% by wt. solution, 2 eq) was added, followed by diethyl malonate (3.44 ml, 1.1 eq). The mixture was heated at reflux for 3 h. After cooling to rt, the precipitate was collected by filtration, washed with additional EtOH, and dried to give 1.6 g of 2-methyl-4H-pyrazolo[1,5-a]pyrimidine-5,7-dione.

Step B:

The compound from step A (1.6 g) was dissolved in POCl$_3$ (18 ml) and cooled to 0° C., N,N-dimethylaniline (3.43 ml) was added and the mixture heated at 115-120° C. overnight. After cooling to rt, the POCl$_3$ was removed under reduced pressure, the resulting residue was taken up in CH$_2$Cl$_2$, and poured onto ice. Once the ice melted the mixture was neutralized with NaHCO$_3$ (s) and the organic layer separated. The organic layer was washed with water, dried (MgSO$_4$), concentrated under reduced pressure, and the resulting residue purified by flash chromatography (SiO$_2$, hexane-CH$_2$Cl$_2$) to give 0.734 g of 5,7-dichloro-2-methylpyrazolo[1,5-a]pyrimidine. $^1$H NMR (CDCl$_3$) δ 6.89 (s, 1H), 6.52 (s, 1H), 2.55 (s, 3H).

Preparation 4B

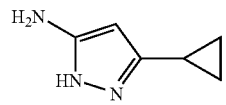

+

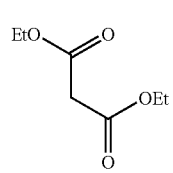

Step A →

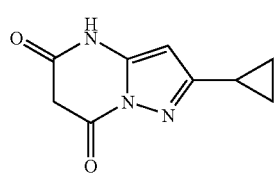

Step B →

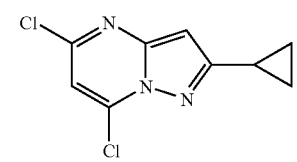

Employing essentially the same procedure as in Preparation 4A, using 5-cyclopropyl-2H-pyrazol-3-ylamine and diethyl malonate, 5,7-dichloro-2-cyclopropylpyrazolo[1,5-a]pyrimidine was obtained. $^1$H NMR (CDCl$_3$) δ 6.85 (s, 1H), 6.31 (s, 1H), 2.17 (m, 1H), 1.13 (m, 2H), 0.93 (m, 2H).

Preparation 5A

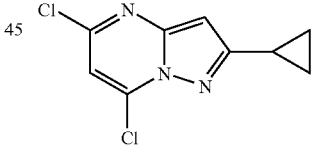

The compound of Preparation 4A (734 mg, 0.00364 mol) was dissolved in DMF (16 ml), and 4-amino-N,N-dimethylbenzenesulfonamide (800 mg, 1.1 eq) was added, followed by potassium tert-butoxide (816 mg, 2 eq). The mixture was stirred overnight. Water was added, the mixture extracted with EtOAc, and the extracts were dried (MgSO$_4$). The extracts were concentrated under reduced pressure and the residue purified by flash chromatography (SiO$_2$, Hexane-EtOAc/hexane 35:65) to give 900 mg of the title compound. $^1$H NMR (CDCl$_3$) δ 7.89 (d, J=8.8 Hz, 2H), 7.52 (d, J=8 Hz, 2H), 6.45 (s, 1H), 6.35 (s, 1H), 2.78 (s, 6H), 2.51 (s, 3H).

Preparation 5B

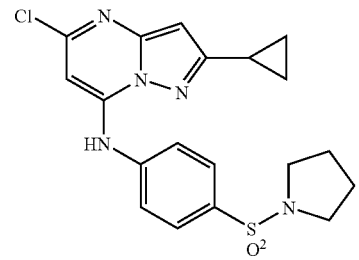

Employing essentially the same procedure as in Preparation 5A, using the product of Preparation 3A and the product of Preparation 4B, the title compound was prepared. LCMS: MH$^+$=418.2.

Preparation 5C

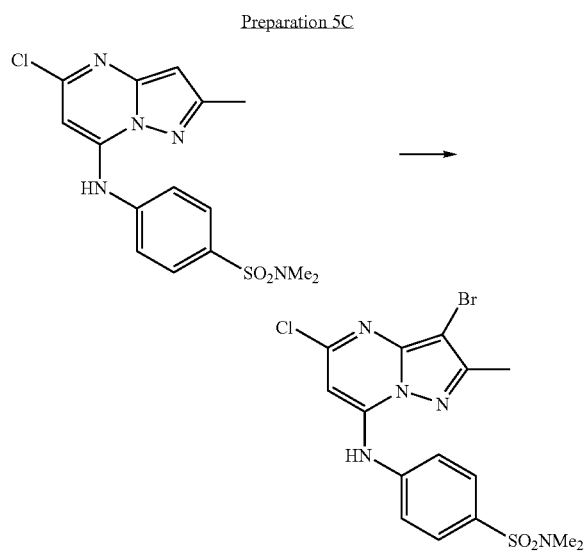

The product of Preparation 5A (588 mg, 0.00161 mol) was dissolved in THF (17.6 ml) and NBS (288 mg, 1 eq) was added. After 5 min, TLC showed the reaction was complete and the mixture was concentrated under reduced pressure. The residue was purified by flash chromatography (SiO$_2$, Hexane-EtOAc) to give the title compound (621 mg). $^1$H NMR (DMSO) δ 7.82 (d, J=8.8 Hz, 2H), 7.72 (d, J=8 Hz, 2H), 6.51 (s, 1H), 2.65 (s, 6H), 2.47 (s, 3H).

Compounds of Preparations 5A, 5B and 5C are also compounds of formula I.

Preparation 6

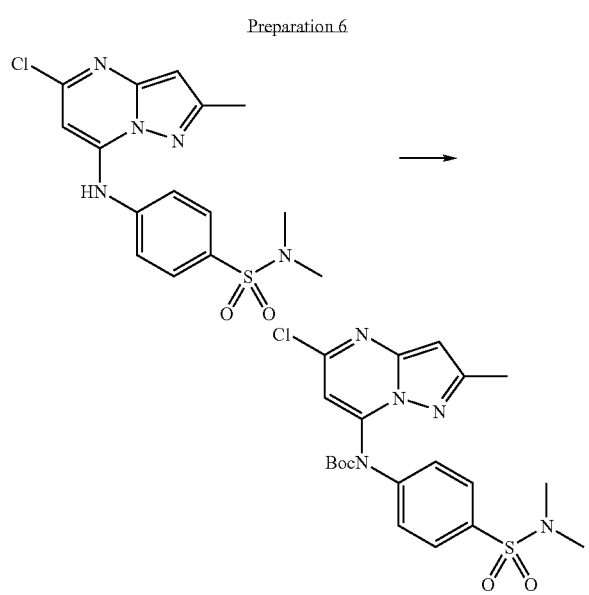

The compound of Preparation 5A (746 mg, 0.00204 mol) was dissolved in dioxane (10 ml) and tert-butyl dicarbonate (667 mg, 1.5 eq), then DMAP (247 mg, 1 eq) were added. After 10 min, additional dioxane (10 ml) was added and the mixture left stirring overnight. NaHCO$_3$ (sat) was added and the mixture extracted with EtOAc, the extracts were dried (MgSO$_4$), concentrated under reduced pressure, and the resulting residue purified by flash chromatography (SiO$_2$, hexane-EtOAc/hexane 1:1) to give 0.742 g of the title compound. LCMS: MH$^+$=466.3.

Preparation 7A

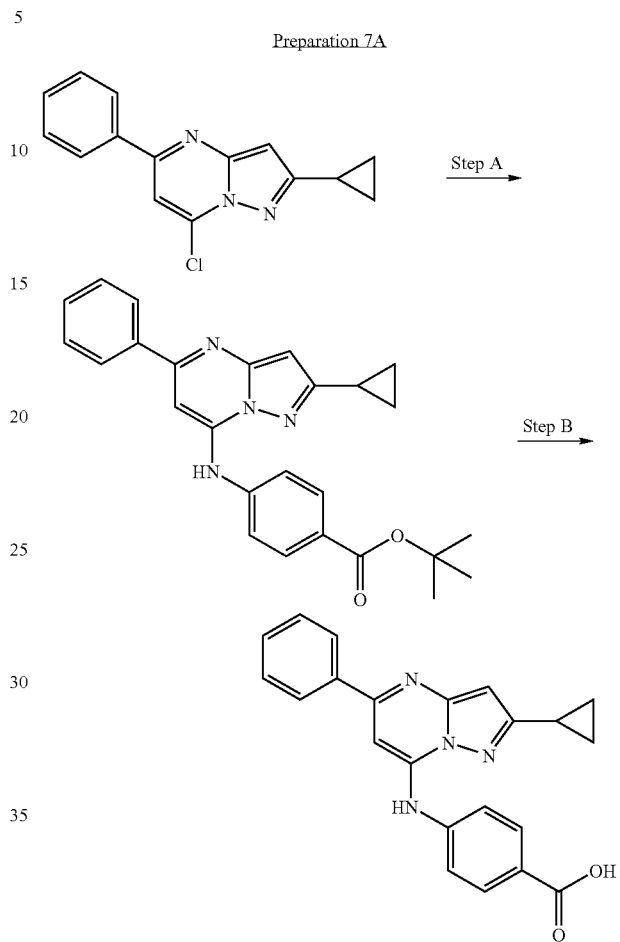

Step A:

The product of Preparation 1B (0.1 g, 0.000371 mol) was dissolved in N,N-dimethylacetamide (2 ml), 4-aminobenzoic acid tert-butyl ester (79 mg, 1.1 eq) was added, followed by potassium tert-butoxide (91 mg, 2.2 eq). The mixture was allowed to stir overnight. Water was added and the mixture extracted with EtOAc, the combined extracts were washed with water, brine, dried (MgSO$_4$), and concentrated under reduced pressure. The residue was purified by flash chromatography (SiO$_2$, hexane-EtOAc 1:4) to give 117 mg of 4-(2-cyclopropyl-5-phenylpyrazolo[1,5-a]pyrimidin-7-ylamino)benzoic acid tert-butyl ester. LCMS: MH$^+$=427.2.

Step B:

The compound from step A (117 mg) was dissolved in CH$_2$Cl$_2$ (16 ml), water (0.156 ml), then TFA (1.56 ml) was added, and the mixture allowed to stir overnight. Complete removal of volatiles under reduced pressure gave 110 mg of the title compound. LCMS: MH$^+$=371.2.

Preparations 7B-7F

Using essentially the same procedure set forth in Preparation 7A, substituting the chlorides in column 1, the compounds in column 2 were prepared.

| Prep. | Column 1 | Column 2 | Data |
|---|---|---|---|
| 7B | [5,7-dichloro-2-methylpyrazolo[1,5-a]pyrimidine] | [5-chloro-2-methyl-7-(4-carboxyphenylamino)pyrazolo[1,5-a]pyrimidine] | ¹H NMR (DMSO) δ 8.0 (d, J=8 Hz, 2H), 7.59 (d, J=8 Hz, 2H), 6.37 (s, 1H), 6.13 (s, 1H), 2.47 (s, 3H), |
| 7C | [7-chloro-2-cyclopropyl-5-(pyridin-2-yl)pyrazolo[1,5-a]pyrimidine] | [2-cyclopropyl-5-(pyridin-2-yl)-7-(4-carboxyphenylamino)pyrazolo[1,5-a]pyrimidine] | ¹H NMR (DMSO) δ 8.67 (d, J=4.4 Hz, 1H), 8.42 (d, J=8 Hz, 1H), 8.05 (d, J=8.8 Hz, 2H), 8.00 (m, 1H), 7.64 (d, J=8 Hz, 2H), 7.52 (m, 1H), 7.45 (s, 1H), 6.38 (s, 1H), 2.18 (m, 1H), 1.07 (m, 2H), 0.95 (m, 2H). |
| 7D | [7-chloro-2-cyclopropyl-5-(pyridin-3-yl)pyrazolo[1,5-a]pyrimidine] | [2-cyclopropyl-5-(pyridin-3-yl)-7-(4-carboxyphenylamino)pyrazolo[1,5-a]pyrimidine] | ¹H NMR (DMSO) δ 10.2 (m, 1H), 9.26 (br. s, 1H), 8.71 (br. s, 1H), 8.59 (d, J=8 Hz, 1H), 7.96 (d, J=8.4 Hz, 2H), 7.64 (m, 3H), 6.97 (s, 1H), 6.32 (s, 1H), 2.11 (m, 1H), 1.01 (m, 2H), 0.87 (m, 2H). |
| 7E | [7-chloro-2-cyclopropyl-5-(pyridin-4-yl)pyrazolo[1,5-a]pyrimidine] | [2-cyclopropyl-5-(pyridin-4-yl)-7-(4-carboxyphenylamino)pyrazolo[1,5-a]pyrimidine] | LCMS: MH⁺ = 372.1 |

-continued

| Prep. | Column 1 | Column 2 | Data |
|---|---|---|---|
| 7F | 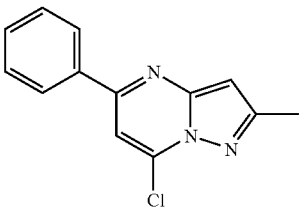 | | LCMS: MH+ = 345.1 |

Preparation 7G

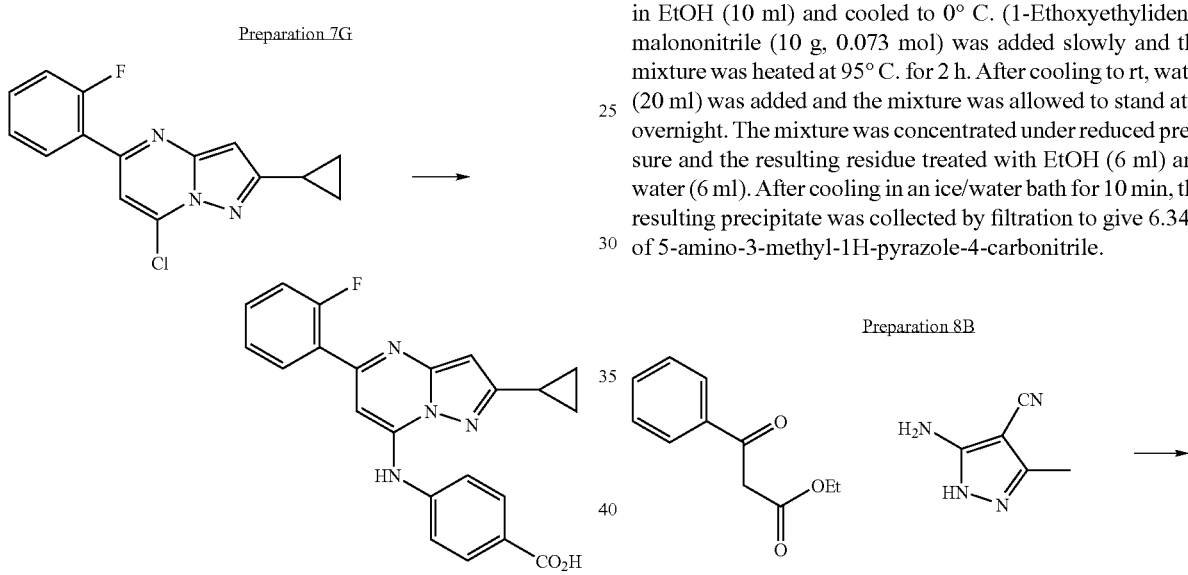

The product of Preparation 1M (250 mg, 0.000869 mol) was dissolved in DMF (4 ml), p-aminobenzoic acid (131 mg, 1.1 eq) was added followed by potassium tert-butoxide (293 mg, 3 eq). The mixture was stirred at rt for 24 h. HCl in dioxane (2 eq) was added, followed by water. The resulting solid was collected by filtration then purified by HPLC (C18, MeCN/H$_2$O/HCO$_2$H 5:95:0.1-95:5:0.1) to give 50 mg of the title compound. $^1$H NMR (DMSO) δ 7.98 (m, 3H), 7.62 (d, J=8.8 Hz, 2H), 7.49 (m, 1H), 7.31 (m, 2H), 6.84 (s, 1H), 6.34 (s, 1H), 2.17 (m, 1H), 1.06 (m, 2H), 0.92 (m, 2H).

Preparation 8A

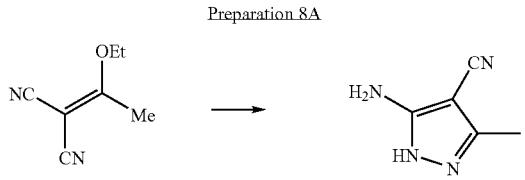

(prepared according the procedure in: *J. Org. Chem.*, 21, 1956, p 1240.)

Hydrazine monohydrate (6.8 ml, 0.14 mol) was dissolved in EtOH (10 ml) and cooled to 0° C. (1-Ethoxyethylidene)malononitrile (10 g, 0.073 mol) was added slowly and the mixture was heated at 95° C. for 2 h. After cooling to rt, water (20 ml) was added and the mixture was allowed to stand at rt overnight. The mixture was concentrated under reduced pressure and the resulting residue treated with EtOH (6 ml) and water (6 ml). After cooling in an ice/water bath for 10 min, the resulting precipitate was collected by filtration to give 6.34 g of 5-amino-3-methyl-1H-pyrazole-4-carbonitrile.

Preparation 8B

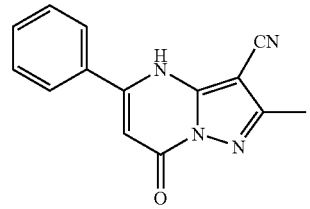

The product of Preparation 8A (2.0 g, 0.0164 mol) was dissolved in AcOH (10 ml). Ethyl benzoylacetate (3.2 ml, 0.018 mol) was added and the mixture heated at reflux for 4 h. After cooling to rt, the reaction mixture was concentrated under reduced pressure to give an off-white solid. EtOAc was added and the resulting solid collected by filtration to give 2.24 g of 2-methyl-7-oxo-5-phenyl-4,7-dihydropyrazolo[1,5-a]pyrimidine-3-carbonitrile. LCMS: MH+=251.1.

Preparation 8C

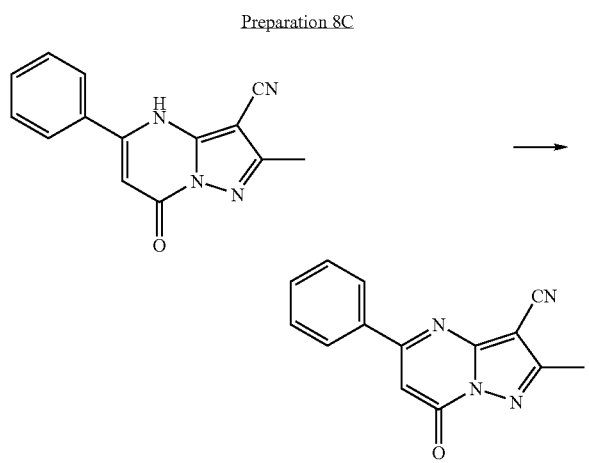

The product of Preparation 8B (0.6 g, 0.0024 mol) was suspended in POCl₃ (12 ml) and heated at 110° C. for 70 min. After cooling to rt, the mixture was concentrated under reduced pressure to give a solid residue which was treated with ice-cold water, NH₄OH was then added until the solution reached a pH of 11-12. The resulting solid was collected by filtration, washed with water to give 0.568 g of 7-chloro-2-methyl-5-phenylpyrazolo[1,5-a]pyrimidine-3-carbonitrile. LCMS: MH⁺=269.1.

Preparation 9A

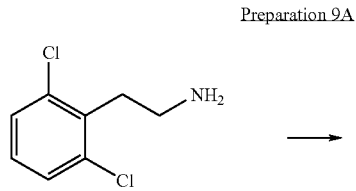

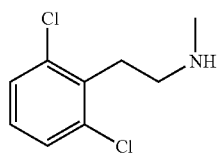

2-(2,6-Dichlorophenyl)ethylamine (1 ml, 0.00663 mol) and TEA (1.4 ml, 1.5 eq) were dissolved in THF (20 ml) and cooled in an ice-water bath. Ethyl chloroformate (0.95 ml, 1.5 eq) was added slowly and the mixture stirred at rt for 2 h. NH₄Cl (sat) was added and the mixture extracted with EtOAc, the combined extracts were washed with NH₄Cl (sat), and dried (MgSO₄). The organic solvent was removed and the residue dissolved in Et₂O (5 ml). This solution was slowly added to a slurry of LiAlH₄ (530 mg, 2 eq) in Et₂O (15 ml) at −78° C. The mixture was allowed to slowly warm to rt and stirred overnight. The mixture was cooled in an ice-water bath and water (0.53 ml), 15% NaOH (0.53 ml), and water (1.5 ml) added sequentially. The mixture was stirred vigorously for 30 min and the resulting slurry filtered. The filtrate was concentrated under reduced pressure to give 1.2 g of [2-(2,6-dichlorophenyl)ethyl]methylamine.

Preparations 9B-9G

By essentially the same procedure set forth in Preparation 9A, substituting the amines in column 1, the compounds shown in column 2 were prepared.

| Prep. | Column 1 | Column 2 |
|---|---|---|
| 9B | 4-F-C₆H₄-CH₂CH₂-NH₂ | 4-F-C₆H₄-CH₂CH₂-NHCH₃ |
| 9C | 3-F-C₆H₄-CH₂CH₂-NH₂ | 3-F-C₆H₄-CH₂CH₂-NHCH₃ |
| 9D | 2-Cl-6-F-C₆H₃-CH₂CH₂-NH₂ | 2-Cl-6-F-C₆H₃-CH₂CH₂-NHCH₃ |

| Prep. | Column 1 | Column 2 |
|---|---|---|
| 9E | 2,4-dichlorophenethylamine | N-methyl-2,4-dichlorophenethylamine |
| 9F | 2-chlorophenethylamine | N-methyl-2-chlorophenethylamine |
| 9G | 2-fluorophenethylamine | N-methyl-2-fluorophenethylamine |

Preparation 10A

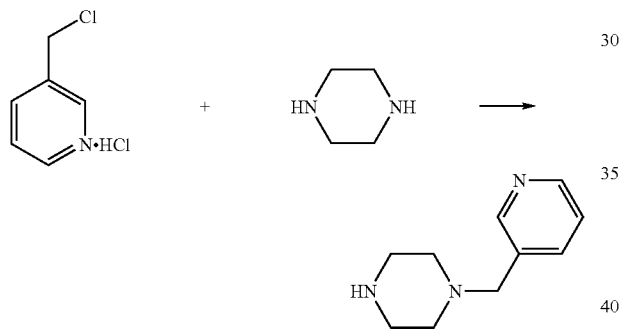

The title compound was prepared in an analogous manner to the procedure in *J. Med. Chem.*, 36, (1993), p 2984-2997.

Piperazine (1.42 g, 0.0165 mol) was dissolved in water (8 ml), 1 N HCl (16.5 ml, 0.0165 mol) was added and the mixture stirred for 30 min. 3-Chloromethyl-pyridine hydrochloride (1.35 g, 0.00823 mol) was added and the mixture stirred for 16 h. The mixture was extracted with EtOAc and the remaining aqueous layer basified to pH 10. The aqueous layer was first extracted with CH₂Cl₂, then CHCl₃. The CHCl₃ layer was dried and concentrated under vacuum to give 250 mg of the title compound.

By essentially the same procedure set forth in example 10A, only substituting the pyridine hydrochlorides in column 1, the compounds shown in column 2 were prepared.

| Prep. | Column 1 | Column 2 |
|---|---|---|
| 10B | 2-(chloromethyl)pyridine·HCl | 1-(pyridin-2-ylmethyl)piperazine |
| 10C | 4-(chloromethyl)pyridine·HCl | 1-(pyridin-4-ylmethyl)piperazine |

Preparation 11

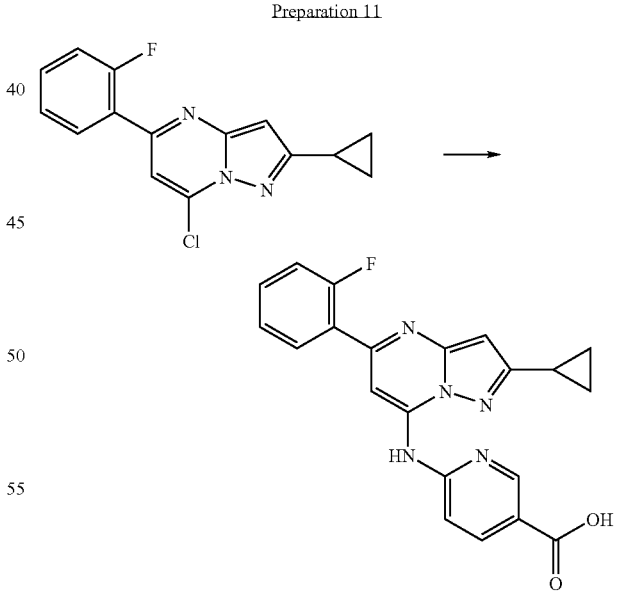

Preparation 1M (0.822 g, 0.00285 mol) was dissolved in N,N-dimethylacetamide (16 ml), 6-amino nicotinic acid methyl ester (476 mg, 1.1 eq) was added and the mixture cooled in an ice-water bath. t-BuOK (0.707 g, 2.2 eq) was added and the mixture was stirred overnight at rt. NH₄Cl (sat) was added and the resultant precipitate collected to give 1.075 g of a white solid which was dissolved in a 1:1 mixture of THF/CH₃OH (36 ml). 15% NaOH (18 ml) was added and the mixture stirred for 150 min. The mixture was acidified to pH 1 and the resulting solid collected to give 0.85 g of the title compound. LCMS MH$^+$=390.1

Preparation 12A

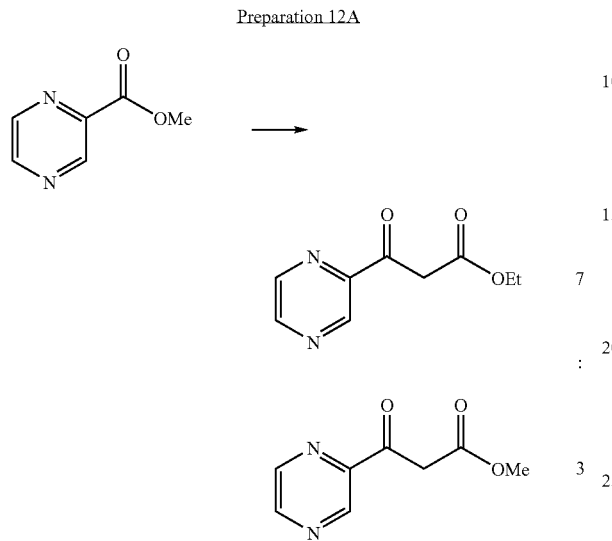

The title compounds were prepared according to the procedure outlined in JP 06172326.

A mixture of 25% (wt) solution of NaOCH₃ in CH₃OH (10.4 ml, 0.051 mol) and toluene (36 ml) was heated at 110° C. while a solution of 2-methoxycarbonylpyrazine (4 g, 0.0289 mol) in EtOAc (45 ml) was added dropwise. The mixture was heated for an additional 3 h and then cooled to rt. The solid precipitate was collected by filtration. The solid was dissolved in NH₄Cl (sat) and the mixture extracted with EtOAc. The organic extracts were dried and concentrated under vacuum to give 4.3 g of the title compounds which were used without purification.

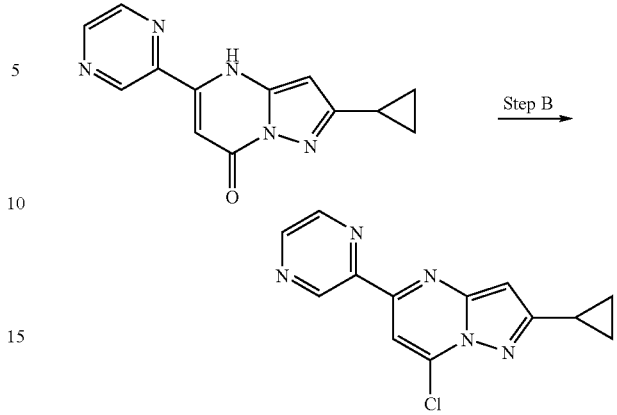

The title compound was prepared according to a procedure analogous to that described in *Polish Journal of Chemistry,* 56, (1982), p 963.

Step A

Preparation 12A (359 mg, 0.01035 mol) and 5-cyclopropyl-2H-pyrazol-3-ylamine (245 mg, 1.05 eq) were heated together at 140° C. for 1.5 h. After cooling to rt, the residue was stirred with EtOH and the resulting solid collected by filtration to give 331 mg of 2-cyclopropyl-5-pyrazin-2-yl-4H-pyrazolo[1,5-a]pyrimidin-7-one.

Step B

The product of step A was dissolved in POCl₃ (4 ml) and cooled to 0° C. N,N-dimethylaniline (0.5 ml, 3 eq) was added and the mixture heated at 80° C. for 16 h. The mixture was cooled to rt and the volatiles removed. The resulting residue was dissolved in CH₂Cl₂, poured onto ice, and neutralized with NaHCO₃(s). The CH₂Cl₂ layer was removed, washed with water, and dried (MgSO₄). The mixture was concentrated under reduced pressure and the residue chromatographed (SiO₂, EtOAc/hexane 1:1) to give 240 mg of the title compound. LCMS MH$^+$=272.0

Preparation 12B

Preparation 12C

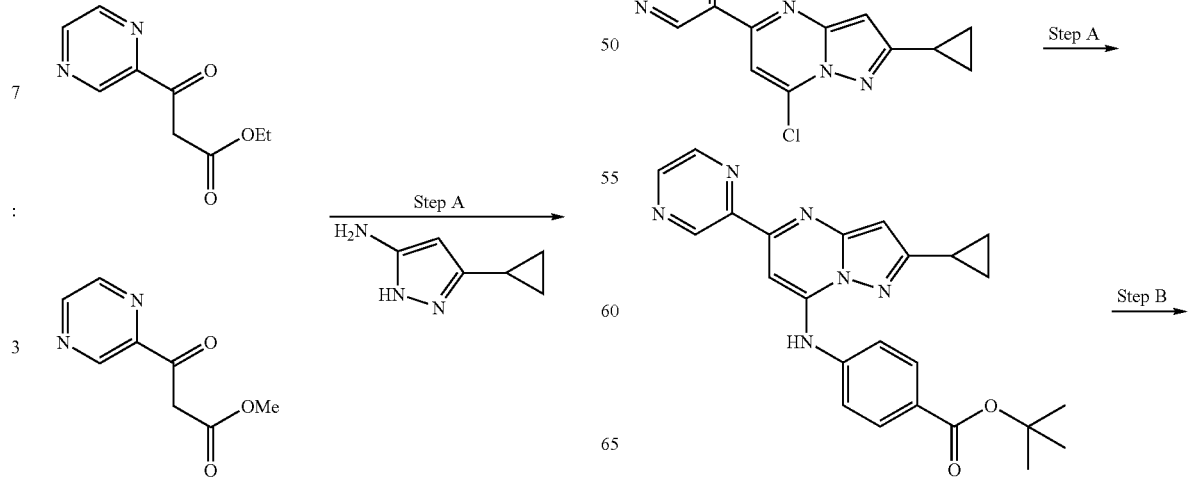

-continued

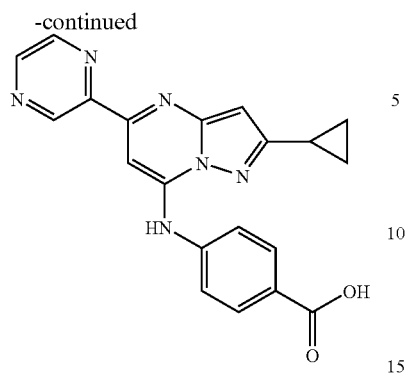

-continued

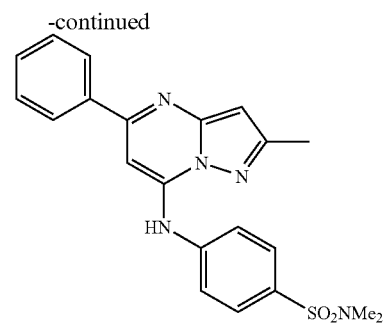

Step A

Preparation 12B (240 mg, 0.883 mmol) was dissolved in NN-dimethylacetamide (4 ml), 4-aminobenzoic acid tert-butyl ester (188 mg, 1.1 eq) was added, followed by t-BuOK (218 mg, 2.2 eq). The mixture was allowed to stir overnight. NH$_4$Cl (sat) was added and the solid collected by filtration to give 392 mg of a white solid which was dissolved in CH$_2$Cl$_2$ (16 ml). Water (0.16 ml), then TFA (2.5 ml) was added, and the mixture was stirred overnight. Complete removal of volatiles under reduced pressure gave 350 mg of the title compound. LCMS: MH$^+$=373.1

Preparation 1A (100 mg, 0.410 mmol) was dissolved in DMF (4 ml), 4-amino-N,N-dimethylbenzenesulfonamide (90 mg, 1.1 eq) was added, followed by potassium tert-butoxide (92 mg, 2 eq). The mixture was stirred for 3 h, when TLC showed complete consumption of starting material. NH$_4$Cl (sat) was added, the resulting solid was collected by filtration and purified by flash chromatography (SiO$_2$, hexane-EtOAc) to give 45 mg of the title compound. LCMS: MH$^+$=408.1.

Example 1A

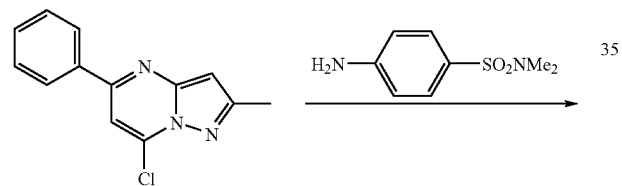

Examples 1B-1P

By essentially the same procedure as in Example 1A, substituting the chlorides in column 1 and the anilines in column 2 the examples shown in column 3 were prepared.

| Ex. | Column 1 | Column 2 | Column 3 | LCMS MH$^+$ |
|---|---|---|---|---|
| 1B | Prep. 1C | H$_2$N-C$_6$H$_4$-SO$_2$NMe$_2$ | (structure) | 438.1 |

| Ex. | Column 1 | Column 2 | Column 3 | LCMS MH+ |
|---|---|---|---|---|
| 1C | Prep. 1D | 4-amino-N,N-dimethylbenzenesulfonamide | 5-(2-methylphenyl)-2-methyl-7-[(4-(N,N-dimethylsulfamoyl)phenyl)amino]pyrazolo[1,5-a]pyrimidine | 422.1 |
| 1D | Prep. 1E | 4-amino-N,N-dimethylbenzenesulfonamide | 5-(2-chlorophenyl)-2-methyl-7-[(4-(N,N-dimethylsulfamoyl)phenyl)amino]pyrazolo[1,5-a]pyrimidine | 442.2 |
| 1E | Prep. 1F | 4-amino-N,N-dimethylbenzenesulfonamide | 5-(4-methoxycarbonylphenyl)-2-methyl-7-[(4-(N,N-dimethylsulfamoyl)phenyl)amino]pyrazolo[1,5-a]pyrimidine | 466.1 |
| 1F | Prep. 1H | 4-amino-N,N-dimethylbenzenesulfonamide | 5-(pyridin-2-yl)-2-methyl-7-[(4-(N,N-dimethylsulfamoyl)phenyl)amino]pyrazolo[1,5-a]pyrimidine | 409.1 |

-continued
| Ex. | Column 1 | Column 2 | Column 3 | LCMS MH+ |
|---|---|---|---|---|
| 1G | Prep. 1I | 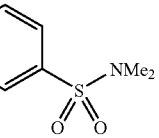 | 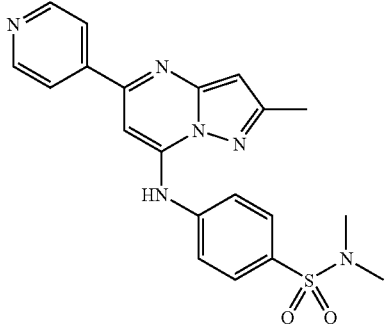 | 409.1 |
| 1H | Prep. 1G | 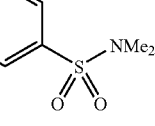 | 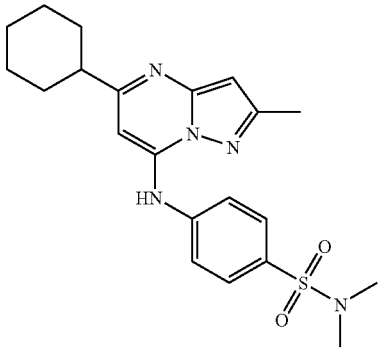 | 414.1 |
| 1I | Prep. 1B | 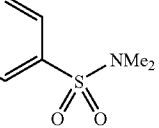 | 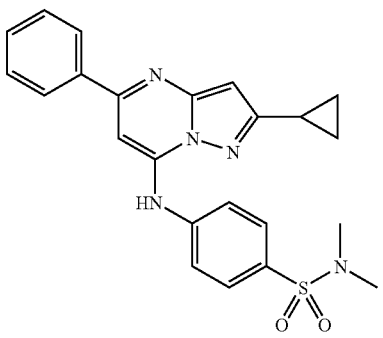 | 434.1 |
| 1J | Prep. 1B | 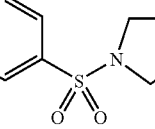 | 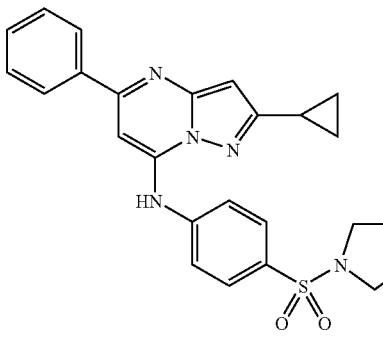 | 460.1 |

-continued
| Ex. | Column 1 | Column 2 | Column 3 | LCMS MH+ |
|---|---|---|---|---|
| 1K | Prep. 1M | 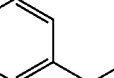 | 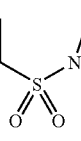 | 478.1 |
| 1L | Prep. 1L | 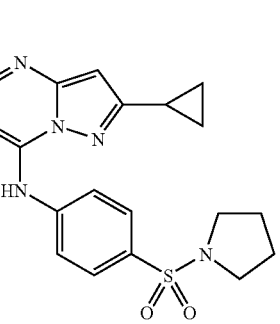 | 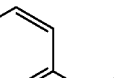 | 461.1 |
| 1M | Prep. 1M | 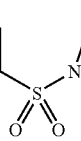 | 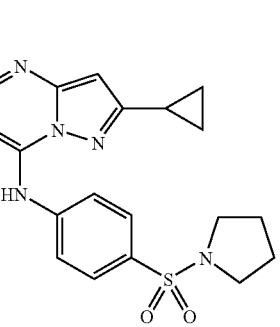 | 452.1 |
| 1N | Prep. 1L | 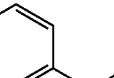 | 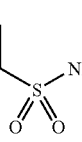 | 435.1 |

US 7,741,318 B2

-continued

| Ex. | Column 1 | Column 2 | Column 3 | LCMS MH+ |
|-----|----------|----------|----------|----------|
| 1O | Prep. 1B | H₂N-C₆H₄-SO₂-N(Me)-CH₂CH₂-(2-pyridyl) | phenyl-pyrazolopyrimidine-cyclopropyl with NH-C₆H₄-SO₂-N(Me)-CH₂CH₂-(2-pyridyl) | 525.1 |
| 1P | Prep. 4B | H₂N-C₆H₄-SO₂-N(Me)-CH₂CH₂-(2-pyridyl) | Cl-pyrazolopyrimidine-cyclopropyl with NH-C₆H₄-SO₂-N(Me)-CH₂CH₂-(2-pyridyl) | 483.3 |

Example 2A

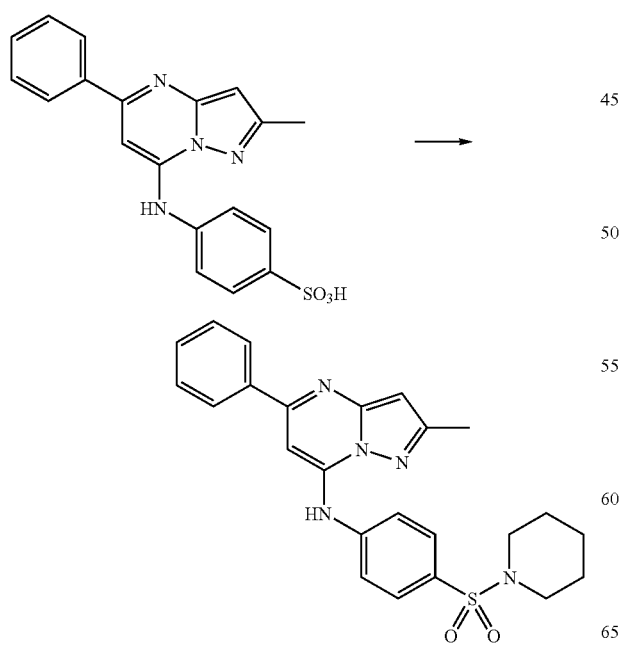

→

Preparation 2A (100 mg, 0.263 mmol) was suspended in POCl₃ (4 ml), N,N-dimethylaniline (33 μL, 1 eq) was added and the mixture heated at 60° C. for 3 h. After cooling to rt, the mixture was concentrated under reduced pressure, suspended in dioxane (3 ml) and piperidine (0.5 ml, excess) was added. After 30 min, TLC showed complete consumption of starting material. Water was added and the mixture extracted with CH₂Cl₂ and EtOAc. The combined extracts were dried (MgSO₄), concentrated under reduced pressure, and the resulting residue purified by flash chromatography (SiO₂, hexane-EtOAc) to give 93 mg of the title compound. LCMS: MH+=448.1.

Examples 2B-2K

By essentially the same procedure set forth in Example 2A, substituting the benzenesulfonic acids in column 1 and the amines in column 2, the examples in column 3 were prepared. In cases where using a large excess of the amine in column 2 was impractical, three equivalents of the amine along with an excess of DIPEA was used (as indicated).

| Ex. | Column 1 | Column 2 | Column 3 | LCMS MH+ |
|---|---|---|---|---|
| 2B | Prep. 2A | H₂N⁀OH | 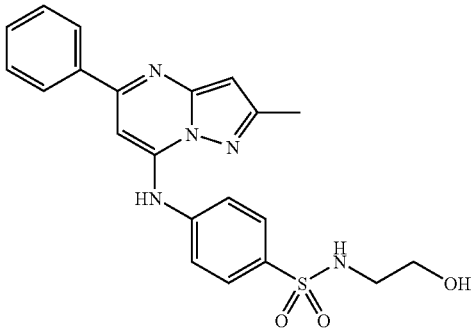 | 424.1 |
| 2C | Prep. 2A | 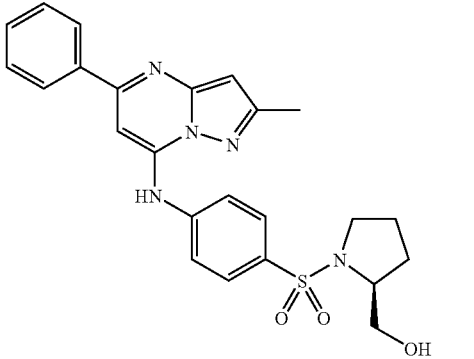<br>+DIPEA | 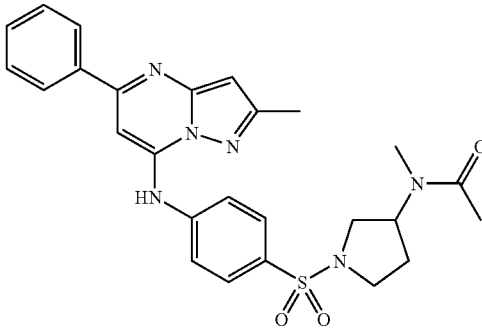 | 464.1 |
| 2D | Prep. 2A | 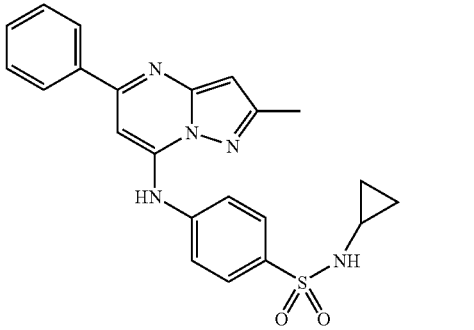<br>+DIPEA | (structure) | 505.3 |
| 2E | Prep. 2A | cyclopropyl-NH₂ | (structure) | 420.2 |

| Ex. | Column 1 | Column 2 | Column 3 | LCMS MH+ |
|---|---|---|---|---|
| 2F | Prep. 2A | 3-acetamidopyrrolidine +DIPEA | 2-methyl-5-phenyl-7-[[4-[(3-acetamidopyrrolidin-1-yl)sulfonyl]phenyl]amino]pyrazolo[1,5-a]pyrimidine | 491.3 |
| 2G | Prep. 2A | N-methyl-2-(pyridin-2-yl)ethylamine +DIPEA | 2-methyl-5-phenyl-7-[[4-[N-methyl-N-[2-(pyridin-2-yl)ethyl]sulfamoyl]phenyl]amino]pyrazolo[1,5-a]pyrimidine | 499.1 |
| 2H | Prep. 2A | N,1-dimethylpyrrolidin-3-amine +DIPEA | 2-methyl-5-phenyl-7-[[4-[N-methyl-N-(1-methylpyrrolidin-3-yl)sulfamoyl]phenyl]amino]pyrazolo[1,5-a]pyrimidine | 477.3 |
| 2I | Prep. 2A | 2-(pyridin-2-yl)ethylamine +DIPEA | 2-methyl-5-phenyl-7-[[4-[N-[2-(pyridin-2-yl)ethyl]sulfamoyl]phenyl]amino]pyrazolo[1,5-a]pyrimidine | 485.1 |

| Ex. | Column 1 | Column 2 | Column 3 | LCMS MH+ |
|---|---|---|---|---|
| 2J | Prep. 2B | H₂N⌒OH |  | 450.1 |
| 2K | Prep. 2B | H₂N-cyclopropyl | 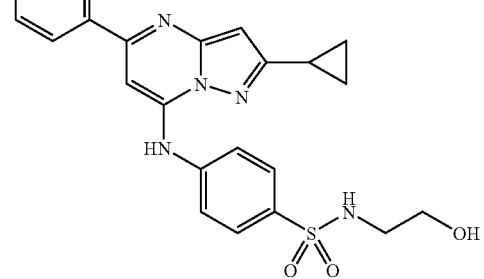 | 446.1 |

Example 3A

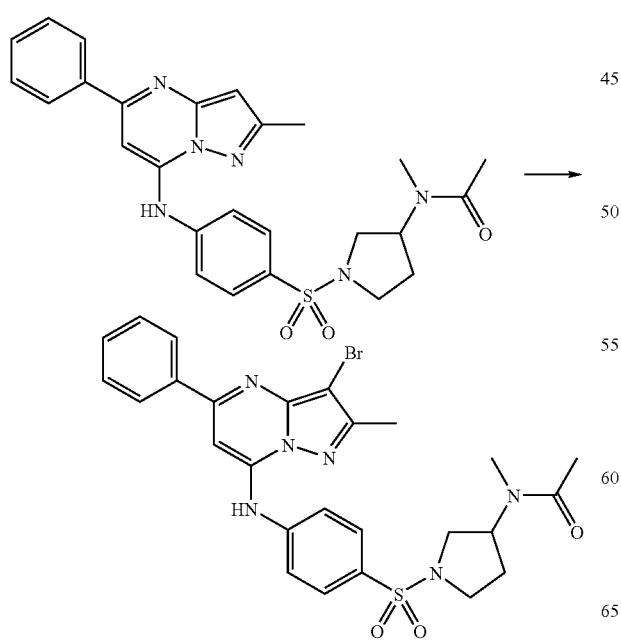

Example 2D (50 mg, 0.1 mmol) was dissolved in THF (2 ml), NBS (18 mg, 1 eq) was added and the mixture stirred for 5 min. The mixture was concentrated under reduced pressure. The resulting residue was purified by flash chromatography (SiO₂, EtOAc) then by HPLC (C18, MeCN/H₂O/HCO₂H 5:95:0.1-95:5:0.1) to give 28 mg of the title compound. LCMS: MH⁺=585.1.

Examples 3B-3G

By essentially the same procedure set forth in Example 3A, substituting the compounds in column 1, the examples in column 2 were prepared.

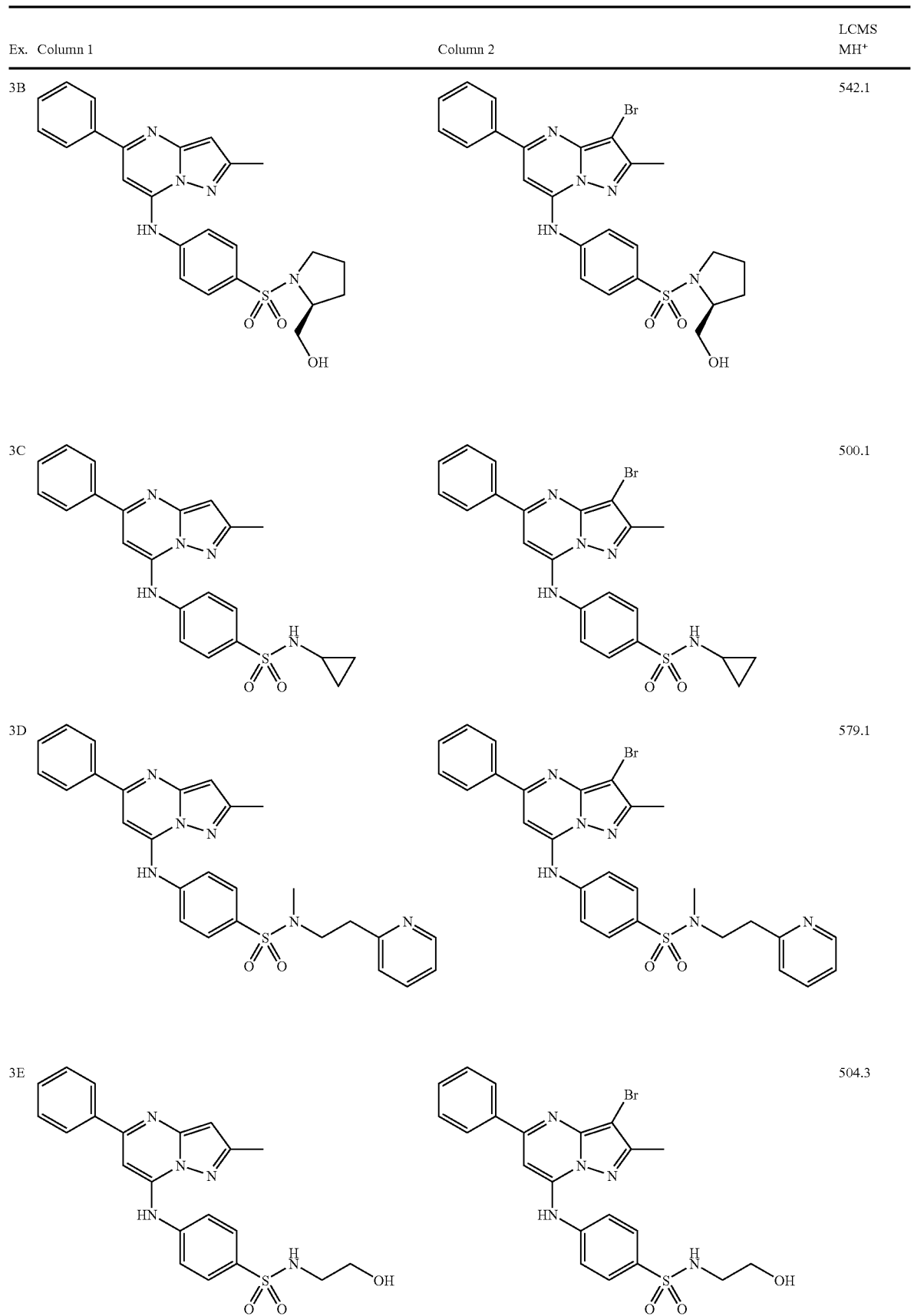

3F
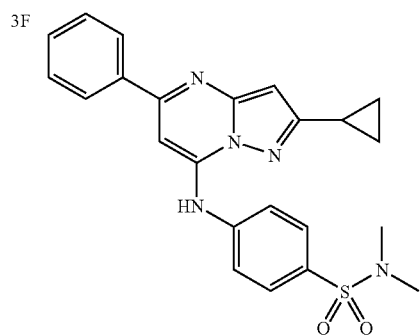
514.1
3G
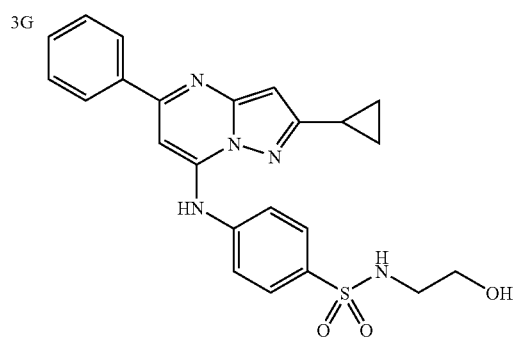
530.1
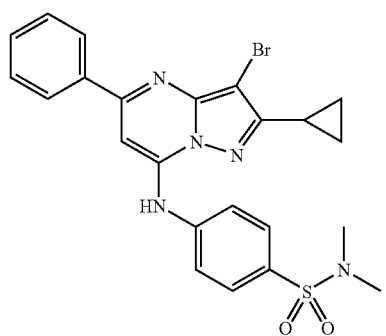
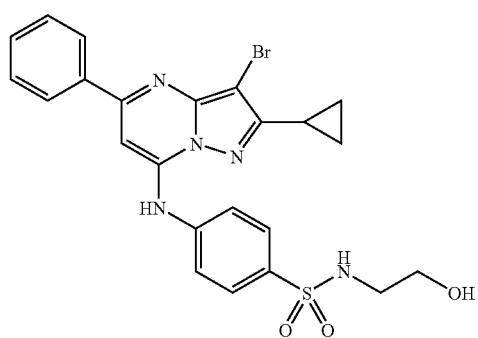
followed by flash chromatography (SiO$_2$, EtOAc/CH$_2$Cl$_2$, 5:95) gave 97 mg of the title compound. LCMS: MH$^+$=486.3.
Example 4
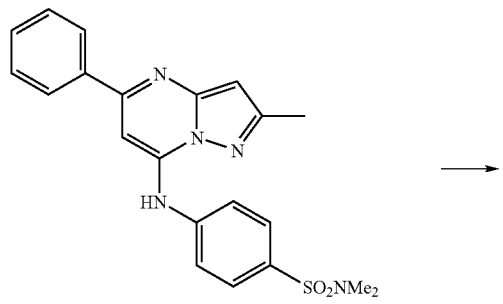
↓
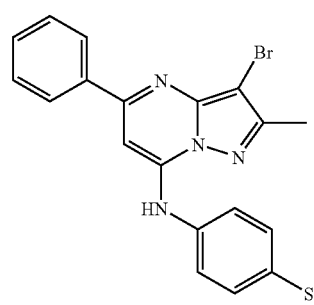
Example 1A (98 mg, 0.24 mmol) was dissolved in MeCN (3 ml). NBS (41 mg, 0.95 eq) was added and the mixture stirred for 45 min. Concentration under reduced pressure
Example 5A
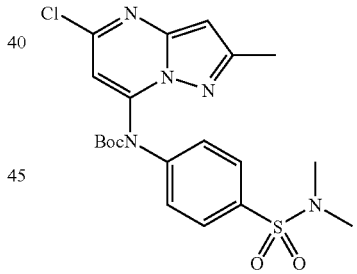
Step A →
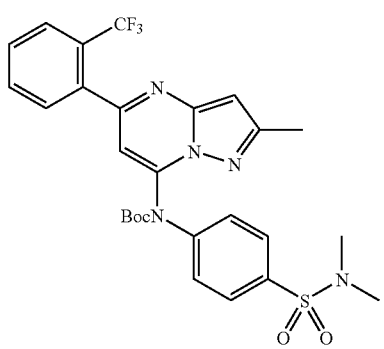
Step B →

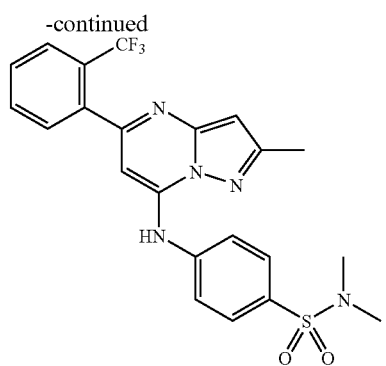

Step A:

Preparation 6 (100 mg, 0.215 mmol) was dissolved in dioxane, 2-trifluoromethyl-benzene boronic acid (61 mg, 1.5 eq), $K_3PO_4$ (137 mg, 3 eq), and Pd(dppf)$Cl_2 \cdot CH_3Cl$ (17 mg, 0.1 eq) were added and the mixture heated overnight at 60° C. After cooling to rt, water was added and the mixture extracted with EtOAc; the extracts were dried (MgSO$_4$), concentrated under reduced pressure, and the resulting residue purified by flash chromatography (SiO$_2$, hexane-1:1 EtOAc/hexane) to give 107 mg of (4-dimethylsulfamoylphenyl)-[2-methyl-5-(2-trifluoromethylphenyl)pyrazolo[1,5-a]pyrimidin-7-yl] carbamic acid tert-butyl ester (LCMS: MH$^+$=576.1).

Step B:

The compound from step A (107 mg) was dissolved in $CH_2Cl_2$ (5 ml); water (0.05 ml), and TFA (0.5 ml) were added and the mixture stirred overnight. The mixture was neutralized with NaHCO$_3$ (sat) and then extracted with $CH_2Cl_2$. The extracts were washed with water, dried (MgSO$_4$), concentrated under reduced pressure, and purified by flash chromatography (SiO$_2$, hexane-EtOAc/hexane 3:1) to give 66 mg of the title compound. LCMS: MH$^+$=476.1.

Examples 5B-5D

By essentially the same procedure set forth in Example 5A, substituting the benzene-boronic acids in column 1, the examples in column 2 were prepared.

| Ex. | Column 1 | Column 2 | LCMS MH$^+$ |
|---|---|---|---|
| 5B | 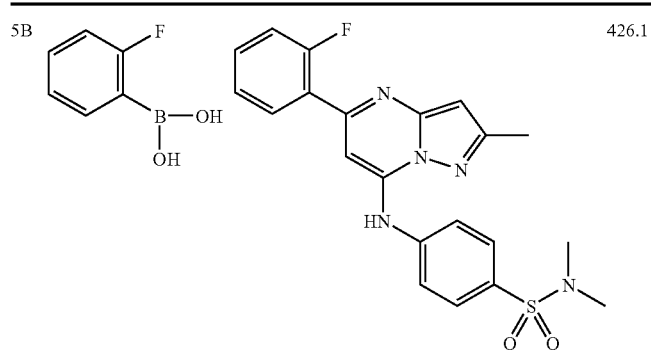 | | 426.1 |
| 5C | 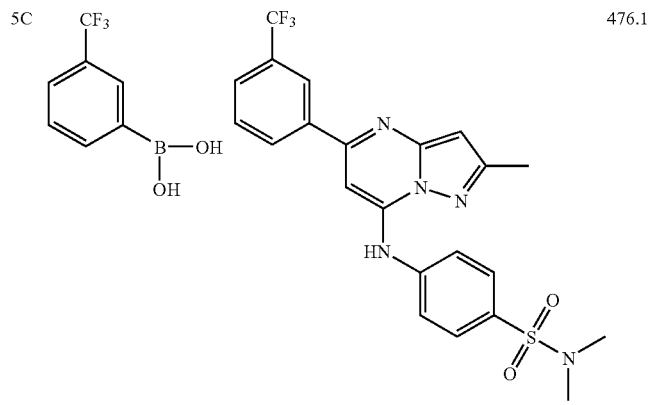 | | 476.1 |

-continued

| Ex. | Column 1 | Column 2 | LCMS MH+ |
|---|---|---|---|
| 5D | 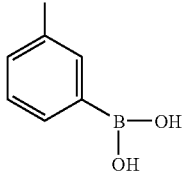 | 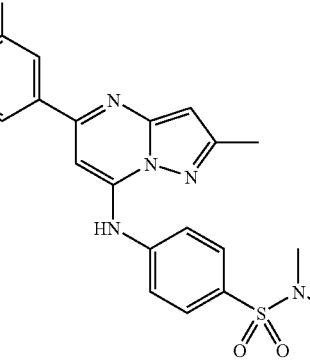 | 426.1 |

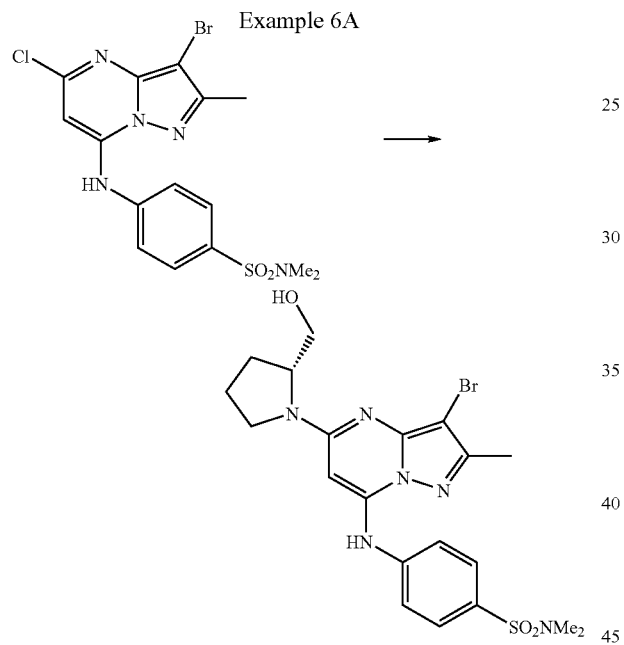

Example 6A

Preparation 5C (110 mg, 0.23 mmol) was suspended in EtOH (2.5 ml), (R)-(−)-2-pyrollidine methanol (0.188 ml, 8 eq) was added followed by 4M HCl in dioxane (356 ml, 6 eq). The mixture was heated for 5 h, when mass spectral analysis showed complete conversion. Water was added and the resulting precipitate collected by filtration to give 54 mg of the title compound. LCMS: MH+=511.3.

Examples 6B-6P

By essentially the same procedure set forth in Example 6A, substituting the amines in column 1 and the chlorides in column 2, the examples in column 3 were prepared. In the cases noted in the table, a mixture of EtOH and THF was used as the primary reaction solvent.

| Ex | Column 1 | Column 2 | Column 3 | Solvent | LCMS MH+ |
|---|---|---|---|---|---|
| 6B |  | Prep. 5A | 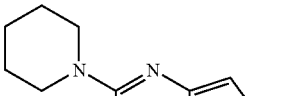 | EtOH | 415.1 |

-continued

| Ex | Column 1 | Column 2 | Column 3 | Solvent | LCMS MH+ |
|----|----------|----------|----------|---------|----------|
| 6C | piperidine | Prep. 5C | (structure) | EtOH | 495.1 |
| 6D | (3R)-3-hydroxypyrrolidine | Prep. 5C | (structure) | EtOH | 497.1 |
| 6E | (2S)-2-(hydroxymethyl)pyrrolidine | Prep. 5C | (structure) | EtOH | 511.1 |
| 6F | morpholine | Prep. 5C | (structure) | EtOH | 497.1 |

-continued
| Ex | Column 1 | Column 2 | Column 3 | Solvent | LCMS MH+ |
|---|---|---|---|---|---|
| 6G | 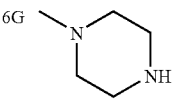 | Prep. 5C | 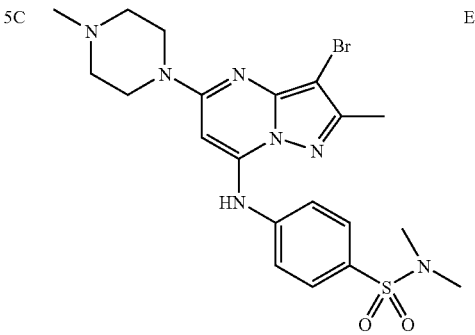 | EtOH | 510.3 |
| 6H | 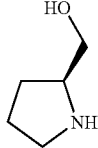 | Prep. 5B | 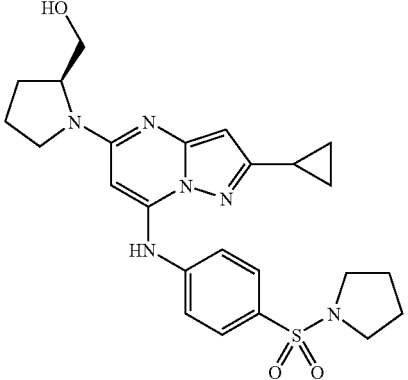 | EtOH | 483.1 |
| 6I | 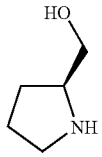 | Ex. 1P | 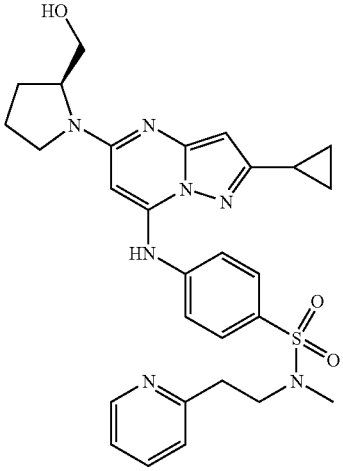 | EtOH/ THF 2:1 | 548.1 |

-continued

| Ex | Column 1 | Column 2 | Column 3 | Solvent | LCMS MH+ |
|---|---|---|---|---|---|
| 6J | (S)-pyrrolidin-2-ylmethanol | Ex. 1P | pyrazolo[1,5-a]pyrimidine with (S)-2-(hydroxymethyl)pyrrolidinyl, cyclopropyl, and anilino-sulfonamide-pyridyl substituents | EtOH/THF 2:1 | 548.1 |
| 6K | piperidine | Ex. 1P | pyrazolo[1,5-a]pyrimidine with piperidinyl, cyclopropyl, and anilino-sulfonamide-pyridyl substituents | EtOH/THF 2:1 | 532.1 |
| 6L | pyrrolidine | Ex. 1P | pyrazolo[1,5-a]pyrimidine with pyrrolidinyl, cyclopropyl, and anilino-sulfonamide-pyridyl substituents | EtOH/THF 2:1 | 518.3 |

Example 7

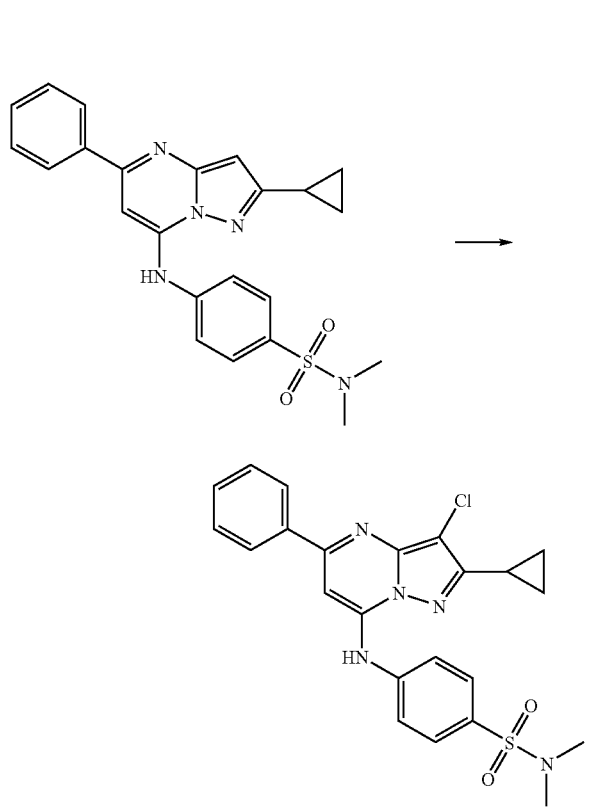

Example 1I (200 mg, 0.461 mmol) was dissolved in THF (3 ml), NCS (59 mg, 0.95 eq) was added and the mixture stirred for 3 h. The reaction mixture was concentrated under reduced pressure and the residue was purified first by flash chromatography (SiO$_2$, hexane/EtOAc 3:1) then by HPLC (C18, MeCN/H$_2$O/HCO$_2$H 5:95:0.1-95:5:0.1) to give 55 mg of the title compound. LCMS: MH$^+$=468.1.

Example 8A

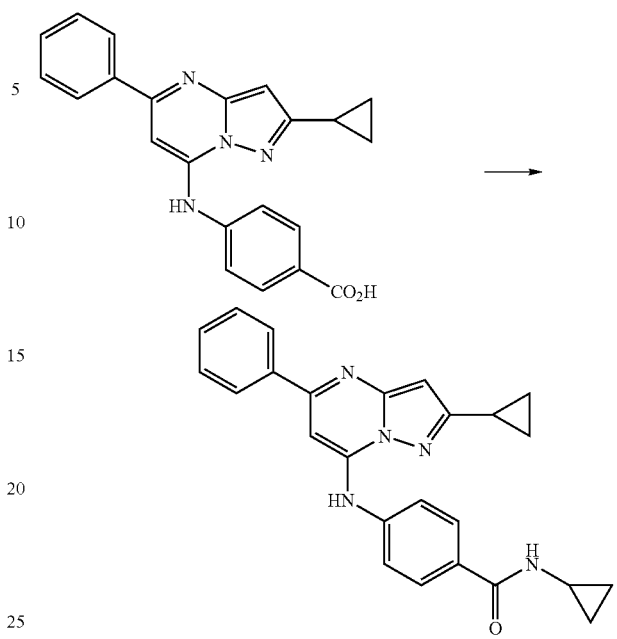

Preparation 7A (30 mg, 0.081 mmol) was dissolved in N,N-dimethylacetamide (2 ml), cyclopropylamine (0.011 ml, 2 eq) was added, followed by DIPEA (0.028 ml, 2 eq) and HATU (61 mg, 2 eq). The mixture was stirred for 5 h, when TLC showed a new compound. Water was added and the mixture extracted with EtOAc, the extracts were washed with NaHCO$_3$ (sat), brine, NH$_4$Cl (sat), brine, and dried (MgSO$_4$). The mixture was concentrated under reduced pressure and the residue purified by flash chromatography (SiO$_2$; hexane-EtOAc) to give 30 mg of the title compound. LCMS: MH$^+$=410.2.

Examples 8B-8JJJ

By essentially the same procedure set forth in Example 8A, substituting the amines in column 1 and the acids in column 2, the examples shown in column 3 were prepared.

| Ex. | Column 1 | Column 2 | Column 3 | LCMS MH$^+$ |
|---|---|---|---|---|
| 8B | MeNH$_2$ | Prep. 7F | (structure shown) | 358.1 |

-continued

| Ex. | Column 1 | Column 2 | Column 3 | LCMS MH+ |
|---|---|---|---|---|
| 8C | HO-CH2-CH2-NH2 | Prep. 7F | [structure: 5-phenyl-2-methyl-pyrazolo[1,5-a]pyrimidine linked via NH to 4-(N-(2-hydroxyethyl)carbamoyl)phenyl] | 388.1 |
| 8D | MeO-NH2 | Prep. 7F | [structure: 5-phenyl-2-methyl-pyrazolo[1,5-a]pyrimidine linked via NH to 4-(N-methoxycarbamoyl)phenyl] | 374.2 |
| 8E | NHMe2 | Prep. 7F | [structure: 5-phenyl-2-methyl-pyrazolo[1,5-a]pyrimidine linked via NH to 4-(N,N-dimethylcarbamoyl)phenyl] | 372.1 |
| 8F | 2-(pyridin-2-yl)ethylamine | Prep. 7A | [structure: 5-phenyl-2-cyclopropyl-pyrazolo[1,5-a]pyrimidine linked via NH to 4-(N-(2-(pyridin-2-yl)ethyl)carbamoyl)phenyl] | 475.1 |

| Ex. | Column 1 | Column 2 | Column 3 | LCMS MH+ |
|---|---|---|---|---|
| 8G | 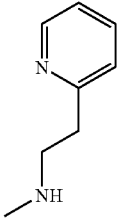 | Prep. 7F | 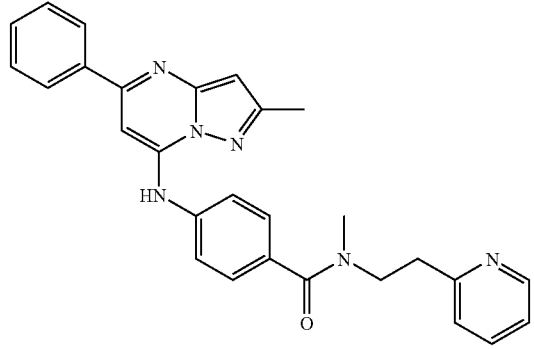 | 463.1 |
| 8H | 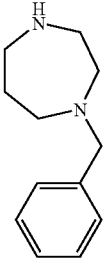 | Prep. 7A | 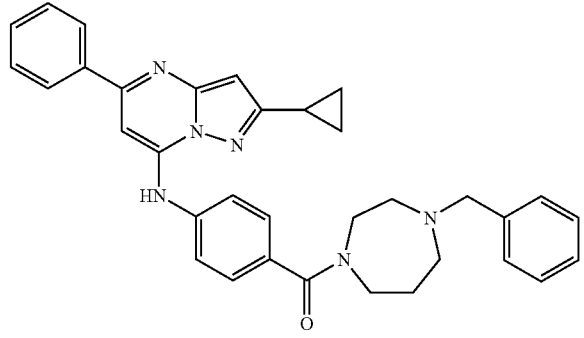 | 543.1 |
| 8I | 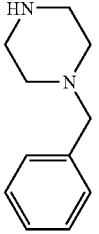 | Prep. 7A | 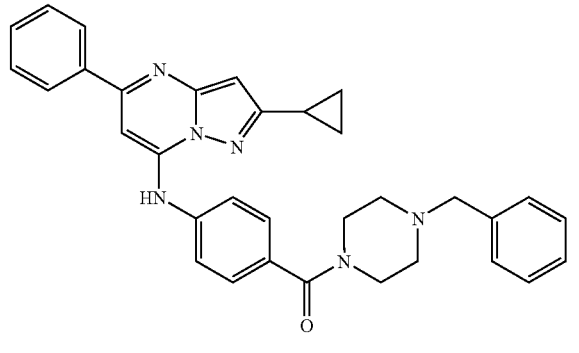 | 529.1 |
| 8J | 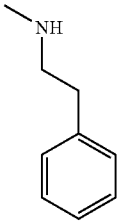 | Prep. 7A | 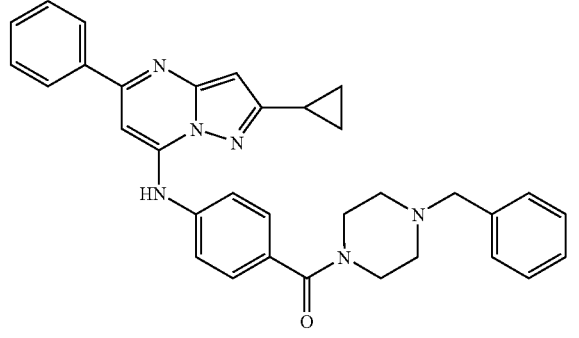 | 488.3 |

| Ex. | Column 1 | Column 2 | Column 3 | LCMS MH+ |
|---|---|---|---|---|
| 8K | | Prep. 7A | | 556.1 |
| 8L | | Prep. 7A | | 506.1 |
| 8M | | Prep. 7A | | 506.1 |
| 8N | | Prep. 7A | | 540.1 |

-continued

| Ex. | Column 1 | Column 2 | Column 3 | LCMS MH+ |
|---|---|---|---|---|
| 8O | (2,4-dichlorophenethyl)methylamine | Prep. 7A | [structure] | 556.1 |
| 8P | (2-chlorophenethyl)methylamine | Prep. 7A | [structure] | 522.1 |
| 8Q | (2-fluorophenethyl)methylamine | Prep. 7A | [structure] | 506.1 |
| 8R | 2,6-dichlorobenzylamine | Prep. 7A | [structure] | 528.1 |

-continued

| Ex. | Column 1 | Column 2 | Column 3 | LCMS MH+ |
|---|---|---|---|---|
| 8S | (N-methyl 2,6-dichlorobenzylamine) | Prep. 7A | (structure) | 542.3 |
| 8T | (2,6-difluorobenzylamine) | Prep. 7A | (structure) | 496.1 |
| 8U | (2-chloro-6-fluorobenzylamine) | Prep. 7A | (structure) | 512.1 |
| 8V | (2-chloro-6-methylbenzylamine) | Prep. 7A | (structure) | 508.1 |

| Ex. | Column 1 | Column 2 | Column 3 | LCMS MH+ |
|---|---|---|---|---|
| 8W | 2,6-dimethoxybenzylamine | Prep. 7A | (structure) | 520.3 |
| 8X | (S)-N-methyl-1-phenylethylamine | Prep. 7A | (structure) | 488.3 |
| 8Y | 2-chloro-3,6-difluorobenzylamine | Prep. 7A | (structure) | 530.1 |
| 8Z | N-(2-chloro-6-fluorobenzyl)propylamine | Prep. 7A | (structure) | 554.1 |

| Ex. | Column 1 | Column 2 | Column 3 | LCMS MH+ |
|---|---|---|---|---|
| 8AA | 2,4-dichloro-6-methylbenzylamine | Prep. 7A | (structure) | 542.1 |
| 8BB | 3-chloro-2,6-difluorobenzylamine | Prep. 7A | (structure) | 530.1 |
| 8CC | 2-chloro-6-fluoro-3-methylbenzylamine | Prep. 7A | (structure) | 526.1 |
| 8DD | 2,3,6-trifluorobenzylamine | Prep. 7A | (structure) | 514.1 |

-continued
| Ex. | Column 1 | Column 2 | Column 3 | LCMS MH+ |
|---|---|---|---|---|
| 8EE | 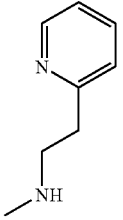 | Prep. 7G | 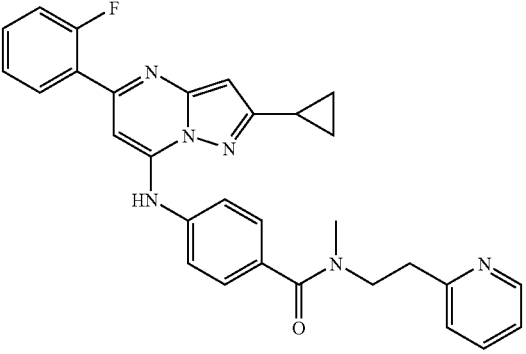 | 507.1 |
| 8FF | 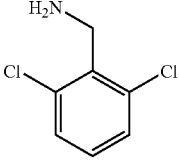 | Prep. 7G | 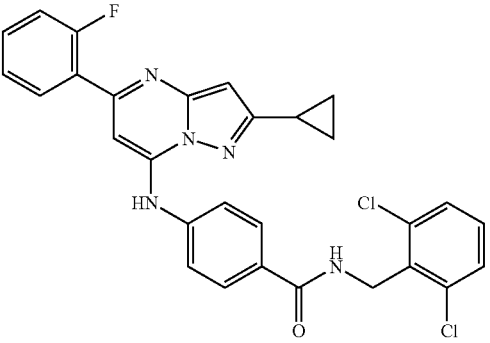 | 546.3 |
| 8GG | 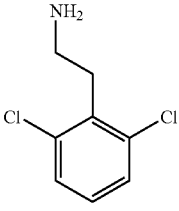 | Prep. 7G | 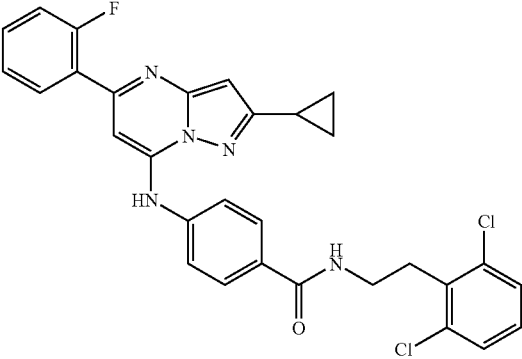 | 560.1 |
| 8HH | 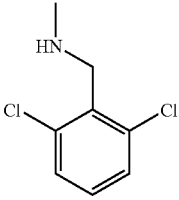 | Prep. 7G | 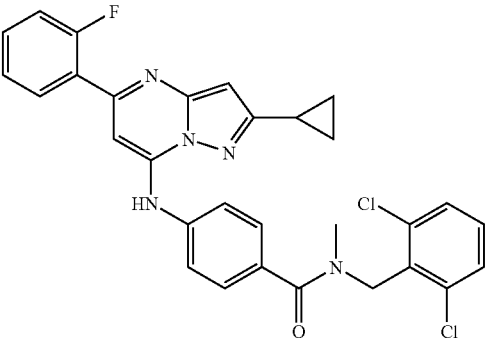 | 560.1 |

| Ex. | Column 1 | Column 2 | Column 3 | LCMS MH+ |
|---|---|---|---|---|
| 8II | 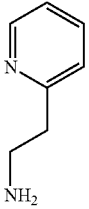 | Prep. 7C | 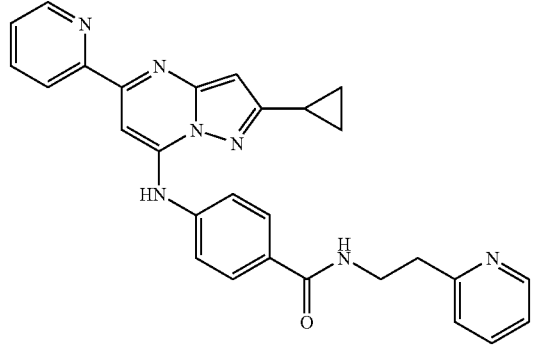 | 476.1 |
| 8JJ | 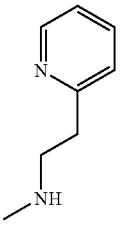 | Prep. 7C | 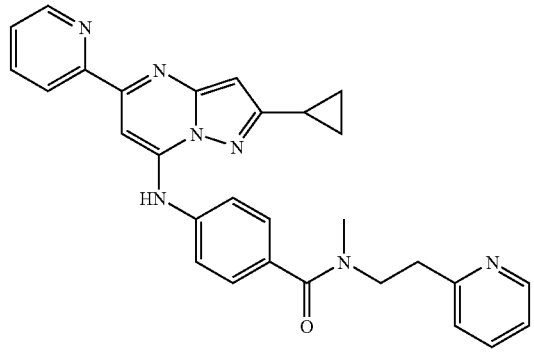 | 490.1 |
| 8KK | 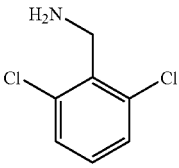 | Prep. 7C | 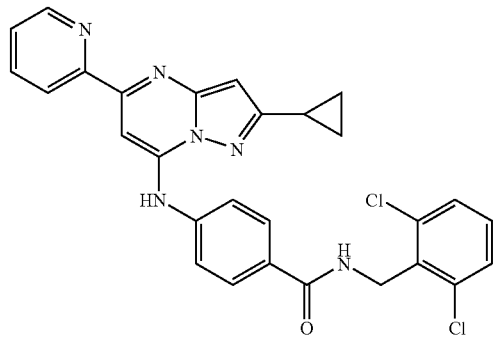 | 529.1 |
| 8LL | 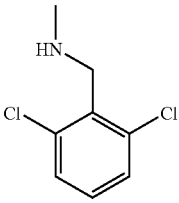 | Prep. 7C | 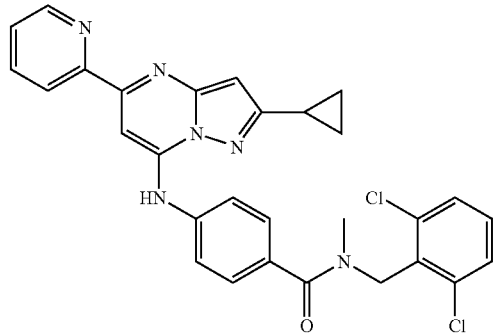 | 543.1 |

-continued
| Ex. | Column 1 | Column 2 | Column 3 | LCMS MH+ |
|---|---|---|---|---|
| 8MM | 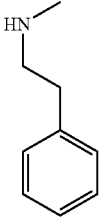 | Prep. 7C | 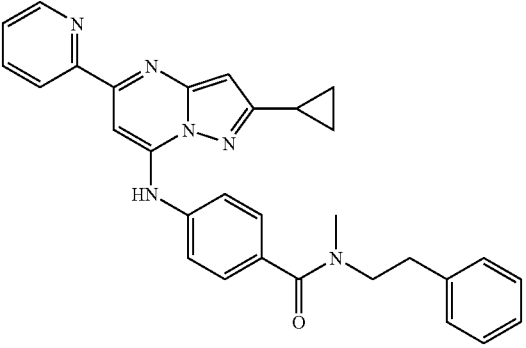 | 489.1 |
| 8NN | 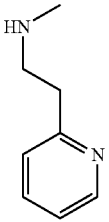 | Prep. 7D | 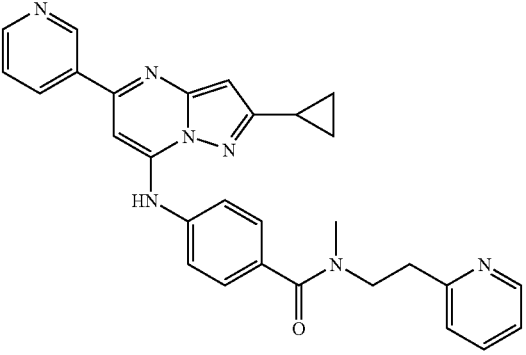 | 490.3 |
| 8OO | 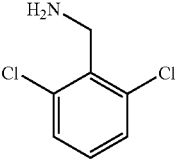 | Prep. 7D | 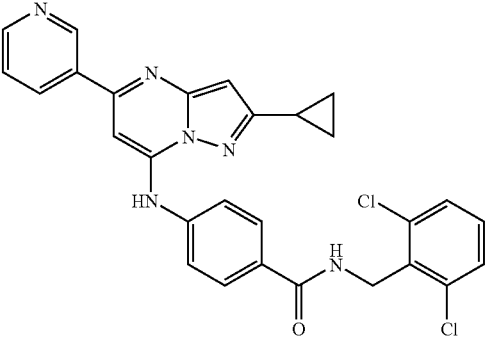 | 529.1 |
| 8PP | 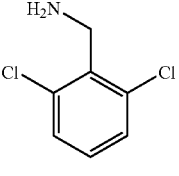 | Prep. 7E | 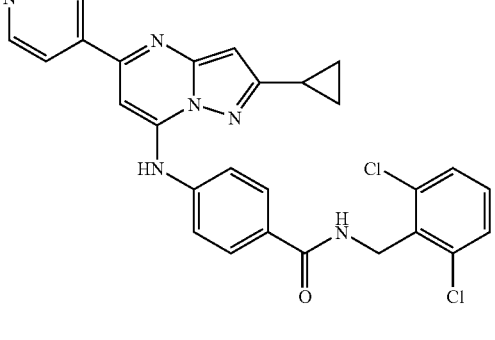 | 529.1 |

| Ex. | Column 1 | Column 2 | Column 3 | LCMS MH+ |
|---|---|---|---|---|
| 8QQ | 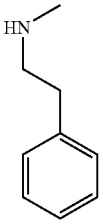 | Prep. 7E | 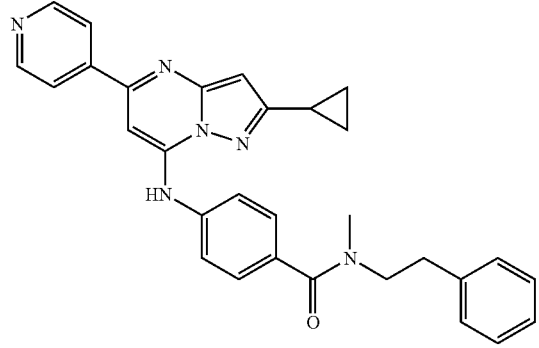 | 489.1 |
| 8RR | 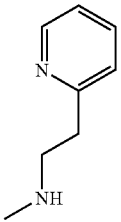 | Prep. 7B | 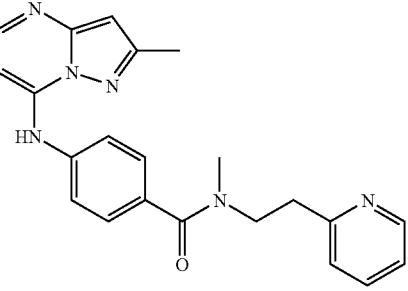 | 421.2 |
| 8SS | 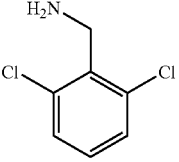 | Prep. 7B | 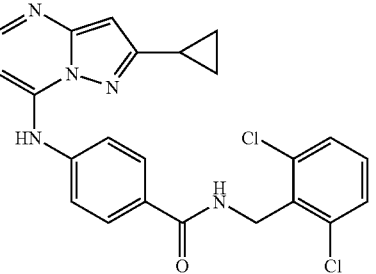 | 486.1 |
| 8TT | 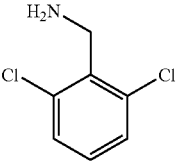 | Prep. 11 | 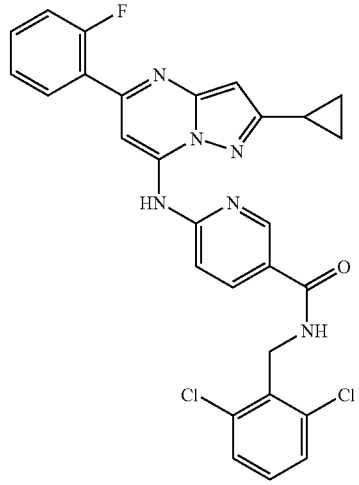 | 547.1 |

-continued

| Ex. | Column 1 | Column 2 | Column 3 | LCMS MH+ |
|---|---|---|---|---|
| 8UU | (1-benzylpiperazine) | Prep. 11 | (structure) | 548.1 |
| 8VV | (N-methyl-2-(2-fluorophenyl)ethylamine) | Prep. 11 | (structure) | 525.1 |
| 8WW | (2,6-dichlorobenzylamine) | Prep. 12C | (structure) | 530.1 |

-continued

| Ex. | Column 1 | Column 2 | Column 3 | LCMS MH+ |
|---|---|---|---|---|
| 8XX | | Prep. 12C | | 531.1 |
| 8YY | | Prep. 12C | | 508.1 |
| 8ZZ | | Prep. 7F | | 504.1 |

| Ex. | Column 1 | Column 2 | Column 3 | LCMS MH+ |
|---|---|---|---|---|
| 8AAA | 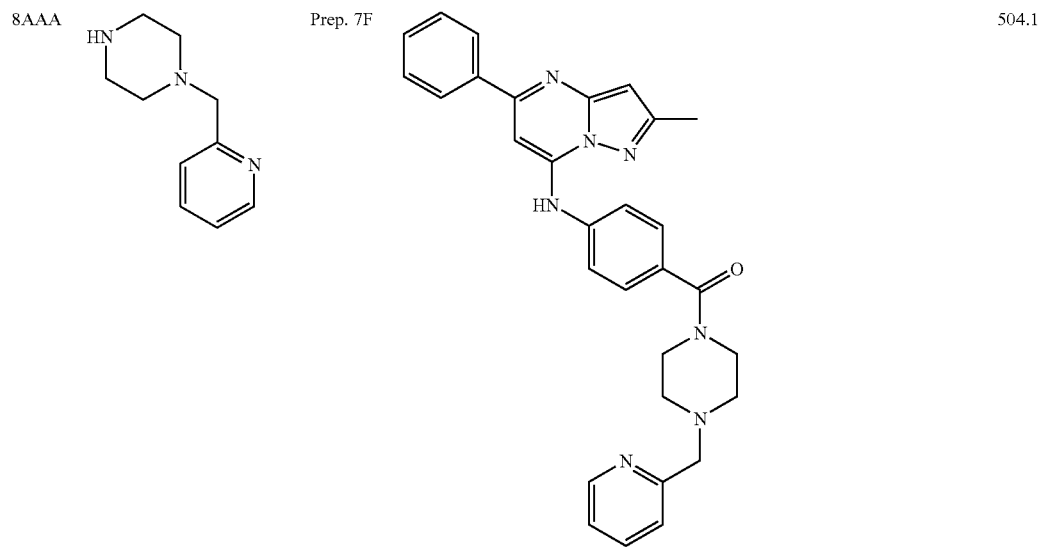 | Prep. 7F | | 504.1 |
| 8BBB | 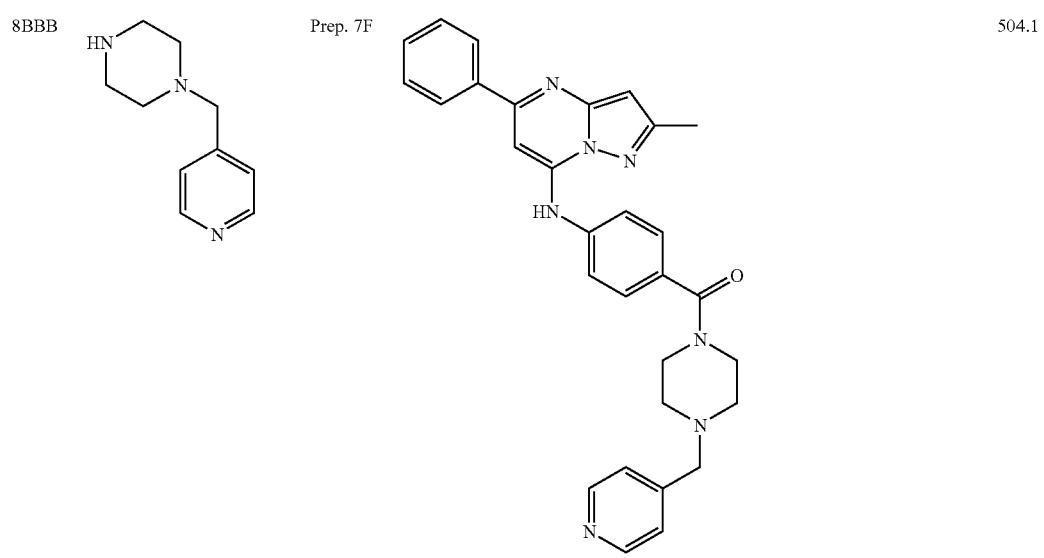 | Prep. 7F | | 504.1 |

| Ex. | Column 1 | Column 2 | Column 3 | LCMS MH+ |
|---|---|---|---|---|
| 8CCC | 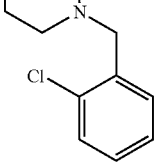 | Prep. 7A | 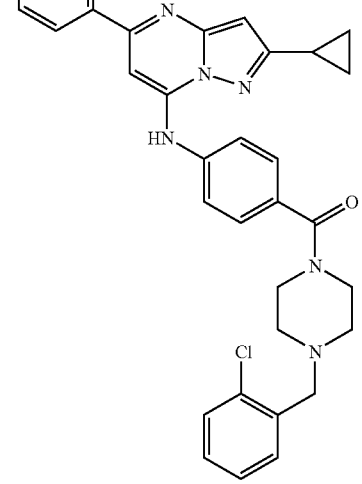 | 563.1 |
| 8DDD | 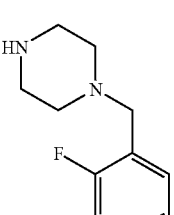 | Prep. 7A | 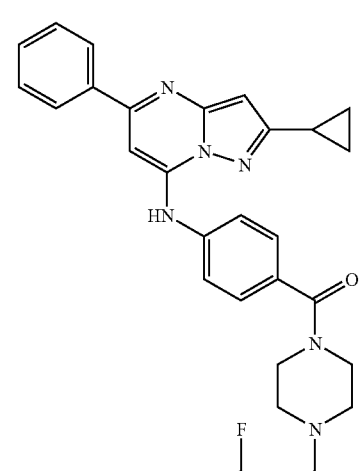 | 547.3 |

| Ex. | Column 1 | Column 2 | Column 3 | LCMS MH+ |
|---|---|---|---|---|
| 8EEE | 2-fluorobenzyl piperazine | Prep. 7F | 5-phenyl-2-methyl-pyrazolo[1,5-a]pyrimidin-7-yl amino phenyl carbonyl 4-(2-fluorobenzyl)piperazine | 521.1 |
| 8FFF | 4-fluorobenzyl piperazine | Prep. 7A | 5-phenyl-2-cyclopropyl-pyrazolo[1,5-a]pyrimidin-7-yl amino phenyl carbonyl 4-(4-fluorobenzyl)piperazine | 547.1 |

-continued

| Ex. | Column 1 | Column 2 | Column 3 | LCMS MH+ |
|---|---|---|---|---|
| 8GGG | 4-fluorobenzyl piperazine | Prep. 7F | pyrazolopyrimidine amide structure | 521.1 |
| 8HHH | 3-fluorobenzyl piperazine | Prep. 7F | pyrazolopyrimidine amide structure | 521.1 |

-continued
| Ex. | Column 1 | Column 2 | Column 3 | LCMS MH+ |
|---|---|---|---|---|
| 8III | 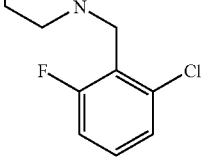 | Prep. 7F | 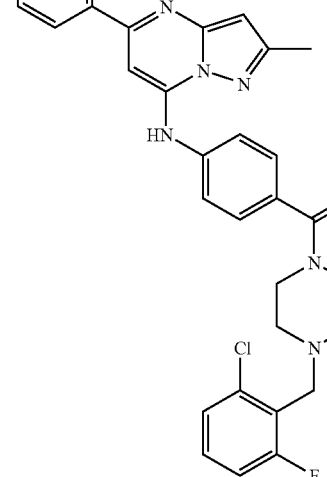 | 555.1 |
| 8JJJ | 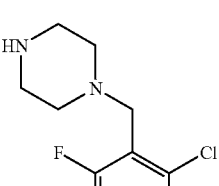 | Prep. 7A | 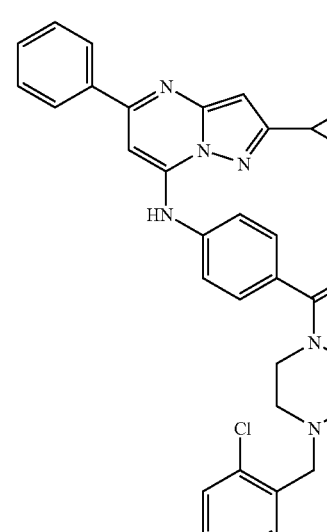 | 581.3 |
Example 9
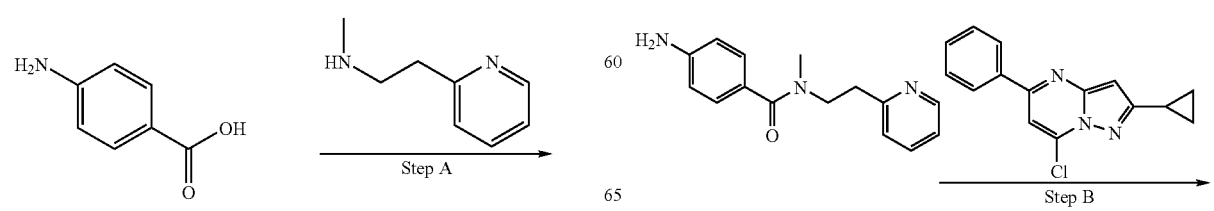
Step A
-continued
Step B -continued

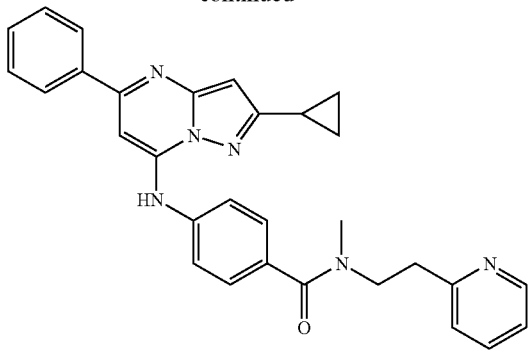

Step A:

p-Aminobenzoic acid (1 g, 0.0073 mol) was dissolved in DMF (15 ml), methyl-(2-pyridin-2-yl-ethyl)amine (5 ml, 5 eq) was added, followed by DIPEA (1.91 ml, 1.5 eq), and HATU (4.1 g, 1.5 eq). After stirring for 3 h, TLC showed complete consumption of starting material. Water was added and the mixture extracted with $CH_2Cl_2$, the organic extracts were washed with $NaHCO_3$ (sat), $NH_4Cl$ (sat), dried ($MgSO_4$), concentrated under reduced pressure, and purified by flash chromatography ($SiO_2$, EtOAc-EtOAc/MeOH 95:5) to give 1.43 g of 4-amino-N-methyl-N-(2-pyridin-2-ylethyl) benzamide.

Step B:

Preparation 1B (100 mg, 0.371 mmol) and the product of step A (142 mg, 1.5 eq) were dissolved in DMF (2 ml), potassium tert-butoxide (91 mg, 2.2 eq) was added and the mixture allowed to stir overnight. Water was added and the mixture extracted with EtOAc, dried ($MgSO_4$), concentrated under reduced pressure, and the residue purified by flash chromatography ($SiO_2$, hexane-EtOAc) to give 56 mg of the title compound. LCMS: $MH^+$=489.3.

Example 10A-10D

By essentially the same procedure set forth in Example 6A, substituting the amines in column 1 and the chlorides in column 2, the examples in column 3 were prepared. In all cases a 1:1 mixture of EtOH and THF was used as the primary reaction solvent.

| Ex. | Column 1 | Column 2 | Column 3 | LCMS $MH^+$ |
|---|---|---|---|---|
| 10A | ⟨pyrrolidine-NH⟩ | Ex. 8RR | ⟨structure⟩ | 456.1 |
| 10B | ⟨pyrrolidine-NH⟩ | Ex. 8SS | ⟨structure⟩ | 521.1 |

| Ex. | Column 1 | Column 2 | Column 3 | LCMS MH+ |
|---|---|---|---|---|
| 10C | HO-pyrrolidine-NH | Ex. 8SS | HO-pyrrolidinyl-pyrazolopyrimidine-cyclopropyl with HN-phenyl-C(O)NH-CH2-(2,6-dichlorophenyl) | 551.1 |
| 10D | HO-pyrrolidine-NH (enantiomer) | Ex. 8SS | HO-pyrrolidinyl-pyrazolopyrimidine-cyclopropyl with HN-phenyl-C(O)NH-CH2-(2,6-dichlorophenyl) | 551.1 |

Example 11A

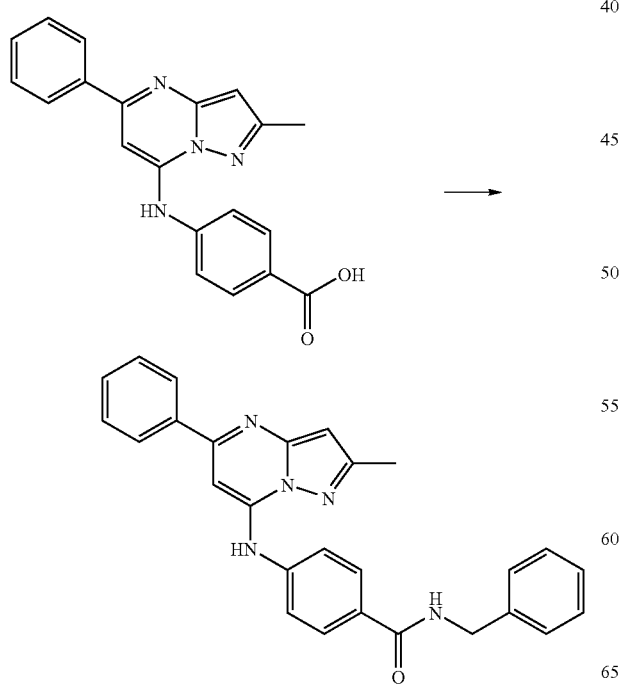

Preparation 7F (10 mg, 0.029 mmol) and HOBT (5.9 mg, 1.5 eq) were dissolved in DMF/THF/MeCN (0.5 ml/0.2 ml/0.3 ml). PS-EDC resin (61 mg, 3 eq) was added followed by 2 equivalents of benzyl amine. The mixture was shaken overnight. The resin was removed by filtration and the filtrate treated with amberlyst A-26 resin (68 mg) for 2 h. The resin was removed by filtration and the solution concentrated to give 4.4 mg of the title compound. LCMS: MH+=434.1.

Examples 11B-11R

Using essentially the same procedure as Example 11A, substituting the amines in column 1, the compounds in column 2 were synthesized.

| Ex. | Column 1 | Column 2 | LCMS MH+ |
|---|---|---|---|
| 11B | 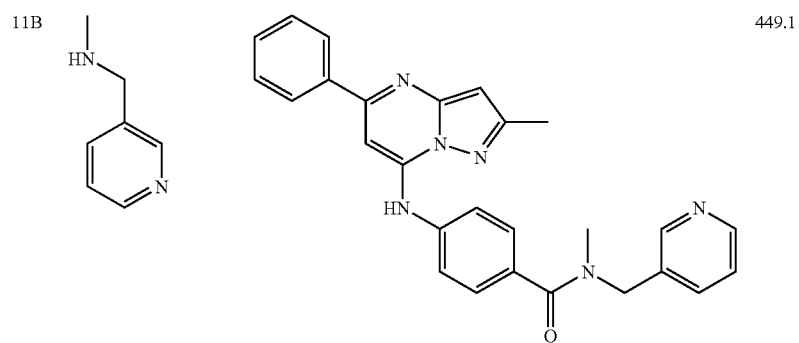 | | 449.1 |
| 11C | 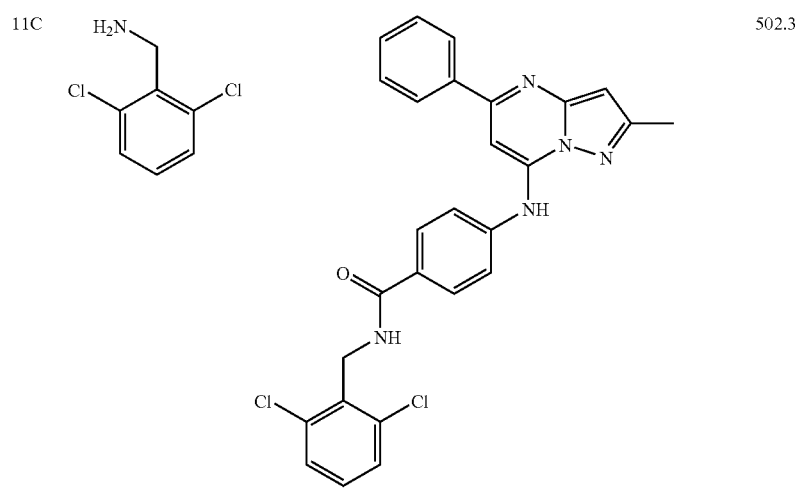 | | 502.3 |
| 11D | 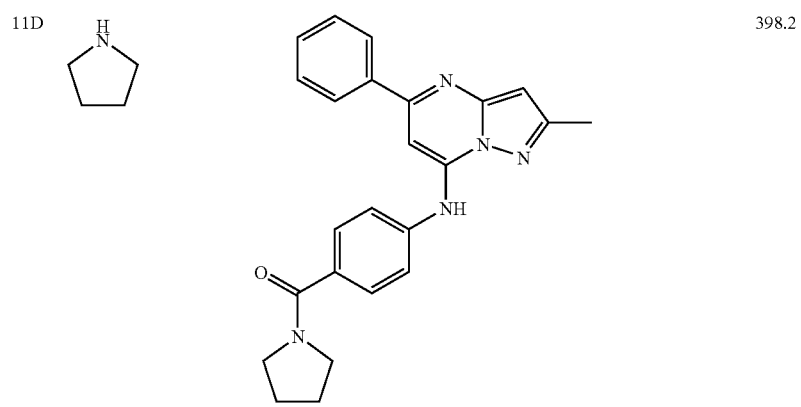 | | 398.2 |

| Ex. | Column 1 | Column 2 | LCMS MH+ |
| --- | --- | --- | --- |
| 11E | (piperidine) | (structure) | 412.2 |
| 11F | (thiazolidine) | (structure) | 416.2 |
| 11G | (azepane) | (structure) | 426.2 |

-continued
| Ex. | Column 1 | Column 2 | LCMS MH+ |
|---|---|---|---|
| 11H | 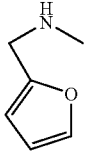 | 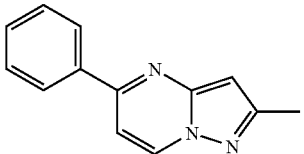 | 438.2 |
| 11I | 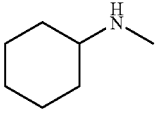 | 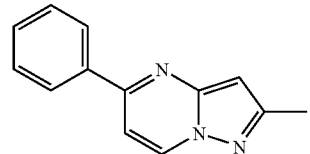 | 440.2 |
| 11J | 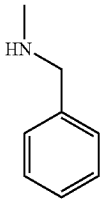 | 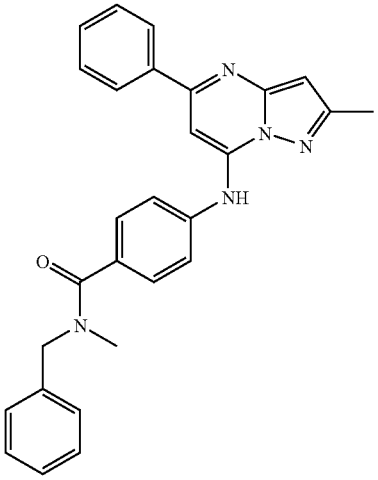 | 448.2 |

| Ex. | Column 1 | Column 2 | LCMS MH+ |
|---|---|---|---|
| 11K | 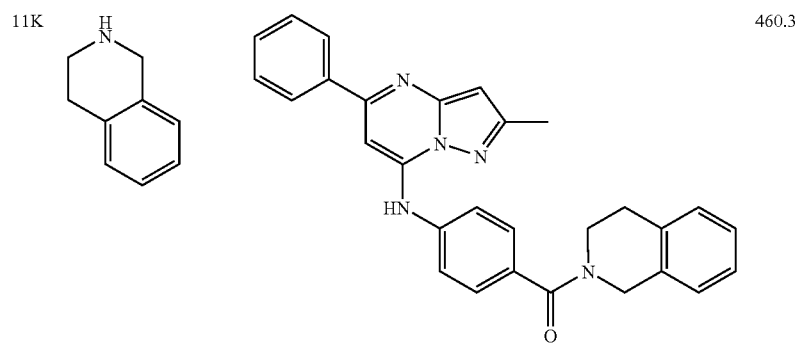 | | 460.3 |
| 11L | 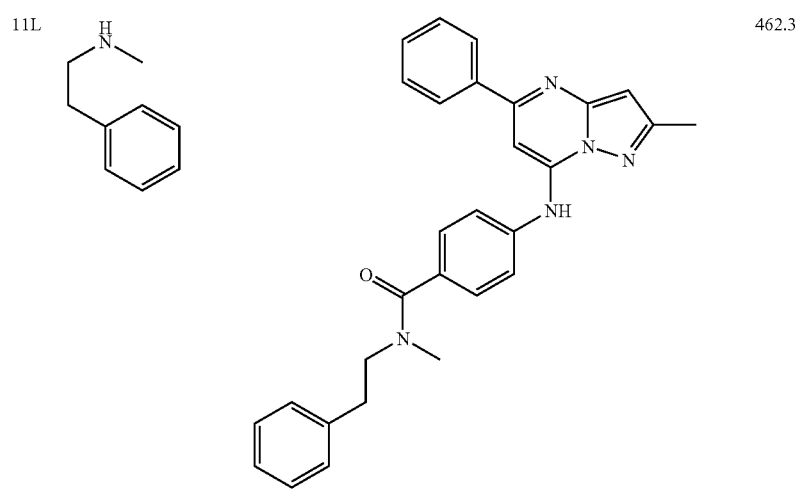 | | 462.3 |
| 11M | 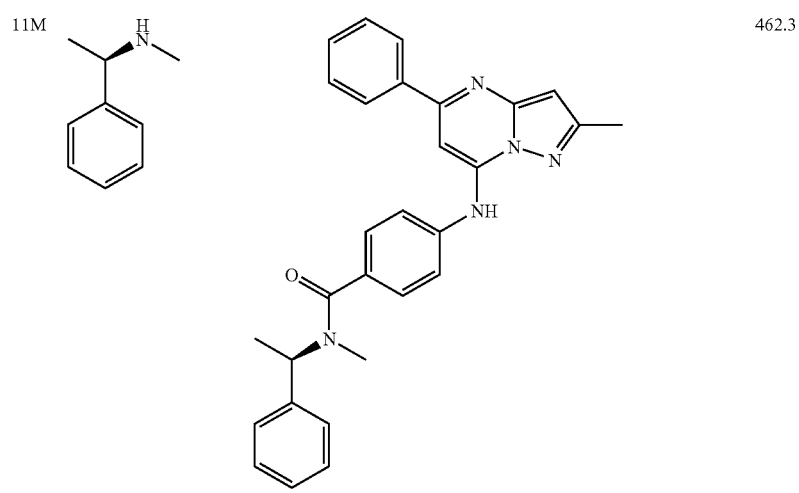 | | 462.3 |

| Ex. | Column 1 | Column 2 | LCMS MH+ |
|---|---|---|---|
| 11N | 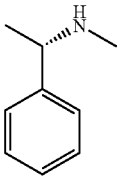 | 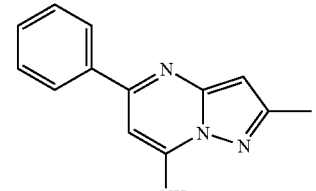 | 462.3 |
| 11O | 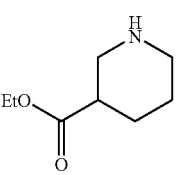 | 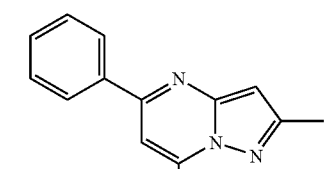 | 484.3 |
| 11P | 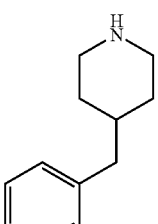 | 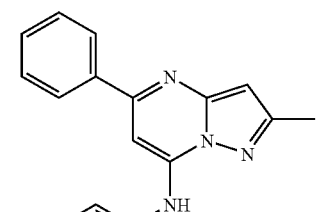 | 502.3 |

-continued
| Ex. | Column 1 | Column 2 | LCMS MH+ |
|---|---|---|---|
| 11Q | 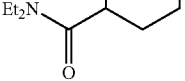 | 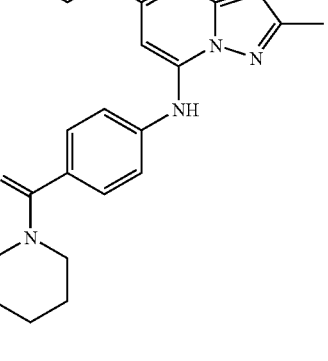 | 511.3 |
| 11R |  | 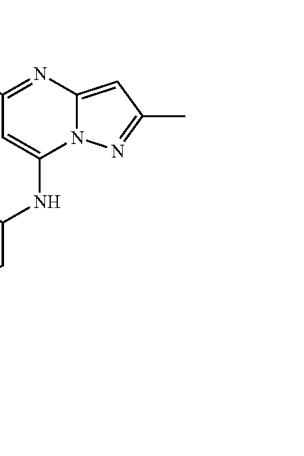 | 441.2 |
| 11S | 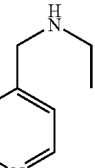 | 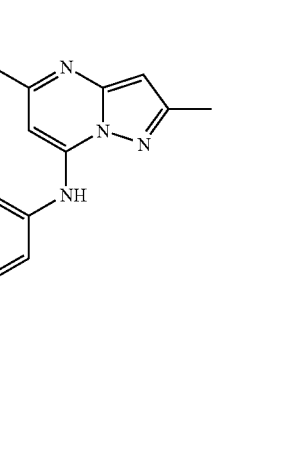 | 463.3 |

| Ex. | Column 1 | Column 2 | LCMS MH+ |
|---|---|---|---|
| 11T | 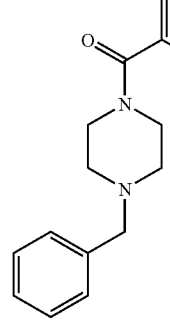 | 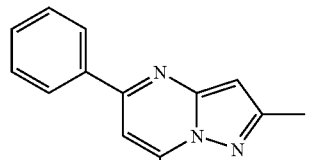 | 481.3 |
| 11U | 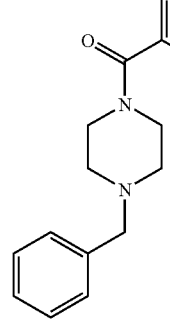 | 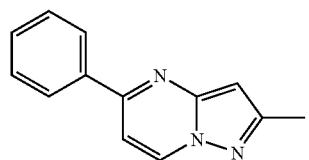 | 503.3 |

| Ex. | Column 1 | Column 2 | LCMS MH+ |
|---|---|---|---|
| 11V | 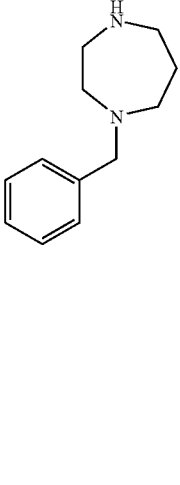 | 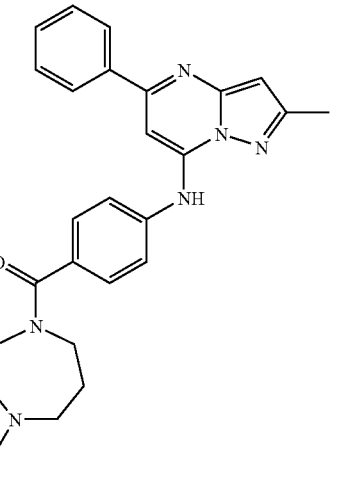 | 517.3 |

Example 12

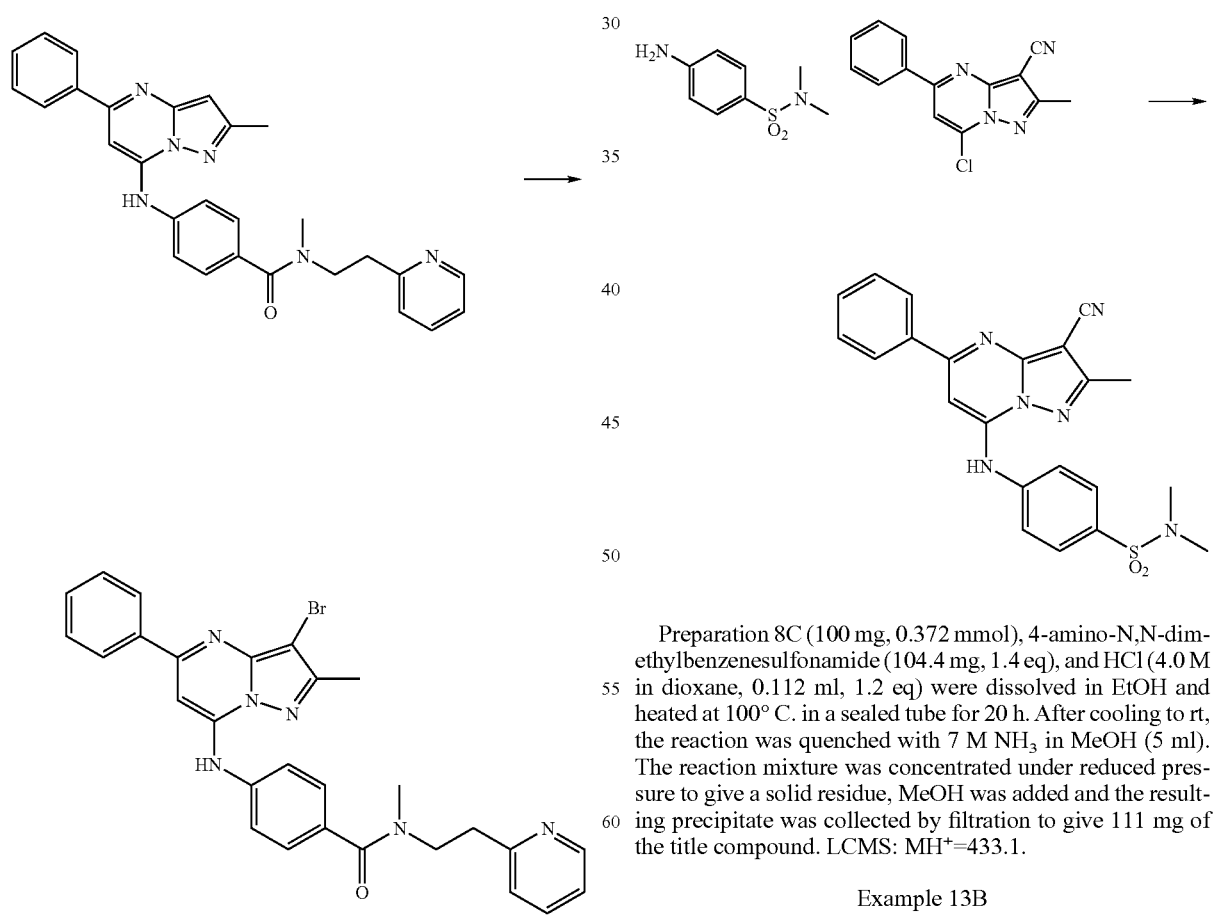

The title compound was prepared in essentially the same manner set forth in Example 3A. LCMS: MH+=541.3.

Example 13A

Preparation 8C (100 mg, 0.372 mmol), 4-amino-N,N-dimethylbenzenesulfonamide (104.4 mg, 1.4 eq), and HCl (4.0 M in dioxane, 0.112 ml, 1.2 eq) were dissolved in EtOH and heated at 100° C. in a sealed tube for 20 h. After cooling to rt, the reaction was quenched with 7 M NH₃ in MeOH (5 ml). The reaction mixture was concentrated under reduced pressure to give a solid residue, MeOH was added and the resulting precipitate was collected by filtration to give 111 mg of the title compound. LCMS: MH+=433.1.

Example 13B

By essentially the same procedure set forth in Example 13A, substituting the aniline in column 1, the example in column 2 was synthesized.

| Ex. | Column 1 | Column 2 | LCMS MH+ |
|---|---|---|---|
| 13B | H2N-C6H4-S(O2)-NHAc | phenyl-pyrazolopyridine with CN, methyl, and HN-C6H4-S(O2)-NH2 substituents | 405.1 |

Because of their adenosine $A_{2a}$ receptor antagonist activity, compounds of the present invention are useful in the treatment of depression, cognitive function diseases and neurodegenerative diseases such as Parkinson's disease, senile dementia as in Alzheimer's disease, psychoses, attention deficit disorders, EPS, dystonia, RLS and PLMS. In particular, the compounds of the present invention can improve motor-impairment due to neurodegenerative diseases such as Parkinson's disease.

The other agents known to be useful in the treatment of Parkinson's disease that can be administered in combination with the compounds of formula I include: L-DOPA; dopaminergic agonists such as quinpirole, ropinirole, pramipexole, pergolide and bromocriptine; MAO-B inhibitors such as deprenyl and selegiline; DOPA decarboxylase inhibitors such as carbidopa and benserazide; and COMT inhibitors such as tolcapone and entacapone.

Adenosine $A_{2a}$ antagonists of the invention can also be co-administered with the antipsychotic agents known to cause the EPS and tricyclic antidepressants known to cause dystonia.

Antipsychotic agents causing the EPS treated by adenosine $A_{2a}$ receptor antagonists and for use in combination with adenosine $A_{2a}$ receptor antagonists include typical and atypical antipsychotic agents. Typical antipsychotics include loxapine, haloperidol, chlorpromazine, prochlorperazine and thiothixene. Atypical antipsychotics include clozapine, olanzapine, loxapine, quetiapine, ziprasidone and risperidone.

Tricyclic antidepressants causing dystonia treated by adenosine $A_{2a}$ receptor antagonists include perphenazine, amitriptyline, desipramine, doxepin, trimipramine and protriptyline. Anticonvulsants which may cause dystonia, but which also may be useful in treating ERLS or PLMS include phenytoin, carbamazepine and gabapentin.

Dopamine agonists useful in treating RLS and PLMS include pergolide, pramipexole, ropinerole, fenoldopam and cabergoline.

Opioids useful in treating PRLS and PLMS include codeine, hydrocodone, oxycodone, propoxyphene and tramadol.

Benzodiazepines useful in treating PRLS and PLMS include clonazepam, triazolam and temazepam.

The antipsychotics, tricyclic antidepressants, anticonvulsants, dopamine agonists, opioids and benzodiazepines are commercially available and are described in the literature, e.g., in The Physicians' Desk Reference (Montvale: Medical Economics Co., Inc., 2001).

One to three other agents can be used in combination with the compounds of formula I, preferably one.

The pharmacological activity of the compounds of the invention was determined by the following in vitro and in vivo assays to measure $A_{2a}$ receptor activity.

Human Adenosine $A_{2a}$ and $A_1$ Receptor Competition Binding Assay Protocol

Membrane Sources:
 $A_{2a}$: Human $A_{2a}$ Adenosine Receptor membranes, Catalog #RB-HA$_{2a}$, Receptor Biology, Inc., Beltsville, Md. Dilute to 17 μg/100 μl in membrane dilution buffer (see below).

Assay Buffers:
 Membrane dilution buffer: Dulbecco's Phosphate Buffered Saline (Gibco/BRL)+10 mM MgCl$_2$.
 Compound Dilution Buffer: Dulbecco's Phosphate Buffered Saline (Gibco/BRL)+10 mM MgCl$_2$ supplemented with 1.6 mg/ml methyl cellulose and 16% DMSO. Prepared fresh daily.

Ligands:
 $A_{2a}$: [3H]—SCH 58261, custom synthesis, AmershamPharmacia Biotech, Piscataway, N.J. Stock is prepared at 1 nM in membrane dilution buffer. Final assay concentration is 0.5 nM.
 $A_1$: [3H]-DPCPX, AmershamPharmacia Biotech, Piscataway, N.J. Stock is prepared at 2 nM in membrane dilution buffer. Final assay concentration is 1 nM.

Non-Specific Binding:
 $A_{2a}$: To determine non-specific binding, add 100 nM CGS 15923 (RBI, Natick, Mass.). Working stock is prepared at 400 nM in compound dilution buffer.
 $A_1$: To determine non-specific binding, add 100 μM NECA (RBI, Natick, Mass.). Working stock is prepared at 400 μM in compound dilution buffer.

Compound Dilution:
 Prepare 1 mM stock solutions of compounds in 100% DMSO. Dilute in compound dilution buffer. Test at 10 concentrations ranging from 3 μM to 30 μM. Prepare working solutions at 4× final concentration in compound dilution buffer.

Assay Procedure:
 Perform assays in deep well 96 well plates. Total assay volume is 200 μl. Add 50 μl compound dilution buffer (total ligand binding) or 50 μl CGS 15923 working solution ($A_{2a}$ non-specific binding) or 50 μl NECA working solution ($A_1$ non-specific binding) or 50 μl of drug working solution. Add 50 μl ligand stock ([3H]-SCH 58261 for $A_{2a}$, [3H]-DPCPX for $A_1$). Add 100 μl of diluted membranes containing the appropriate receptor. Mix. Incubate at room temperature for 90 minutes. Harvest using a Brandel cell harvester onto Packard GF/B filter plates. Add 45 μl Microscint 20 (Packard), and count using the Packard TopCount Microscintillation Counter. Determine $IC_{50}$ values by fitting the displacement curves using an iterative curve fitting program (Excel). Determine Ki values using the Cheng-Prusoff equation.

Haloperidol-Induced Catalepsy in the Rat

Male Sprague-Dawley rats (Charles River, Calco, Italy) weighing 175-200 g are used. The cataleptic state is induced by the subcutaneous administration of the dopamine receptor antagonist haloperidol (1 mg/kg, sc), 90 min before testing the animals on the vertical grid test. For this test, the rats are placed on the wire mesh cover of a 25×43 plexiglass cage placed at an angle of about 70 degrees with the bench table. The rat is placed on the grid with all four legs abducted and extended ("frog posture"). The use of such an unnatural posture is essential for the specificity of this test for catalepsy. The time span from placement of the paws until the first complete removal of one paw (decent latency is measured maximally for 120 sec.

The selective $A_{2A}$ adenosine antagonists under evaluation are administered orally at doses ranging between 1 and 10 mg/kg, 1 and 4 h before scoring the animals.

6-OHDA Lesion of the Middle Forebrain Bundle in Rats

Adult male Sprague-Dowley rats (Charles River, Calco, Como, Italy), weighing 275-300 g, are used in all experiments. The rats are housed in groups of 4 per cage, with free access to food and water, under controlled temperature and 12 hour light/dark cycle. The day before the surgery the rats are fasted over night with water ad libitum.

Unilateral 6-hydroxydopamine (6-OHDA) lesion of the middle forebrain bundle is performed according to the method described in Ungerstedt et al, *Brian Research*, 24 (1970), p. 485-493, and Ungerstedt, *Eur. J. Pharmacol.*, 5 (1968), p. 107-110, with minor changes. Briefly, the animals are anaesthetized with chloral hydrate (400 mg/kg, ip) and treated with desipramine (10 mpk, ip) 30 min prior to 6-OHDA injection in order to block the uptake of the toxin by the noradrenergic terminals. Then, the animals are placed in a stereotaxic frame. The skin over the skull is reflected and the stereotaxic coordinates (−2.2 posterior from bregma (AP), +1.5 lateral from bregma (ML), 7.8 ventral from dura (DV) are taken, according to the atlas of Pellegrino et al (Pellegrino L. J., Pellegrino A. S. and Cushman A. J., *A Stereotaxic Atlas of the Rat Brain*, 1979, New York: Plenum Press). A burr hole is then placed in the skull over the lesion site and a needle, attached to a Hamilton syringe, is lowered into the left MFB. Then 8 μg 6-OHDA-HCl is dissolved in 4 μl of saline with 0.05% ascorbic acid as antioxidant, and infused at the constant flow rate of 1 μl/1 min using an infusion pump. The needle is withdrawn after additional 5 min and the surgical wound is closed and the animals left to recover for 2 weeks.

Two weeks after the lesion the rats are administered with L-DOPA (50 mg/kg, ip) plus Benserazide (25 mg/kg, ip) and selected on the basis of the number of full contralateral turns quantified in the 2 h testing period by automated rotameters (priming test). Any rat not showing at least 200 complete turns/2 h is not included in the study.

Selected rats receive the test drug 3 days after the priming test (maximal dopamine receptor supersensitivity). The new $A_{2A}$ receptor antagonists are administered orally at dose levels ranging between 0.1 and 3 mg/kg at different time points (i.e., 1, 6, 12 h) before the injection of a subthreshold dose of L-DOPA (4 mpk, ip) plus benserazide (4 mpk, ip) and the evaluation of turning behavior.

Using the above test procedures, the following results were obtained for preferred and/or representative compounds of the invention.

Results of the binding assay on compounds of the invention showed $A_{2a}$ Ki values of about 0.1 to about 1800 nM, with preferred compounds showing Ki values between 0.1 and 100 nM.

Selectivity is determined by dividing Ki for A1 receptor by Ki for A2a receptor. Compounds of the invention have a selectivity ranging from about 1 to about 1600. Preferred are compounds are those wherein the selectivity is >100.

Preferred compounds showed about a 20-40% decrease in descent latency when tested for anti-cataleptic activity in rats.

One to three compounds of formula I can be administered in the method of the invention, preferably one.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound of formula I in a unit dose of preparation may be varied or adjusted from about 0.1 mg to 1000 mg, more preferably from about 1 mg to 300 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgment of the attending clinician considering such factors as age, condition and size of the patient as well as severity of the symptoms being treated. A typical recommended dosage regimen for compounds of formula I is oral administration of from 10 mg to 2000 mg/day preferably 10 to 1000 mg/day, in two to four divided doses to provide relief from central nervous system diseases such as Parkinson's disease or the other disease or conditions listed above.

The doses and dosage regimen of the other agents used in the treatment of Parkinson's disease will be determined by the attending clinician in view of the approved doses and dosage regimen in the package insert, taking into consideration the age, sex and condition of the patient and the severity of the disease. It is expected that when the combination of a compound of formula I and another agent useful for treating Parkinson's disease, EPS, dystonia, RLS or PLMS is administered, lower doses of the components will be effective compared to the doses of the components administered as monotherapy. When administered in combination, the compound(s) of formula I and the other agent(s) for treating Parkinson's disease, EPS, dystonia, RLS or PLMS can be administered simultaneously or sequentially. This is particularly useful when the components of the combination are preferably given on different dosing schedules, e.g., one component is administered daily and another every six hours, or when the preferred pharmaceutical compositions are different, e.g. one is preferably a tablet and one is a capsule. A kit comprising the separate dosage forms is therefore advantageous.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

We claim:
1. A compound represented by the structural formula I

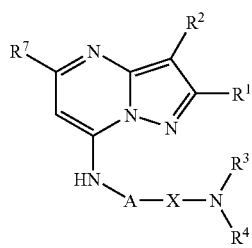

or a pharmaceutically acceptable salt thereof, wherein:
A is alkylene, $R^{16}$-arylene, $R^{16}$-cycloalkylene or $R^{16}$-heteroaryldiyl;
X is —C(O)— or —S(O)$_2$—;
$R^1$ is alkyl or cycloalkyl;
$R^2$ is hydrogen, halo or —CN;
$R^3$ is hydrogen or alkyl;
$R^4$ is hydrogen, alkyl, alkoxy, hydroxyalkyl, -alkyl-$NR^{14}R^{15}$, cycloalkyl, heterocycloalkyl, heterocycloalkyl substituted by alkyl, $R^8$-arylalkyl or $R^8$-heteroarylalkyl;
or $R^3$ and $R^4$ together with the nitrogen to which they are attached, form a 5-7 membered ring, said ring optionally comprising an additional heteroatom ring member selected from the group consisting of —O—, —S— and —N($R^{17}$)—, said ring being optionally substituted by alkyl, hydroxyalkyl, $R^8$-arylalkyl, $R^8$-heteroarylalkyl, —N($R^9$)—C(O)alkyl, —CO$_2$-alkyl, —C(O)NR$^{10}$R$^{11}$ or heterocycloalkyl;
or $R^3$ and $R^4$ together with the nitrogen to which they are attached, form the group

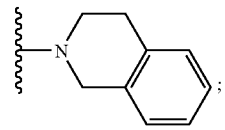

$R^7$ is alkyl, $R^{12}$-phenyl, $R^{12}$-heteroaryl, cycloalkyl, halo, morpholinyl,

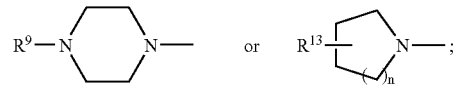

n is 1 or 2;
$R^8$ is 1-3 substituents independently selected from the group consisting of hydrogen, alkyl, halo, alkoxy, —CO$_2$H, —CO$_2$-alkyl, —CF$_3$, —CN, —CO$_2$NR$^{14}$R$^{15}$, —SO$_2$-alkyl,
—SO$_2$NR$^{14}$R$^{15}$ and —NR$^{14}$R$^{15}$;
$R^9$ is hydrogen or alkyl;
$R^{10}$ and $R^{11}$ are independently selected from the group consisting of alkyl and cycloalkyl; or $R^{10}$ and $R^{11}$ form a C$_4$-C$_5$ alkylene chain and together with the nitrogen to which they are attached, form a 5- or 6-membered ring;
$R^{12}$ is 1 to 3 substituents independently selected from the group consisting of hydrogen, alkyl, halo, alkoxy, —CO$_2$H, —CO$_2$-alkyl, —CF$_3$, —CN, —CO$_2$NR$^{14}$R$^{15}$, —SO$_2$-alkyl, —SO$_2$NR$^{14}$R$^{15}$ and —NR$^{14}$R$^{15}$;
$R^{13}$ is H, OH, hydroxyalkyl or alkyl;
$R^{14}$ and $R^{15}$ are independently selected form the group consisting of hydrogen, alkyl and cycloalkyl;
$R^{16}$ is 1 to 3 substituents independently selected from the group consisting of hydrogen, alkyl, halo, OH and alkoxy; and
$R^{17}$ is hydrogen, alkyl, cycloalkyl or $R^8$-arylalkyl.
2. A compound of claim 1 wherein $R^1$ is methyl or cyclopropyl.
3. A compound of claim 1 wherein A is $R^{16}$-arylene.
4. A compound of claim 3 wherein A is phenylene.
5. A compound of claim 1 wherein $R^7$ is $R^{12}$-phenyl, pyridyl or

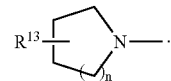

6. A compound of claim 5 wherein $R^7$ is

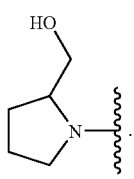

7. A compound of claim 1 wherein X is —S(O)$_2$— and $R^7$ is 2-pyridyl.

8. A compound of claim 1 wherein X is —C(O)— and $R^7$ is 2-, 3- or 4-pyridyl.

9. A compound of claim 1 wherein X is —S(O)$_2$—, $R^1$ is methyl, and $R^2$ is CN, Cl or Br.

10. A compound of claim 1 wherein X is —S(O)$_2$—, $R^1$ is cyclopropyl, and $R^2$ is H.

11. A compound represented by the structural formula I

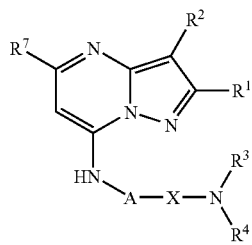

or a pharmaceutically acceptable salt thereof, wherein:
  A is alkylene, $R^{16}$-arylene, $R^{16}$-cycloalkylene or $R^{16}$-heteroaryldiyl;
  $R^1$ is alkyl or cycloalkyl;
  $R^2$ is hydrogen, halo or —CN;
  X is —S(O)$_2$—;
  —NR$^3$R$^4$ is selected from the group consisting of

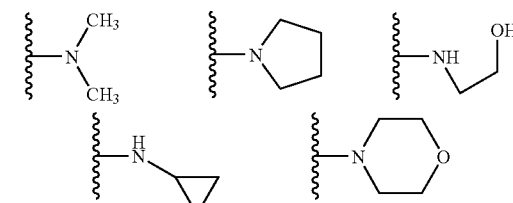

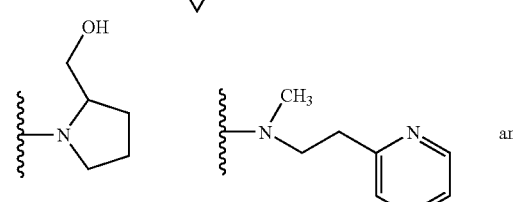

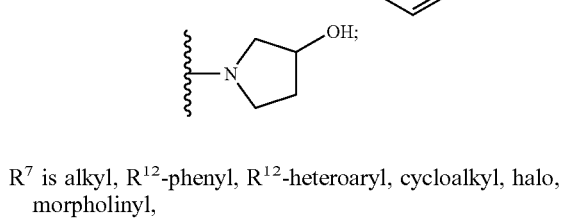

$R^7$ is alkyl, $R^{12}$-phenyl, $R^{12}$-heteroaryl, cycloalkyl, halo, morpholinyl,

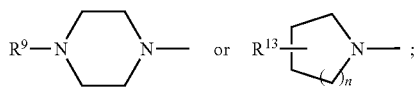

n is 1 or 2;
$R^9$ is hydrogen or alkyl;
$R^{12}$ is 1 to 3 substituents independently selected from the group consisting of hydrogen, alkyl, halo, alkoxy, —CO$_2$H, —CO$_2$-alkyl, —CF$_3$, —ON, —CO$_2$NR$^{14}$R$^{15}$, —SO$_2$-alkyl, —SO$_2$NR$^{14}$R$^{15}$ and —NR$^{14}$R$^{15}$;
$R^{13}$ is H, OH, hydroxyalkyl or alkyl;
$R^{14}$ and $R^{15}$ are independently selected form the group consisting of hydrogen, alkyl and cycloalkyl; and
$R^{16}$ is 1 to 3 substituents independently selected from the group consisting of hydrogen, alkyl, halo, OH and alkoxy.

12. A compound of claim 1 wherein X is —C(O)— and —NR$^3$R$^4$ is selected from the group consisting of:

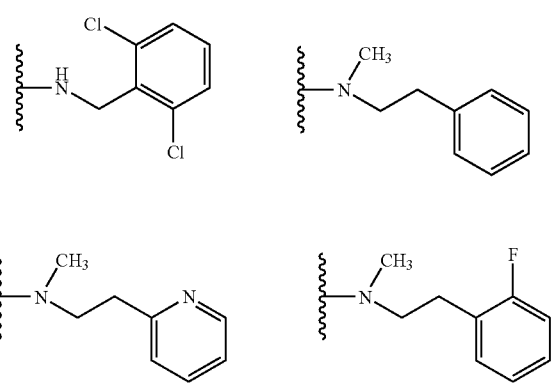

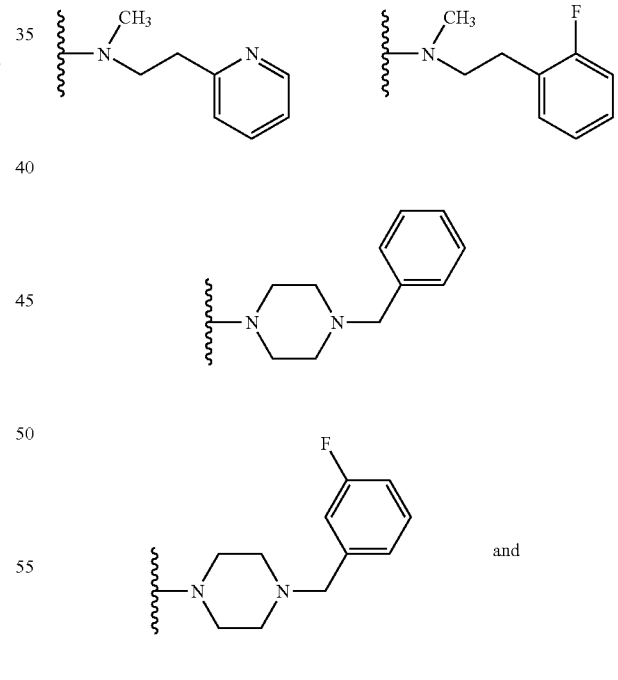

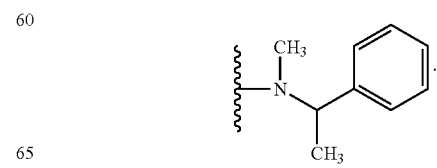

13. A compound represented by the structural formula I

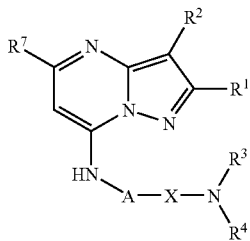

or a pharmaceutically acceptable salt thereof, wherein X is —S(O)$_2$—, A is phenylene, R$^1$ is methyl, R$^2$ is Br, R$^7$ is phenyl or

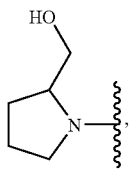

and —NR$^3$R$^4$ is

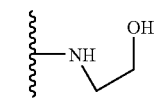   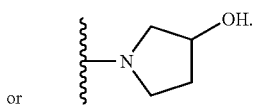

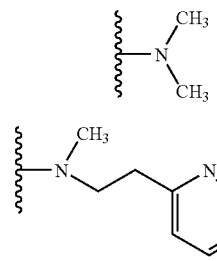 or

14. A compound of claim 1 wherein X is —C(O)—, A is phenylene, R$^1$ is cyclopropyl, R$^2$ is hydrogen, R$^7$ is phenyl or

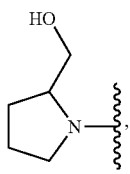

and —NR$^3$R$^4$ is

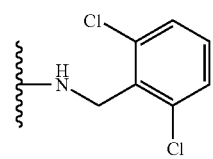 or 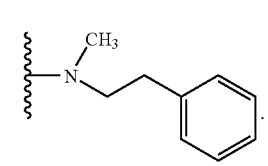.

15. A compound of claim 1 wherein X is —C(O)—, A is phenylene, R$^1$ is methyl, R$^2$ is hydrogen, R$^7$ is phenyl or

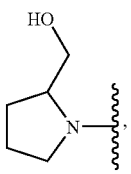

and —NR$^3$R$^4$ is

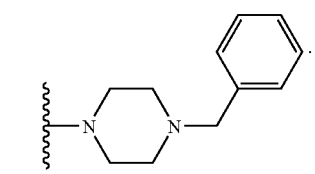.

16. A compound selected from the group consisting of

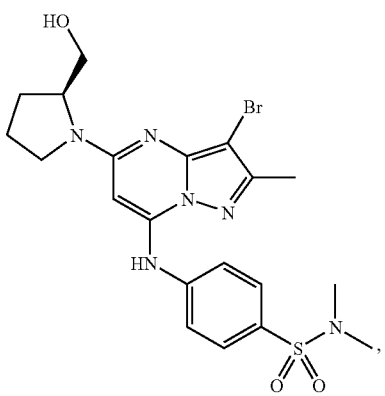

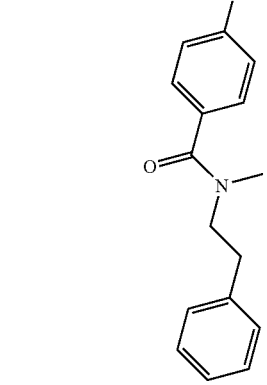

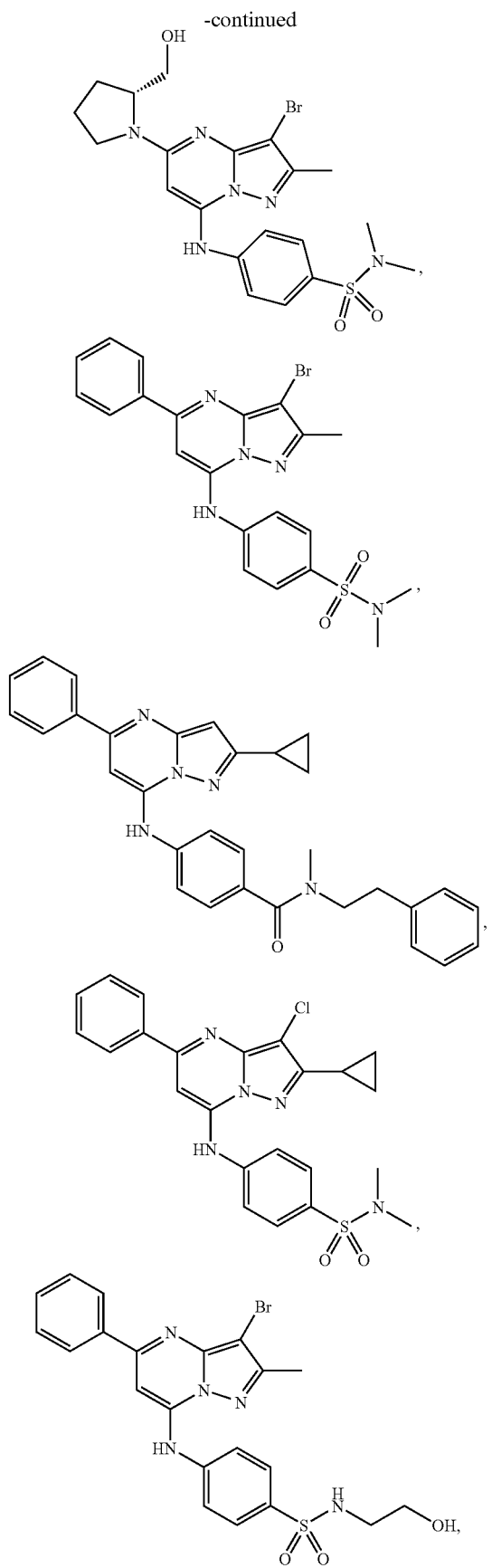
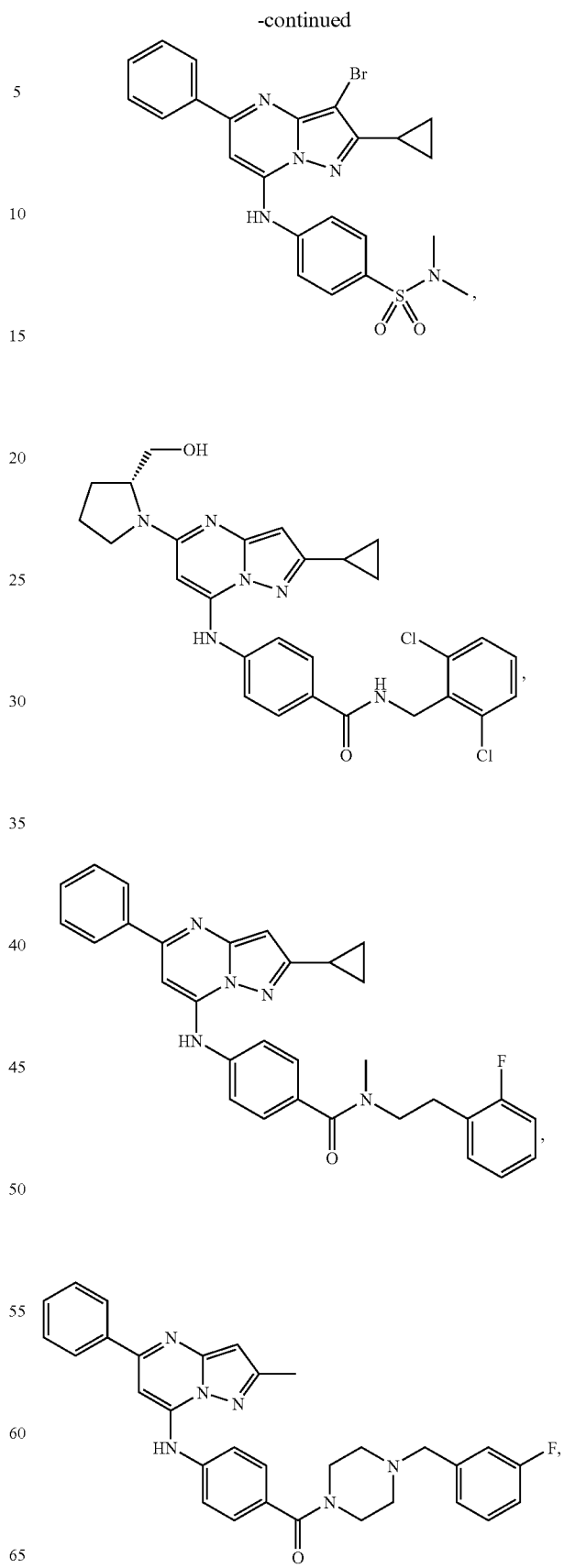

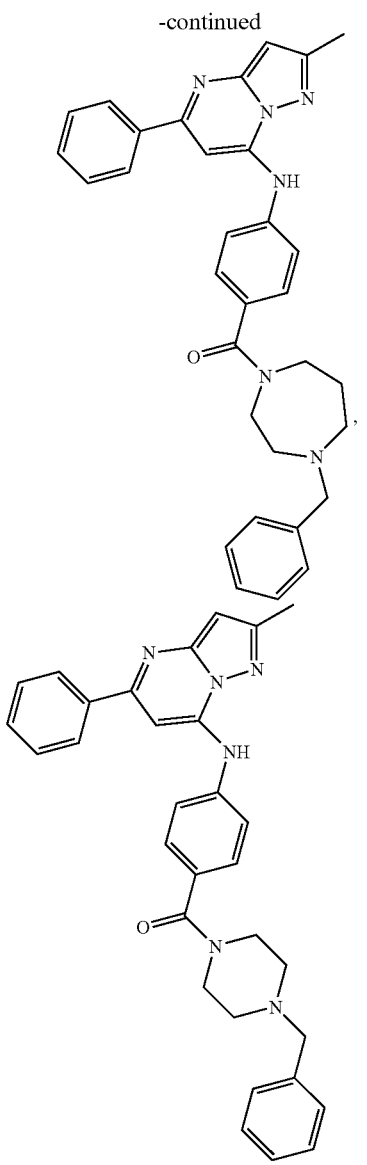

and

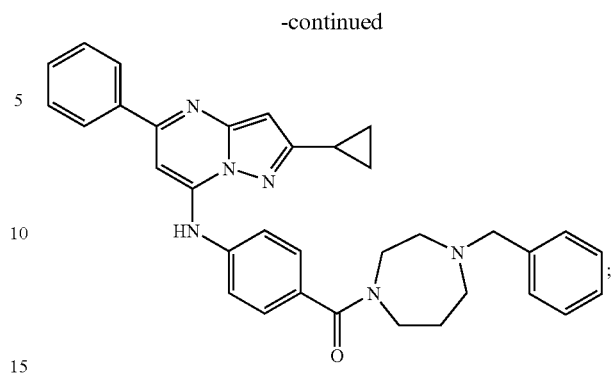

or a pharmaceutically acceptable salt thereof.

17. A pharmaceutical composition comprising a therapeutically effective amount of a compound of claim 1 or a pharmaceutically acceptable salt thereof in a pharmaceutically acceptable carrier.

18. A pharmaceutical composition comprising a therapeutically effective amount of a compound of claim 11 or a pharmaceutically acceptable salt thereof in a pharmaceutically acceptable carrier.

19. A pharmaceutical composition comprising a therapeutically effective amount of a compound of claim 13 or a pharmaceutically acceptable salt thereof in a pharmaceutically acceptable carrier.

20. A pharmaceutical composition comprising a therapeutically effective amount of a compound of claim 16 or a pharmaceutically acceptable salt thereof in a pharmaceutically acceptable carrier.

* * * * *